US012797474B2

(12) United States Patent
Svirskis et al.

(10) Patent No.: US 12,797,474 B2
(45) Date of Patent: Nov. 17, 2026

(54) BIOACTIVE IMPLANTS FOR DRUG DELIVERY

(71) Applicant: The Queen's University of Belfast, Belfast (GB)

(72) Inventors: Darren Svirskis, Auckland (NZ); Andrew Hill, Auckland (NZ); Prabhat Bhusal, Auckland (NZ); Manisha Sharma, Auckland (NZ); Priyanka Agarwal, Auckland (NZ); Gavin Andrews, Belfast (GB); David Jones, Belfast (GB); Shu Li, Belfast (GB)

(73) Assignee: The Queen's University of Belfast, Belfast (GB)

( * ) Notice: Subject to any disclaimer, the term of this patent is extended or adjusted under 35 U.S.C. 154(b) by 877 days.

(21) Appl. No.: 17/760,866

(22) PCT Filed: Sep. 17, 2020

(86) PCT No.: PCT/EP2020/075927

§ 371 (c)(1),
(2) Date: Mar. 16, 2022

(87) PCT Pub. No.: WO2021/053047

PCT Pub. Date: Mar. 25, 2021

(65) Prior Publication Data

US 2023/0036339 A1 Feb. 2, 2023

(30) Foreign Application Priority Data

Sep. 18, 2019 (GB) ..................................... 1913456

(51) Int. Cl.

| | |
|---|---|
| ***A61K 47/32*** | (2006.01) |
| ***A61K 9/70*** | (2006.01) |
| ***A61K 31/167*** | (2006.01) |
| ***A61K 31/245*** | (2006.01) |
| ***A61K 31/445*** | (2006.01) |
| ***A61P 23/02*** | (2006.01) |

(52) U.S. Cl.

CPC ............ *A61K 47/32* (2013.01); *A61K 9/7007* (2013.01); *A61K 31/167* (2013.01); *A61K 31/245* (2013.01); *A61K 31/445* (2013.01); *A61P 23/02* (2018.01)

(58) Field of Classification Search

None

See application file for complete search history.

(56) References Cited

U.S. PATENT DOCUMENTS

| | | | | | |
|---|---|---|---|---|---|
| 2002/0045668 | A1 * | 4/2002 | Dang | A61K 9/1641 | 514/649 |
| 2007/0154527 | A1 * | 7/2007 | Myers | A61K 47/38 | 424/59 |
| 2013/0203602 | A1 | 8/2013 | Riisager et al. | | |
| 2014/0066523 | A1 * | 3/2014 | Knaack | A61K 31/167 | 514/772.7 |
| 2015/0105426 | A1 * | 4/2015 | Lazerges | A61K 47/26 | 514/626 |

FOREIGN PATENT DOCUMENTS

| | | | |
|---|---|---|---|
| CN | 110327283 | A | 10/2019 |
| JP | 2013-116861 | A | 6/2013 |
| WO | WO9600047 | * | 1/1996 |

OTHER PUBLICATIONS

Paavola et al. (Controlled release and dura mater permeability of lidocaine and ibuprofen from injectable poloxamer-based gels, Journal of Controlled Release 52 1998) 169-178). (Year: 1998).*

Darzi, M.E., et al., Thermal and electrical performance analysis of co-electrosprayed PCM nanofiber composites in the presence of graphene and carbon fiber powder, Renewable Energy, Dec. 8, 2018, vol. 135, pp. 719-728.

* cited by examiner

*Primary Examiner* — Melissa S Mercier

(74) *Attorney, Agent, or Firm* — Hodgson Russ LLP

(57) ABSTRACT

The invention provides a device comprising: at least one biocompatible polymer, and an eutectic composition comprising a first agent and an agent capable of forming a eutectic composition with the first agent; or one or more fatty acids; or one or more fatty alcohols; or one or more fatty amines or combinations thereof. The device can be administered to a subject in need thereof an effective amount of one or more active agents. The at least one biocompatible polymer may be selected from the group comprising poly ethylene-vinyl-acetate, vinyl acetate, silicone, polycaprolactone, polylacticco-glycolic acid, polylactic acid or polyglycolic acid.

4 Claims, 23 Drawing Sheets

BIOACTIVE IMPLANTS FOR DRUG DELIVERY

FIELD OF THE INVENTION

The present invention relates to medical devices comprising one or more polymers, including insertable and implantable medical devices comprising one or more polymers. The invention provides polymer based medical devices comprising eutectic mixtures.

The invention addresses problems with existing medical devices that are implanted or inserted into the body, and/or those that are used to deliver one or more active agents to or into a subject's body.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art. Any discussion of the prior art throughout the specification should in no way be considered as an admission that such prior art is widely known or forms part of the common general knowledge in the field.

Drug delivery systems in the form of implants, matrices and reservoirs can be used for delivery of anaesthetics, analgesics, chemotherapy and other drugs to the body. Drug loading can be difficult to maximize and stabilise, while release kinetics can be difficult to control. Insertion and removal can be painful. Likewise, the insertion and removal of a device such as a catheter can result in pain, mechanical injury, inflammation and bleeding. Furthermore, the local trauma can manifest in conditions such as urethritis and cystitis, which can be difficult to treat.

A multitude of approaches can be used to regulate the release rate of a drug from an implant at a target site for a particular duration of time. Unlike conventional medicine dosage forms, special polymers or encapsulating agents are used in implantable delivery systems by which the drug is released safely in a controlled fashion for a prolonged period of time.

Traditional implantable drug delivery systems include matrix, reservoir and osmotic systems. Implantable drug delivery systems can be made from biodegradable or non-biodegradable materials. Biodegradable implants degrade slowly inside the body and release of drugs occurs both by erosion and diffusion.

Meanwhile, non-biodegradable implants do not degrade inside the body and drug is released by diffusion. These non-biodegradable implants are particularly useful when controlled release of a drug over a relatively longer period is required. For instance, Implanon® and Norplani® can release contraceptives over a period of five years. They have an additional advantage in that they can be removed when their therapeutic activity is no longer required, or in the event of an adverse reaction.

Typical drug treatment involves frequent administration of medicines resulting in fluctuating levels of drugs in the body, thereby risking toxicity during times of peak plasma concentrations and treatment failure during troughs. Implantable dosage forms of medicine have the ability to maintain drug levels within the therapeutic range for a prolonged period of time and thus improve treatment. However, drug loading into polymer carriers is limited, with crystallisation and other events occurring as the drug concentration in the polymer is increased beyond the solubility limit. Crystallisation is undesirable for a number of reasons including an alteration in drug release kinetics, the potential for loss of dose before administration and changing properties over time (stability issues).

Local anesthetics are used in implantable drug delivery systems to provide temporary analgesia following surgery. Appropriate management to minimise complications is essential to promote a patient's post-operative recovery. As with other drugs, limitations in drug loading have constrained the utility of anaesthetic implants following surgery.

Currently available biodegradable polymer drug delivery matrices for long-term delivery of active agents, such as analgesics, suffer from inability to maintain a constant drug release rate for several months or longer time periods, in part because channels form in the polymer matrix as it degrades, resulting in increased release rates. In addition to channeling, other durability issues limiting state of the art biodegradable implants include softening overtime and gradual loss of structural integrity. The tendency of implants to fragment makes implant removal difficult if not impossible.

A eutectic is a mixture of substances (in particular proportions) that melts and freezes at a single temperature that is lower than the melting points of the separate constituents or any other mixture of them. A eutectic depicts a typical V-shaped phase diagram, and the crystal lattice of the individual constituents are retained. It has been suggested that the constituents of a eutectic have a shape/size mismatch and therefore cannot form a continuous solid solution. Furthermore, it is anticipated effective adhesive interactions are absent in a eutectic, excluding the formation of a co-crystal. EMLA® (eutectic mixture of local anaesthetics) is a commercially available topical cream composed of the eutectic that is formed between lidocaine and prilocaine. The former melts at 68° C. and the latter at 38° C., however when combined the 1:1 M eutectic composition has a melting point of 22° C. EMLA® cream is formed as an emulsion, however the eutectic solely forms the oily phase and hence, a system with increased thermodynamic activity of the local anaesthetics exist as they are not partitioned into the inert oil phases. In another commercially available example, the steroids present in Nuvaring®, etonogestrel and ethyl estradiol, have been observed to form a eutectic in a 1:1 molar ratio which melt approximately 50° C. lower than the individual components at approximately 143° C. (162).

It is an object of the present invention to provide one or more polymer-based medical device, such as but not limited to an implant, comprising a eutectic composition, and/or to overcome one or more of the problems discussed herein with existing medical devices, including with existing insertable and implantable medical devices, or to at least provide the public with a useful choice.

SUMMARY OF THE INVENTION

This invention relates to the use of eutectic mixtures in polymer based medical devices and implants.

The invention provides polymer medical devices comprising at least one polymer at least one eutectic mixture.

The eutectic mixture may comprise one or more agents and one or more of the group selected from a fatty acid, a fatty amine, a fatty alcohol, or any combination of two or more thereof.

The present invention provides a device comprising:

a) at least one biocompatible polymer; and b) an eutectic composition.

The eutectic composition comprises a first agent and one or more of the group comprising i) one or more active agents capable of forming a eutectic composition with the first agent; or
ii) one or more fatty acids; or
iii) one or more fatty alcohols; or
iv) one or more fatty amines; or
v) any combination of i) to iv) above, including any combination of two or more of i) to iv).

Preferably the polymer is a non-biodegradable biocompatible polymer.

A preferred polymer is or includes EVA.

In one embodiment, the biocompatible polymer is biodegradeable.

In one embodiment, the biocompatible polymer is substantially non-biodegradeable.

In various embodiments, the at least one biocompatible polymer is selected from the group comprising poly ethylene-vinyl-acetate (EVA), vinyl acetate, silicone, polycaprolactone, polylacticco-glycolic acid (PLGA), polylactic acid (PLA) and polyglycolic acid. In specific examples, the polymer is EVA.

In various embodiments, the EVA comprises from 0% to about 40% w/w polyvinyl acetate.

In certain embodiments in which the implant comprises EVA, the ratio of ethylene (E) to vinyl acetate (VA) present in the EVA is from about 0.01:1 to about 100:1, for example, from about 0.1:1 to about 100:1, from about 0.1:1 to about 5:1, or from about 0.1:1 to about 1:1. In particularly contemplated embodiments comprising EVA, the ratio of ethylene (E) to vinyl acetate (VA) present in the EVA is from about 1:1 to about 10:1, for example, from about 2:1 to about 10:1, from about 3:1 to about 10:1, from about 4:1 to about 10:1, from about 5:1 to about 10:1, from about 6:1 to about 10:1, from about 7:1 to about 10:1, from about 8:1 to about 10:1, or from about 9:1 to about 10:1. For example, the ratio of ethylene (E) to vinyl acetate (VA) present in the EVA is from about 3:2 to about 4:1, for example, from about 7:3 to about 3:1, or about 7:3.

Specifically contemplated EVAs for active agent loading uses as described herein include EVAs having an polyvinyl acetate content of at least about 25% w/w with respect to polyethylene, for example, at least 30% w/w, or at least about 33% w/w.

Further specifically contemplated EVAs, for example for structural uses and/or non-active agent loading uses, including for example providing radio opacity, barium sulfate incorporation, and the like include EVAs having an vinyl acetate content of about 20% w/w or less with respect to ethylene, for example, of about 15% w/w or less, of about 12% w/w/or less, or of about 10% w/w or less with respect to ethylene.

In one particularly contemplated embodiment, the device, for example the implant, comprises a core comprising a first polymer, such as a core comprising EVA having a vinyl acetate content of about 10% w/w with respect to ethylene to about 20% w/w, and an outer layer comprising a second polymer, such as EVA having an vinyl acetate content of at least about 25% w/w with respect to ethylene, for example, at least 30% w/w, or at least about 33% w/w, wherein the outer layer comprises the eutectic composition.

In one example, the device, for example the implant, comprises a core comprising a first polymer comprising EVA having a vinyl acetate content of from about 10-12% w/w with respect to ethylene, and an outer layer comprising EVA having a vinyl acetate content of from about 30% w/w to about 35% w/w with respect to ethylene.

In certain embodiments, the eutectic mixture comprises at least one fatty acid, fatty alcohol and/or fatty amine to generate eutectic oils in situ within a polymer device.

Preferably the eutectic mixture comprises at least one fatty acid.

The fatty acid may be hexanoic acid (C6), hexanedioic acid (CM), a dicarboxylic fatty acid, capric acid (C10), decanedioic acid (C10), lauric acid (C12), dodecanedioic acid (C12), tetradecanedioic acid (C14), Capric acid, Myristic acid, Oleic acid.

The eutectic mixture may comprise a fatty acid and a second fatty acid, a fatty alcohol, a fatty amine or a drug or other agent.

The invention provides the use of eutectic mixtures to increase the lubricity of devices.

The device can generate eutectic oils in situ within medical devices which exude from the material and in so doing render the surface lubricious The eutectic mixture can comprise a drug capable of forming a eutectic mixture with a fatty acid, alcohol or amine.

The fatty alcohol may be 1-Dodecanol, Heneicosanol, Elaidyl alcohol, Petroselinyl alcohol, 1-tetradecanol, 1-Docosanol, 1-Tridecanol, 1-Nonadecanol, 1-Triacontanol, 1-Pentadecanol, 1-Nonanol, 1-Tricosanol, Cetyl alcohol, Stearyl alcohol, 1-Decanol, Isooctyl alcohol.

The fatty amine may be Pentadecylamine, Hexadecylamine, Docecylamine, Decylamine, Tridecylamine, Octadecylamine, Undecylamine, N, N-dimethyltetradecylamine, Dodecylamine, Octadecylamine The drug may be lidocaine, prilocaine, roprivacaine or similar.

By using a eutectic form of a drug within a polymer carrier the drug loading and delivery capacity is increased.

Having the drug present in the polymer carrier in a eutectic form allows for higher drug loading with improved stability.

The controlled delivery of drugs through implants can improve the management of post-operative pain, inflammation and infection, promoting faster post-operative recovery.

The controlled delivery of local anaesthetic or analgesia through implants can decrease opiate consumption.

In one embodiment the invention provides a polymer implant loaded with a local anaesthetic and a fatty acid in a eutectic mixture.

In one particular embodiment, the invention provides an intraperitoneal implant loaded with the local anaesthetic, lidocaine in a eutectic 1:1 mixture with myristic acid, in a poly(ethylene-co-vinyl acetate) (EVA) carrier manufactured using hot melt extrusion.

Other particular combinations include the following:

Lidocaine—Fatty Acids

Lidocaine—hexanoic acid (C6); Lidocaine—hexanedioic acid (C6): NOTE: A dicarboxylic fatty acid.

Lidocaine—capric acid (C10); Lidocaine—decanedioic acid (C10); Lidocaine—lauric acid (C12); Lidocaine—dodecanedioic acid (C12): NOTE: A dicarboxylic fatty acid.

Lidocaine—tetradecanedioic acid (C14): NOTE: A dicarboxylic fatty acid.

Lidocaine—Fatty Alcohols

Lidocaine—3-methyl-3-pentanol (C6); Lidocaine—1-decanol (C10); Lidocaine—1-dodecanol (C12); Lidocaine—1-tetradecanol (C14).

Prilocaine—Fatty Acids

Prilocaine—hexanedioic acid (C6): NOTE: A dicarboxylic fatty acid; Prilocaine—decanedioic acid (C6):

NOTE: A dicarboxylic fatty acid; Prilocaine—dodecanoic acid (C12, Lauric Acid)

Ropivacaine—Fatty Acids

Ropivacaine—decanoic acid (C10); Ropivacaine—decanedioic acid (C10): NOTE: A dicarboxylic fatty acid.

Ropivacaine—dodecanoic acid (C12).

Ropivacaine—Fatty Alcohols

Ropivacaine—1-decanol (C10); Ropivacaine—1-tetradecanol (C14)

Fatty Acids—Fatty Acids

Capric acid (65% w/w) and Lauric acid (35% w/w); Capric acid (75% w/w) and Myristic acid (25% w/w); Oleic acid (80% w/w) and Lauric acid (20% w/w); Oleic acid (80% w/w) and Capric acid (20% w/w).

Features of certain embodiments of the implant include any one or more of the following:

- Drug content is uniformly spread along the length of the body of the polymer. This allows for an implant to be cut at the bedside and for length to correlate with dose.
- The drug is maintained as solid dispersion, which in certain embodiments requires crystallisation inhibitors above a certain drug loading.
- The device is simple to use—easy to locate at the site of injury and easy to remove with only minimal disruption.
- To maintain the location of one end of the implant and to facilitate removal, an end cap (a 't'-cap or circular cap) is sutured to the patient skin
- The implant is prepared as a single dose size, including a dose capable of being adjusted to patient specifications at the bedside by cutting the implant to length; the implant would have markings along its length corresponding to doses or patient weights.
- The device is in some embodiments made of a non-biodegradable or biodegradable polymer, or a mixture of biodegradable and non-biodegradable polymer.
- Devices with different layers, including different actives and/or having different release profiles and could be used to allow differential release profiles.

In certain embodiments, an implant according to the invention is adapted to be loaded with an active agent, such as a chemotherapy agent, with the aim of delivering the active agent over a prolonged period. For example, such a sustained release implant in one embodiment comprises a reservoir device formed via co-extrusion, wherein the reservoir is adapted for loading with one or more active agents. In such embodiments, the active agent resides within the implant, for example in the inner core, whereby the desired release rate of active agent is achieved by, for example, controlling the thickness or composition of one or more of the outer layers of the implant.

In one aspect, the invention relates to a method of administering to a subject in need thereof an effective amount of one or more active agents, the method comprising administering to the subject a device comprising a) at least one biocompatible polymer; and
b) an eutectic composition comprising a first active agent and one or more of the group comprising
  i) one or more active agents capable of forming a eutectic composition with the first active agent; or
  ii) one or more fatty acids; or
  iii) one or more fatty alcohols; or
  iv) one or more fatty amines; or
  v) any combination of i) to iv) above, including any combination of two or more of i) to iv).

In another aspect, the invention relates to a method of treating a disease or condition in a subject in need thereof, the method comprising administering to the subject a device comprising a) at least one biocompatible polymer; and
b) an eutectic composition comprising a first active agent and one or more of the group comprising
  i) one or more active agents capable of forming a eutectic composition with the first active agent; or
  ii) one or more fatty acids; or
  iii) one or more fatty alcohols; or
  iv) one or more fatty amines; or
  v) any combination of i) to iv) above, including any combination of two or more of i) to iv);

wherein the first active agent and/or one or more active agents is present in a therapeutically effective amount.

In another aspect, the invention relates to a device comprising a) at least one biocompatible polymer; and
b) an eutectic composition comprising a first active agent and one or more of the group comprising
  i) one or more active agents capable of forming a eutectic composition with the first active agent; or
  ii) one or more fatty acids; or
  iii) one or more fatty alcohols; or
  iv) one or more fatty amines; or
  v) any combination of i) to iv) above, including any combination of two or more of i) to iv);

wherein the first active agent and/or one or more active agents is present in a therapeutically effective amount.

In one embodiment, the device is an implant suitable for administration by implantation. In one embodiment, the device is an insertable device. In one embodiment, the device is suitable for topical administration, for example, as or in conjunction with a wound dressing.

In various embodiments, the one or more active agents is selected from the group comprising analgesics, anaesthetics including local anaesthetics, chemotherapeutics, NSAIDS, opiates, inflammatory modulators, wound healing agents, agents which regulate bleeding including anti-coagulants or coagulants, antibiotics, antivirals, antifungals and anthelmintics.

In another aspect, the invention relates to a method of treating or preventing pain in a subject in need thereof, the method comprising administering to the subject a device comprising a) at least one biocompatible polymer; and
b) an eutectic composition comprising a first active agent and one or more of the group comprising
  i) one or more active agents capable of forming a eutectic composition with the first active agent; or
  ii) one or more fatty acids; or
  iii) one or more fatty alcohols; or
  iv) one or more fatty amines; or
  v) any combination of i) to iv) above, including any combination of two or more of i) to iv);

wherein the first active agent and/or one or more of the active agents is an analgesic present in an analgesically-effective amount.

Any of the embodiments described herein may relate to any of the aspects described herein.

In various embodiments, the subject has undergone or is to undergo surgery. In various examples, subject has undergone or is to undergo abdominal surgery, including but not limited to appendectomy, gynaecological surgery, caesarean section, hernia repair, or tissue resection such as gut resection or the removal of cancerous tissue. In other examples, the subject is suffering from nerve damage, or would benefit from the temporary interruption of local or regional nerve transmission.

In one example, the device, for example, the implant, is administered at or proximal to the surgical site.

In one embodiment, the invention relates to a method of administering to a subject in need thereof an effective amount of one or more analgesics, the method comprising administering to the subject a device comprising a) at least one biocompatible polymer; and b) an eutectic composition comprising a first active agent and one or more of the group comprising i) one or more active agents capable of forming a eutectic composition with the first active agent; or ii) one or more fatty acids; or iii) one or more fatty alcohols; or iv) one or more fatty amines; or v) any combination of i) to iv) above, including any combination of two or more of i) to iv).

In another embodiment, the invention relates to a method of administering to a subject in need thereof an effective amount of one or more anaesthetics, the method comprising administering to the subject a device comprising a) at least one biocompatible polymer; and b) an eutectic composition comprising a first active agent and one or more of the group comprising i) one or more active agents capable of forming a eutectic composition with the first active agent; or ii) one or more fatty acids; or iii) one or more fatty alcohols; or iv) one or more fatty amines; or v) any combination of i) to iv) above, including any combination of two or more of i) to iv).

In one embodiment, the method comprises implanting or inserting in the subject an implant comprising at least one biocompatible polymer, together with one or more active agents in a eutectic composition with one or more fatty acids.

In one embodiment, the biocompatible polymer is biodegradeable.

In one embodiment, the biocompatible polymer is substantially non-biodegradeable.

In various embodiments, the at least one biocompatible polymer is selected from the group comprising poly ethylene-vinyl-acetate (EVA), vinyl acetate, silicone, polycaprolactone, polylacticco-glycolic acid (PLGA), polylactic acid (PLA). In specific examples, the polymer is EVA.

In various embodiments, the EVA comprises from 0% to about 40% w/w polyvinyl acetate.

In certain embodiments in which the implant comprises EVA, the ratio of ethylene (E) to vinyl acetate (VA) present in the EVA is from about 0.01:1 to about 100:1, for example, from about 0.1:1 to about 100:1, from about 0.1:1 to about 5:1, or from about 0.1:1 to about 1:1. In particularly contemplated embodiments comprising EVA, the ratio of ethylene (E) to vinyl acetate (VA) present in the EVA is from about 1:1 to about 10:1, for example, from about 2:1 to about 10:1, from about 3:1 to about 10:1, from about 4:1 to about 10:1, from about 5:1 to about 10:1, from about 6:1 to about 10:1, from about 7:1 to about 10:1, from about 8:1 to about 10:1, or from about 9:1 to about 10:1. For example, the ratio of ethylene (E) to vinyl acetate (VA) present in the EVA is from about 3:2 to about 4:1, for example, from about 7:3 to about 3:1, or about 7:3.

Specifically contemplated EVAs for active agent loading uses as described herein include EVAs having an polyvinyl acetate content of at least about 25% w/w with respect to polyethylene, for example, at least 30% w/w, or at least about 33% w/w.

Further specifically contemplated EVAs, for example for structural uses and/or non-active agent loading uses, including for example providing radio opacity, barium sulfate incorporation, and the like include EVAs having an vinyl acetate content of about 20% w/w or less with respect to ethylene, for example, of about 15% w/w or less, of about 12% w/w/or less, or of about 10% w/w or less with respect to ethylene.

In one particularly contemplated embodiment, the device, for example the implant, comprises a core comprising a first polymer, such as a core comprising EVA having a vinyl acetate content of about 10% w/w with respect to ethylene to about 20% w/w, and an outer layer comprising a second polymer, such as EVA having an vinyl acetate content of at least about 25% w/w with respect to ethylene, for example, at least 30% w/w, or at least about 33% w/w, wherein the outer layer comprises the eutectic composition.

In one example, the device, for example the implant, comprises a core comprising a first polymer comprising EVA having a vinyl acetate content of from about 10-12% w/w with respect to ethylene, and an outer layer comprising EVA having a vinyl acetate content of from about 30% w/w to about 35% w/w with respect to ethylene.

In one example, the core comprises a radio-opaque agent, such as barium sulfate.

In one example, the outer layer comprises the eutectic composition.

In another particularly contemplated embodiment, the device, for example the implant, comprises a core comprising a first polymer comprising EVA having an ethylene content of at least about 25% w/w with respect to vinyl acetate, for example, at least 30% w/w, or at least about 33% w/w, and an outer layer comprising a second polymer comprising EVA having an ethylene content of about 10% w/w to about 20% w/w with respect to vinyl acetate, wherein the core comprises the eutectic composition.

In various embodiments, the device, for example the implant, comprises one or more other components, including one or more other agents, including one or more other active agents. In one embodiment, the eutectic composition comprises one or more other components, including one or more other agents such as one or more other active agents.

In various embodiments, the one or more other agents is an agent capable of aiding location, monitoring, or retrieval of the implant, such as a colouring agent or radio-opaque agent including, for example barium sulphate, a radioactive isotope, or the like, for example to facilitate locating the implant in the body and/or facilitate recovery and/or complete removal of the implant.

In various embodiments, the one or more other agents is an agent capable of aiding identification of the device, for example the implant, such as a colouring agent to, for example, aid visual selection of the device, and/or indicate the identity of the active agent, the dose/concentration of active agent, such as the dosage per linear length of device, for example the dosage per linear length of the implant, the release profile, and the like.

In one example, the one or more other agents is an agent capable of potentiating or prolonging the action of the active agent(s).

In one embodiment, efficacy is achieved by a combination of active agent and one or more other agents, wherein the dosage of active agent is lower than that which would be effective in the absence of the one or more other agents.

In one embodiment, efficacy is achieved by a combination of active agent and one or more other agents, wherein the dosage of active agent is higher than that able to be safely administered in the absence of the one or more other agents, or higher than that necessary to provide at least a degree of efficacy, including efficacy of a different temporal, anatomical, or therapeutic extent.

Specifically contemplated are embodiments in which the one or more active agents remain soluble and/or do not crystallize. For example, the one or more active agents remains soluble and/or does not crystallize, despite being present in the device, for example the implant, at a concentration or in an amount beyond which can be maintained in a molecular dispersion within the polymer in a non-eutectic composition.

For example, the one or more active agents remains soluble and/or does not crystallize, despite being present in the device, for example the implant, at a concentration or in an amount greater than that at which crystallization of the active agent occurs in the presence of the polymer only.

For example, the one or more active agents remains soluble and/or does not crystallize, despite being present in the device, for example the implant, at a concentration or in an amount greater than that at which crystallization occurs in a composition other than the eutectic composition as described herein.

In various embodiments, the one or more active agents is present in the device, for example the implant, at a concentration or amount greater than that which can be maintained in a molecular dispersion of the one or more active agents when present in a composition lacking the fatty acid, fatty alcohol, or fatty amine.

In various embodiments, the analgesic is an anaesthetic, for example, a local anaesthetic.

Examples of specifically contemplated active agents include pilocarpine, progesterone, etonogestrel, etonogestreVethinylestradiol, tetracycline, sirolimus, ganciclovir, morphine, noroxymorphone, bupivacaine, lidocaine, ibuprofen, prilocaine, ropivocaine, and tetracaine, including any combination of two or more thereof.

In one particularly contemplated embodiment, the active agent is an anaesthetic selected from the group comprising prilocaine, tetracaine, bupivacaine, lidocaine, and ropivocaine. For example, the anaesthetic is selected from the group comprising bupivacaine, lidocaine, and ropivacaine.

In one embodiment, where one or more of the active agents is an analgesic, one or more other active agents is also present.

In one example, the one or more other active agents is an agent capable of potentiating or prolonging the action of the analgesic.

In one embodiment, the analgesic efficacy is achieved by a combination of analgesic and one or more other active agents, wherein the dosage of analgesic is lower than that which would be effective in the absence of the one or more other active agents.

In one embodiment, analgesic efficacy is achieved by a combination of analgesic and one or more other active agents, wherein the dosage of analgesic is higher than that able to be safely administered in the absence of the one or more other active agents, or higher than that necessary to provide analgesia of a different temporal, anatomical, or therapeutic extent.

In various embodiments, the one or more other active agents is selected from the group comprising NSAIDS, opiates, inflammatory modulators, wound healing agents, agents which regulate bleeding including anti-coagulants or coagulants, antibiotics, and antivirals.

Accordingly, in various embodiments the device, for example the implant, comprises one or more anaesthetics and one or more other active agents selected from the group comprising NSAIDS, opiates, inflammatory modulators, wound healing agents, agents which regulate bleeding including anti-coagulants or coagulants, antibiotics, and antivirals.

For example, the eutectic composition comprises one or more anaesthetics and one or more other active agents selected from the group comprising NSAIDS, opiates, inflammatory modulators, wound healing agents, agents which regulate bleeding including anti-coagulants or coagulants, antibiotics, and antivirals.

In various embodiments, the device, for example the implant, comprises one or more active agents selected from the group comprising pilocarpine, progesterone, etonogestrel, etonogestrel/ethinylestradiol, tetracycline, sirolimus, ganciclovir, morphine, noroxymorphone, bupivacaine, lidocaine, ibuprofen, prilocaine, ropivocaine, tetracaine, and any combination of two or more thereof, and one or more other active agents selected from the group comprising NSAIDS, opiates, inflammatory modulators, wound healing agents, antibiotics, and antivirals, and any combination of two or more thereof.

For example, the eutectic composition comprises one or more active agents selected from the group comprising pilocarpine, progesterone, etonogestrel, etonogestreVethinylestradiol, tetracycline, sirolimus, ganciclovir, morphine, noroxymorphone, bupivacaine, lidocaine, ibuprofen, prilocaine, ropivocaine, tetracaine, and any combination of two or more thereof, and one or more other active agents selected from the group comprising NSAIDS, opiates, inflammatory modulators, wound healing agents, antibiotics, and antivirals, and any combination of two or more thereof.

In one embodiment the administration is by implantation or insertion, for example, implantation or insertion into an organ, a cavity such as the peritoneal cavity, nasal cavity, or buccal cavity, a blood vessel, spinal column, meninges, or any part of the alimentary canal.

In one embodiment, the administration is by implantation or insertion into a site in contact with a bodily fluid, for example, in contact with blood, peritoneal fluid, gastric fluid, cerebrospinal fluid, or mucosal fluid.

In certain embodiments, implantation or insertion is subcutaneous or intramuscular implantation or insertion. In certain embodiments, implantation or insertion is intraperitoneal, subdermal, or intravenous.

In certain embodiments, implantation or insertion is via intubation, catheterization, plembotomy, laproscopy, surgical port, stent, subcutaneous, thoracotomy, orthoracoscopy.

In one embodiment, implantation or insertion comprises attaching at least one portion of the device to the subject. In one example, implantation or insertion comprises suturing or adhering at least a portion of the device to the subject, for example, suturing one end of the device to the subject's skin, or for example, suturing at least a portion of the device to a subcutaneous layer, such as a muscle, or connective tissue.

In one embodiment, the device comprises an end cap, for example, a T-shaped cap or a circular cap capable of being sutured or adhered to the subject, for example, to maintain the location of at least one end of the implant and/or to facilitate removal, the end cap is sutured to the subject's skin.

In various embodiments, the cap comprises at least one active agent, for example, a different active agent than the remainder of the device.

In various embodiments, the method comprises intraperitoneal administration of a device as contemplated herein, for example a device as contemplated herein comprising one or more analgesics or anaesthetics. In certain embodiments, intraperitoneal administration comprises implantation of the device in the peritoneal cavity, including in some examples affixing, suturing or adhering the device to the subject (for example to facilitate removal of the device).

In certain embodiments, methods of or comprising intraperitoneal administration of a device as contemplated herein are performed in conjunction with one or more other surgical procedures, whether sequentially or contemporaneously. In specifically contemplated embodiments, the intraperitoneal administration of the device targets improved pain relief, and/or reduced reliance on systemic pain relief, such as reduced reliance on or need for systemic opiate administration following intraperitoneal surgery.

In one specifically contemplated embodiment, the invention relates to a method of administering to the peritoneal cavity of a subject in need thereof an effective amount of one or more anaesthetics and/or analgesics, the method comprising administering to the peritoneal cavity of the subject a device comprising a) at least one biocompatible polymer; and b) an eutectic composition comprising a first active agent and one or more of the group comprising i) one or more active agents capable of forming a eutectic composition with the first active agent; or ii) one or more fatty acids; or iii) one or more fatty alcohols; or iv) one or more fatty amines; or v) any combination of i) to iv) above, including any combination of two or more of i) to iv);

wherein the first active agent and/or the one or more active agents capable of forming a eutectic composition with the first active agent is or are an analgesic or an anaesthetic.

In one example, the effective amount of one or more analgesics or anaesthetics is an amount effective to achieve effective pain relief and/or reduced reliance on other analgesia, for example for a day or more following administration. In certain embodiments, the amount is effective to achieve effective pain relief and/or reduce reliance on other analgesia for more than one day following administration, more than two days, more than three days, or for four or more days following administration. In one example, such as when the subject has undergone surgery, the effective amount is sufficient to provide effective pain relief and/or reduced reliance on other analgesia for the duration of their post-operative stay.

In one embodiment, the invention relates to a method of blocking the vagus nerve in a subject in need thereof, the method comprising intraperitoneally administering to the subject a device as herein contemplated, wherein the first active agent and/or the one or more active agents capable of forming a eutectic composition with the first active agent is or are an analgesic or an anaesthetic.

In certain embodiments, the device is administered by topical administration, for example, as a topical bandage, or as or in conjunction with a wound dressing.

In various embodiments, the eutectic composition comprises active agent and the fatty acid, fatty alcohol, and/or fatty amine, in a molar ratio of from about 1:50 to about 50:1.

For example, the eutectic composition comprises active agent and fatty acid in a molar ratio of from about 1:50, about 1:40, about 1:30, about 1:20, about 1:10, about 1:9, about 1:8, about 1:7, about 1:6, about 1:5, about 1:4, about 1:3, about 1:2, about 1:1.5, or about 1:1. In another example, the eutectic composition comprises active agent and fatty acid in a molar ratio of from about 1:50, about 1:40, about 1:30, about 1:20, about 10:1, about 9:1, about 8:1, about 7:1, about 6:1, about 5:1, about 4:1, about 3:1, about 2:1, or about 1.5:1.

In another example, the eutectic composition comprises active agent and fatty alcohol in a molar ratio of from about 1:50, about 1:40, about 1:30, about 1:20, about 1:10, about 1:9, about 1:8, about 1:7, about 1:6, about 1:5, about 1:4, about 1:3, about 1:2, about 1:1.5, or about 1:1. In another example, the eutectic composition comprises active agent and fatty alcohol in a molar ratio of from about 50:1, about 40:1, about 30:1, about 20:1, about 10:1, about 9:1, about 8:1, about 7:1, about 6:1, about 5:1, about 4:1, about 3:1, about 2:1, or about 1.5:1.

In a further example, the eutectic composition comprises active agent and fatty amine in a molar ratio of from about 1:50, about 1:40, about 1:30, about 1:20, about 1:10, about 1:9, about 1:8, about 1:7, about 1:6, about 1:5, about 1:4, about 1:3, about 1:2, about 1:1.5, or about 1:1. In another example, the eutectic composition comprises active agent and fatty amine in a molar ratio of from about 50:1, about 40:1, about 30:1, about 20:1, about 10:1, about 9:1, about 8:1, about 7:1, about 6:1, about 5:1, about 4:1, about 3:1, about 2:1, or about 1.5:1.

In specifically contemplated examples, the eutectic composition comprises analgesic agent and fatty acid in a molar ratio of from about 1:10, about 1:9, about 1:8, about 1:7, about 1:6, about 1:5, about 1:4, about 1:3, about 1:2, about 1:1.5, or about 1:1. In another example, the eutectic composition comprises analgesic agent and fatty acid in a molar ratio of from about 10:1, about 9:1, about 8:1, about 7:1, about 6:1, about 5:1, about 4:1, about 3:1, about 2:1, or about 1.5:1.

Specifically contemplated molar ratios of analgesic agent, for example, of anaesthetic, to fatty acid, fatty alcohol, or fatty amine include about 1:10, about 1:9, about 1:8, about 1:7, about 1:6, about 1:5, about 1:4, about 2:7, about 1:3, about 3:7, about 1:2, about 2:3, about 3:4, about 1:1, about 4:3, about 3:2, about 2:1, about 7:3, about 3:1, about 7:2, about 4:1, about 5:1, about 6:1, about 7:1, about 8:1, about 9:1, or about 10:1.

In embodiments wherein the eutectic comprises one or more fatty acids, it will be appreciated that in certain examples two or more, three or more, four or more, or more than four different fatty acids are present. In certain examples, five or more, six or more, seven or more, eight or more, nine or more, ten or more than ten different fatty acids are present.

In certain embodiments, the one or more fatty acids are selected from the group comprising myristic acid, oleic acid, stearic acid, palmitic acid, lauric acid, linoleic acid, capric acid, tridecyclic acid, glycerol monostearate, and any combination of two or more thereof. Particularly contemplated examples include compositions comprising a fatty acid selected from the group comprising myristic acid, oleic acid, stearic acid, and any combination of two or more thereof. Further particularly contemplated examples include compositions comprising a fatty acid selected from myristic acid, stearic acid, and/or palmitic acid, together with a short chain fatty acid, such as but not limited to oleic acid or lauric acid.

In various examples, the molar ratio of myristic acid, stearic acid, or palmitic acid, to short chain fatty acid, for example, to oleic acid or lauric acid, is about 1:10, about 1:9, about 1:8, about 1:7, about 1:6, about 1:5, about 1:4, about 2:7, about 1:3, about 3:7, about 1:2, about 2:3, about 3:4, about 1:1, about 4:3, about 3:2, about 2:1, about 7:3, about 3:1, about 7:2, about 4:1, about 5:1, about 6:1, about 7:1, about 8:1, about 9:1, or about 10:1.

In one example, the eutectic composition comprises myristic acid. In one example, the eutectic composition comprises myristic acid together with a short chain fatty acid, including but not limited to oleic acid or lauric acid. In various particularly contemplated examples, the molar ratio of myristic acid to short chain fatty acid, for example, to oleic acid, is about 1:10, about 1:9, about 1:8, about 1:7, about 1:6, about 1:5, about 1:4, about 2:7, about 1:3, about 3:7, about 1:2, about 2:3, about 3:4, about 1:1, about 4:3, about 3:2, about 2:1, about 7:3, about 3:1, about 7:2, about 4:1, about 5:1, about 6:1, about 7:1, about 8:1, about 9:1, or about 10:1.

In various embodiments, the device, for example the implant, comprises from about 10% w/w polymer to about 99% w/w polymer. For example, the device, for example the implant, comprises from about 10% w/w polymer to about 98% w/w polymer, from about 10% w/w polymer to about 95% w/w polymer, from about 10% w/w polymer to about 90% w/w polymer, from about 10% w/w polymer to about 80% w/w polymer, from about 10% w/w polymer to about 75% w/w polymer, from about 10% w/w polymer to about 70% w/w polymer, from about 10% w/w polymer to about 65% w/w polymer, from about 10% w/w polymer to about 60% w/w polymer, from about 10% w/w polymer to about 55% w/w polymer, from about 10% w/w polymer to about 50% w/w polymer, from about 10% w/w polymer to about 45% w/w polymer, from about 10% w/w polymer to about 40% w/w polymer, from about 10% w/w polymer to about 35% w/w polymer, from about 10% w/w polymer to about 30% w/w polymer, from about 10% w/w polymer to about 25% w/w polymer, or from about 10% w/w polymer to about 20% w/w polymer. In certain particularly contemplated examples, the device, for example the implant, comprises from about 15% w/w polymer to about 75% w/w polymer, from about 20% w/w polymer to about 75% w/w polymer, from about 25% w/w polymer to about 75% w/w polymer, from about 30% w/w polymer to about 75% w/w polymer, from about 35% w/w polymer to about 75% w/w polymer, from about 40% w/w polymer to about 75% w/w polymer, from about 45% w/w polymer to about 75% w/w polymer, from about 50% w/w polymer to about 75% w/w polymer, from about 55% w/w polymer to about 75% w/w polymer, from about 60% w/w polymer to about 75% w/w polymer, or from about 65% w/w polymer to about 75% w/w polymer.

In further embodiments, the device, for example the implant, comprises at least about 10% w/w polymer, at least about 15% w/w polymer, at least about 20% w/w polymer, at least about 25% w/w polymer, at least about 30% w/w polymer, at least about 35% w/w polymer, at least about 40% w/w polymer, at least about 45% w/w polymer, at least about 50% w/w polymer, at least about 55% w/w polymer, at least about 60% w/w polymer, at least about 65% w/w polymer, at least about 70% w/w polymer, at least about 75% w/w polymer, at least about 80% w/w polymer, at least about 85% w/w polymer, at least about 90% w/w polymer, at least about 95% w/w polymer, or at least about 98% w/w polymer.

In further particularly contemplated embodiments, the device, for example the implant, comprises at least about 30% w/w polymer, at least about 35% w/w polymer, at least about 40% w/w polymer, at least about 45% w/w polymer, at least about 50% w/w polymer, at least about 55% w/w polymer, at least about 60% w/w polymer, at least about 65% w/w polymer, at least about 70% w/w polymer, at least about 75% w/w polymer, or at least about 80% w/w polymer.

For example, the device, for example the implant, comprises at least about 40% w/w polymer.

In various embodiments, the device, for example the implant, consists essentially of, or consists of a) at least one biocompatible polymer; and
b) an eutectic composition comprising a first active agent and one or more of the group comprising
   i) one or more active agents capable of forming a eutectic composition with the first active agent; or
   ii) one or more fatty acids; or
   iii) one or more fatty alcohols; or
   iv) one or more fatty amines; or
   v) any combination of i) to iv) above, including any combination of two or more of i) to iv).

Accordingly, in certain embodiments, the device, for example the implant, consists of polymer, such as polymer in a w/w concentration as specified above, with substantially the remainder of the device, for example the implant, consisting of eutectic composition as described above.

In various embodiments, the device, for example the implant, comprises from about 0.1% w/w eutectic composition to about 70% w/w eutectic composition, for example, the device, for example the implant, comprises from about 0.1% w/w eutectic composition to about 65% w/w eutectic composition, from about 0.1% w/w eutectic composition to about 60% w/w eutectic composition, from about 0.1% w/w eutectic composition to about 55% w/w eutectic composition, from about 0.1% w/w eutectic composition to about 50% w/w eutectic composition.

In various embodiments, the device, for example the implant, comprises from about 1% w/w eutectic composition to about 70% w/w eutectic composition. For example, the device, for example the implant, comprises from about 2% w/w eutectic composition to about 70% w/w eutectic composition, from about 3% w/w eutectic composition to about 4% w/w eutectic composition, from about 5% w/w eutectic composition to about 70% w/w eutectic composition, from about 6% w/w eutectic composition to about 70% w/w eutectic composition, from about 7% w/w eutectic composition to about 70% w/w eutectic composition, from about 8% w/w eutectic composition to about 70% w/w eutectic composition, from about 9% w/w eutectic composition to about 70% w/w eutectic composition, from about 10% w/w eutectic composition to about 70% w/w eutectic composition, from about 10% w/w eutectic composition to about 65% w/w eutectic composition, from about 10% w/w eutectic composition to about 60% w/w eutectic composition, from about 10% w/w eutectic composition to about 55% w/w eutectic composition, from about 10% w/w eutectic composition to about 50% w/w eutectic composition, from about 10% w/w eutectic composition to about 45% w/w eutectic composition, from about 10% w/w eutectic composition to about 40% w/w eutectic composition, from about 10% w/w eutectic composition to about 35% w/w eutectic composition, from about 10% w/w eutectic composition to about 30% w/w eutectic composition, from about 10% w/w eutectic composition to about 25% w/w eutectic composition, or from about 10% w/w eutectic composition to about 20% w/w eutectic composition.

In certain particularly contemplated examples, the device, for example the implant, comprises from about 15% w/w eutectic composition to about 70% w/w eutectic composition, from about 20% w/w eutectic composition to about 70% w/w eutectic composition, from about 25% w/w eutectic composition to about 70% w/w eutectic composition, from about 30% w/w eutectic composition to about 70% w/w eutectic composition, from about 35% w/w eutectic composition to about 70% w/w eutectic composition, from about 40% w/w eutectic composition to about 70% w/w eutectic composition, from about 45% w/w eutectic composition to about 70% w/w eutectic composition, from about 50% w/w eutectic composition to about 70% w/w eutectic composition, from about 55% w/w eutectic composition to about 70% w/w eutectic composition, from about 60% w/w eutectic composition to about 70% w/w eutectic composition, or from about 65% w/w eutectic composition to about 70% w/w eutectic composition.

In further embodiments, the device, for example the implant, comprises at least about 10% w/w eutectic composition, at least about 15% w/w eutectic composition, at least about 20% w/w eutectic composition, at least about 25% w/w eutectic composition, at least about 30% w/w eutectic composition, at least about 35% w/w eutectic composition, at least about 40% w/w eutectic composition, at least about 45% w/w eutectic composition, at least about 50% w/w eutectic composition, at least about 55% w/w eutectic composition, at least about 60% w/w eutectic composition, at least about 65% w/w eutectic composition, or at least about 70% w/w eutectic composition.

Without wishing to be bound by any theory, the applicants believe that the desired or required mechanical properties of the device, such as an implant, will generally be the limiting factor with respect to the ratio of eutectic composition to polymer present in the device. As described above, specifically contemplated devices comprising up to about 70% w/w eutectic composition and about 30% polymer are contemplated.

In further embodiments, the device, for example the implant, consists essentially of, or consists of at least about 10% w/w eutectic composition, at least about 15% w/w eutectic composition, at least about 20% w/w eutectic composition, at least about 25% w/w eutectic composition, at least about 30% w/w eutectic composition, at least about 35% w/w eutectic composition, at least about 40% w/w eutectic composition, at least about 45% w/w eutectic composition, at least about 50% w/w eutectic composition, at least about 55% w/w eutectic composition, at least about 60% w/w eutectic composition, at least about 65% w/w eutectic composition, or at least about 70% w/w eutectic composition, with the remainder of the device comprising polymer. For example, the device consists essentially of, or consists of about 30% w/w eutectic composition and about 70% w/w polymer, about 35% w/w eutectic composition and about 65% w/w polymer, about 40% w/w eutectic composition and about 60% w/w polymer, about 45% w/w eutectic composition and about 55% w/w polymer, about 50% w/w eutectic composition and about 50% w/w polymer, about 55% w/w eutectic composition and about 45% w/w polymer, about 60% w/w eutectic composition and about 40% w/w polymer, about 65% w/w eutectic composition and about 35% w/w polymer, or about 70% w/w eutectic composition and about 30% w/w polymer.

For example, as exemplified herein (see for example Table 7), when one embodiment of a device comprising a 1:1 molar ratio eutectic composition of lidocaine with myristic acid was formed with EVA polymer, the eutectic composition formed approximately 40% w/w of the device (i.e., the lidocaine concentration was 20% w/w of the device, and the myristic acid was 20% w/w), with EVA (33% VA) was around 60% w/w of the device. Still higher euctectic: polymer ratios are contemplated, such as 25% lidocaine (w/w of the device):25% myristic acid (w/w of the device): 50% EVA (30% VA), or 30% lidocaine (w/w of the device): 30% myristic acid (w/w of the device):40% EVA (30% VA), or 35% lidocaine (w/w of the device):35% myristic acid (w/w of the device):30% EVA (30% VA).

In certain embodiments, the eutectic composition consists essentially of, or consists of the one or more active agents and one or more of the group comprising i) one or more fatty acids;
ii) one or more fatty alcohols;
iii) one or more fatty amines;
iv) any combination of i) to iii) above, including any combination of two or more of i) to iii).

In various embodiments, the eutectic composition comprises at least about 0.1% w/w active agent, for example, at least about 1% w/w active agent, at least about 2% w/w active agent, at least about 3% w/w active agent, at least about 4% w/w active agent, at least about 5% w/w active agent, at least about 6% w/w active agent, at least about 7% w/w active agent, at least about 8% w/w active agent, at least about 9% w/w active agent, or at least about 10% w/w active agent.

In various embodiments, the eutectic composition comprises at least about 15% w/w active agent, at least about 20% w/w/active agent, at least about 25% w/w active agent, at least about 30% w/w active agent, or more than 30% w/w active agent.

In certain embodiments, the eutectic composition comprises more than 35% w/w active agent, for example 40% w/w active agent or more, 50% w/w active agent or more, 60% w/w active agent or more, 70% w/w active agent or more, 80% w/w active agent or more, 90% w/w active agent or more, or 95% w/w active agent or more.

It will be appreciated that in order to minimize the physical size of the device, for example the implant, in certain embodiments there is benefit in increasing or maximizing active agent loading, such that the amount of active agent in the device, for example the implant, comprises, for example, at least about 15% w/w of the device, for example at least about 15% w/w of the implant. For example, in certain embodiments, including for example embodiments for the administration of one or more anaesthetics such as lidocaine, the active agent comprises at least about 17.5% w/w of the implant, at least about 20% w/w of the implant, at least about 22.5% w/w, at least about 25% w/w, at least about 27.5% w/w, or at least about 30% w/w of the implant.

In certain embodiments, including for example embodiments for the administration of one or more anaesthetics such as lidocaine, the active agent comprises at least about 15% w/w of one polymeric composition comprising the implant, such as an inner core of the implant, or an intermediate layer of the implant, or an outer layer of the implant. In certain embodiments, the active agent comprises at least about 17.5% w/w, at least about 20% w/w of the implant, at least about 22.5% w/w, at least about 25% w/w, at least about 27.5% w/w, or at least about 30% w/w of one polymeric composition comprising the implant.

In certain examples, the implant comprises more than one polymeric composition, including, for example, one polymeric composition with one active agent or one concentration of active agent, and at least one other polymeric composition with no active agent, or with another active agent, or with another concentration of active agent.

In particularly contemplated embodiments, such as embodiments comprising one or more anaesthetics, the implant has a cross-sectional dimension and or configuration to allow delivery or implantation via a surgical port.

In particularly contemplated embodiments, such as embodiments comprising one or more anaesthetics, the implant has a cross-sectional diameter of about 5 mm.

In certain embodiments, at least one polymeric composition comprising the implant comprises at least about 20% w/w anaesthetic.

In certain embodiments, the implant has a cross-sectional diameter of about 5 mm. Specifically contemplated is an implant comprising at least one polymeric composition comprising at least about 20% w/w anaesthetic, wherein the implant has a substantially circular cross-section with a diameter of about 5 mm or less such that said implant being administrable via a surgical port, wherein the concentration of anaesthetic is substantially uniform along the length of the implant, and wherein an appropriate dosage can readily be determined by the length of implant administered.

In one specific example, the implant comprises a core comprising a first polymeric composition, and a second polymeric composition, wherein the second polymeric composition comprises at least about 20% w/w lidocaine, wherein the first and second polymeric compositions are present in a ratio such that the total concentration of lidocaine is from about 10% w/w to about 15% w/w of the implant.

In various embodiments, the eutectic composition consists essentially of, or consists of one or more active agents and one or more fatty acids.

In one embodiment, the eutectic composition comprises, consists essentially of, or consists of one or more anaesthetics and one or more fatty acids. In various examples, the eutectic composition comprises, consists essentially of, or consists of one or more of prilocaine, tetracaine, bupivacaine, lidocaine, and ropivocaine and one or more fatty acids.

In various examples, the eutectic composition comprises, consists essentially of, or consists of one or more anaesthetics and one or more fatty acids selected from the group comprising myristic acid, oleic acid, stearic acid, palmitic acid, lauric acid, and any combination of two or more thereof.

Specifically contemplated molar ratios of anaesthetic to fatty acid include about 1:10, about 1:9, about 1:8, about 1:7, about 1:6, about 1:5, about 1:4, about 2:7, about 1:3, about 3:7, about 1:2, about 2:3, about 3:4, about 1:1, about 4:3, about 3:2, about 2:1, about 7:3, about 3:1, about 7:2, about 4:1, about 5:1, about 6:1, about 7:1, about 8:1, about 9:1, or about 10:1.

In one embodiment, the eutectic composition comprises lidocaine and myristic acid. In one example, in a eutectic composition comprising lidocaine and myristic acid, the lidocaine and myristic acid are present at a molar ratio of from about 2:1 to about 1:2, for example at a molar ratio of about 1:1. In one embodiment, the eutectic composition is formulated with EVA. In one embodiment, the eutectic composition is formulated with polycaprolactone. In various embodiments, the eutectic composition or the eutectic:polycaprolactone composition has a composition as depicted in Table 27 herein. In a specifically contemplated embodiment, the device comprises a eutectic composition comprises lidocaine and myristic acid at a molar ratio of from about 2:1 to about 1:2, for example at a molar ratio of about 1:1, and the device comprises EVA (33% VA).

In particularly contemplated embodiments, the device, for example the implant, comprises, consists essentially of, or consists of EVA, such as EVA (30% VA), and at least about 9% w/w lidocaine, said lidocaine present in a eutectic composition with myristic acid. In further examples, the device comprises, consists essentially of, or consists of EVA, such as EVA (30% VA), and at least about 10% w/w lidocaine, said lidocaine present in a eutectic composition with myristic acid, at least about 11% w/w lidocaine, at least about 12% w/w lidocaine, at least about 13% w/w lidocaine, at least about 14% w/w lidocaine, at least about 15% w/w lidocaine, at least about 16% w/w lidocaine, at least about 17% w/w lidocaine, at least about 18% w/w lidocaine, at least about 19% w/w lidocaine, at least about 20% w/w lidocaine, at least about 21% w/w lidocaine, at least about 22% w/w lidocaine, at least about 23% w/w lidocaine, at least about 24% w/w lidocaine, at least about 25% w/w lidocaine, at least about 30% w/w lidocaine, or at least about 35% w/w lidocaine, said lidocaine present in a eutectic composition with myristic acid.

Devices having the w/w loading of anaesthetic as described above for lidocaine, but in which the lidocaine is substituted for one or more of prilocaine, tetracaine, bupivacaine, and ropivocaine, or any combination thereof including combinations thereof with lidocaine, are specifically contemplated as if individually set forth. Further, such devices, including those comprising lidocaine, as described above, in which the myristic acid is substituted for oleic acid, stearic acid, palmitic acid, lauric acid, and any combination of two or more thereof including combinations thereof with myristic acid, are also specifically contemplated as if individually set forth.

For example, in one embodiment, the eutectic composition comprises lidocaine and stearic acid. In one example, in a eutectic composition comprising lidocaine and stearic acid, the lidocaine and stearic acid are present at a molar ratio of from about 5:1:to about 1:1, for example at a molar ratio of from about 4:1:to about 1:1, at a molar ratio of about 2:1, or at a molar ratio of 1:0.47. In one embodiment, the eutectic composition is formulated with EVA.

In one embodiment, the eutectic composition comprises lidocaine and glycerol monostearate. In one example, in a eutectic composition comprising lidocaine and glycerol monostearate, the lidocaine and glycerol monostearate are present at a molar ratio of from about 3:1 to about 4:3, for example at a molar ratio of about 3:2.

In one embodiment, the eutectic composition comprises lidocaine and palmitic acid. In one example, in a eutectic composition comprising lidocaine and palmitic acid, the lidocaine and palmitic acid are present at a molar ratio of from about 2:1 to about 1:2, for example at a molar ratio of about 3:2. In one particular example, the molar percentage of lidocaine in the composition is about 58%, for example about 58.3%. In one embodiment, the eutectic composition is formulated with EVA.

In another example, the eutectic composition comprises lidocaine, palmitic acid, and oleic acid. In one example, the eutectic composition comprises lidocaine, palmitic acid, and oleic acid in a 22:13:5 ratio. In one embodiment, the eutectic composition is formulated with EVA, for example, with EVA in a 3:2 w/w ratio.

In one embodiment, the eutectic composition comprises bupivacaine and myristic acid. In one example, in a eutectic composition comprising bupivacaine and myristic acid, the bupivacaine and myristic acid are present at a molar ratio of from about 2:1 to about 1:2, for example at a molar ratio of about 2:3. In one embodiment, the eutectic composition is formulated with EVA.

In another example, the eutectic composition comprises bupivacaine, myristic acid, and oleic acid. In one example, the eutectic composition comprises bupivacaine, myristic acid, and oleic acid in a 40:60:5 ratio. In one embodiment, the eutectic composition is formulated with EVA. In various embodiments, the eutectic composition or the eutectic:EVA composition has a composition as depicted in Table 25 herein, or as depicted in Table 7 herein, or as depicted in Table 9 herein.

In another example, the eutectic composition comprises bupivacaine, myristic acid, and lauric acid. In one example, the eutectic composition comprises bupivacaine, myristic acid, and lauric acid in a 40:60:5 ratio. In one embodiment, the eutectic composition is formulated with EVA. In various embodiments, the eutectic composition or the eutectic:EVA composition has a composition as depicted in Table 25 herein, or as depicted in Table 7 herein, or as depicted in Table 9 herein.

In one embodiment, the eutectic composition comprises ropivacaine and myristic acid. In one example, in a eutectic composition comprising ropivacaine and myristic acid, the ropivacaine and myristic acid are present at a molar ratio of from about 3:1 to about 1:4, for example at a molar ratio of about 1:3.

In one embodiment, the eutectic composition comprises ropivacaine and palmitic acid. In one example, in a eutectic composition comprising ropivacaine and palmitic acid, the ropivacaine and palmitic acid are present at a molar ratio of from about 3:1 to about 1:4, for example at a molar ratio of about 1:3.

In one embodiment, the eutectic composition comprises ibuprofen and palmitic acid. In one example, in a eutectic composition comprising ibuprofen and palmitic acid, the ibuprofen and palmitic acid are present at a molar ratio of from about 3:1 to about 1:3, from about 2:1 to about 1:2, for example at a molar ratio of about 1:1.

In one embodiment, the device, for example the implant, comprises a single layer, for example a substantially homogenous distribution of eutectic composition within a polymer.

It will be appreciated by those skilled in the art on reading this disclosure, including the disclosure relating to the embodiments exemplified herein in the Examples, that the device, for example the implant, may comprise more than one layer, for example, an inner layer or core, such as an inner core of a first polymer or blend of polymers, active agent(s) and/or eutectic, and an outer layer having a different composition, for example, a different polymer or blend of polymers, or a different active agent, mixture of active agents, or composition of active agents, polymers, or eutectic(s).

It will likewise be appreciated that devices comprising more than 2 layers are specifically contemplated, wherein each layer is the same or different.

In one specifically contemplated example, the device, for example the implant, comprises an inner layer or core of a first composition, such as a first polymer or blend of polymers, and an outer, active agent-eluting layer comprising the or a eutectic composition as herein described.

In another specifically contemplated example, the device, for example the implant, comprises an inner, active agent-eluting layer or core comprising the or a eutectic composition as herein described, and an outer layer having a different composition, for example, the at least one polymer or a blend of polymers.

In certain embodiments, the outer layer is an active agent-permeable layer.

In another aspect, the invention relates to a method of manufacturing a device as herein described, the method comprising providing a eutectic mixture comprising a first active agent and one or more of the group comprising

- i) one or more active agents capable of forming a eutectic composition with the first active agent; or
- ii) one or more fatty acids; or
- iii) one or more fatty alcohols; or
- iv) one or more fatty amines; or
- v) any combination of i) to iv) above, including any combination of two or more of i) to iv);

and admixing said eutectic composition with one or more biocompatible polymers to form the device.

In various embodiments, the admixing and/or forming comprises extrusion such as hot melt extrusion, molding such as injection molding, additive manufacture, or electrospinning.

In certain embodiments, the device, for example the implant, is a sustained release device, for example a sustained release implant, wherein the rate of active agent release is prolonged with only a portion of the total active agent present in the device released per unit of time.

In one embodiment a sustained release implant is provided that is suitable for administration to provide sustained or controlled and long-lasting in vivo release of active agent over more than one day. The implant will in certain embodiments deliver, for example, not more than 50%, for example, not more than 25%, of the total active agent present in the implant in about 12 or 24 hours at a physiological pH. In certain embodiments, the implant delivers sustained release of the one or more active agents for more than a day, for example, for 3 or more days, for example, for 5 or more days, for 7 or more days, or for 10 days or more.

In certain particularly contemplated embodiments, the implant comprises one or more anaesthetics, such as lidocaine, and delivers sustained release of the one or more anaesthetics for 3 or more days, for example, for 5 or more days, for 7 or more days, or for 10 days or more.

In one particularly contemplated example, the implant comprises from about 2 to about 4 g lidocaine, and sustains release of said lidocaine for 7 or more days, for example for 10 or more days. In one example, the implant comprises about 2.4 g lidocaine, and sustains release of said lidocaine for 10 days or more.

In a further aspect, the invention relates to a device comprising

- a) at least one biocompatible polymer; and
- b) an eutectic composition comprising a first active agent and one or more of the group comprising
  - i) one or more active agents capable of forming a eutectic composition with the first active agent; or
  - ii) one or more fatty acids; or
  - iii) one or more fatty alcohols; or
  - iv) one or more fatty amines; or
  - v) any combination of i) to iv) above, including any combination of two or more of i) to iv);

wherein the first active agent and/or one or more active agents is present in a therapeutically effective amount, wherein the device is for use as a medicament.

In a further aspect, the invention relates to a device for the manufacture of a medicament for the treatment of a disease or disorder, the device comprising

- a) at least one biocompatible polymer; and
- b) an eutectic composition comprising a first active agent and one or more of the group comprising i) one or more active agents capable of forming a eutectic composition with the first active agent; or
ii) one or more fatty acids; or
iii) one or more fatty alcohols; or
iv) one or more fatty amines; or
v) any combination of i) to iv) above, including any combination of two or more of i) to iv);

wherein the first active agent and/or one or more active agents is present in a therapeutically effective amount.

In one aspect, the invention relates to a method of contacting a biological fluid with one or more active agents, the method comprising a) providing a device comprising
   i) at least one biocompatible polymer; and
   ii) an eutectic composition comprising a first active agent and one or more of the group comprising
      A) one or more active agents capable of forming a eutectic composition with the first active agent; or
      B) one or more fatty acids; or
      C) one or more fatty alcohols; or
      D) one or more fatty amines; or
      E) any combination of A) to D) above, including any combination of two or more of A) to D);
b) providing one or more biological fluids; and
c) contacting the biological fluid with the device.

In one embodiment, the method is performed in vivo. In another embodiment, the method is performed ex vivo.

In one embodiment, the method comprises the additional step of assessing one or more pharmacokinetic characteristics of the device, the fluid, and/or the one or more active agents.

In one embodiment, the method comprises the step of assessing the release rate of one or more of the one or more active agents.

In one embodiment, the biological fluid is a bodily fluid, for example, a mammalian bodily fluid.

In various embodiments, the bodily fluid is selected from the group comprising blood, peritoneal fluid, gastric fluid, cerebrospinal fluid, and mucosal fluid.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7). These are only examples of what is specifically intended and all possible combinations of numerical values between the lowest value and the highest value enumerated are to be considered to be expressly stated in this application in a similar manner.

Other objects, aspects, features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The invention is exemplified in the following non limiting embodiments and with reference to the accompanying figures.

DETAILED DESCRIPTION OF THE INVENTION

Figure 1:
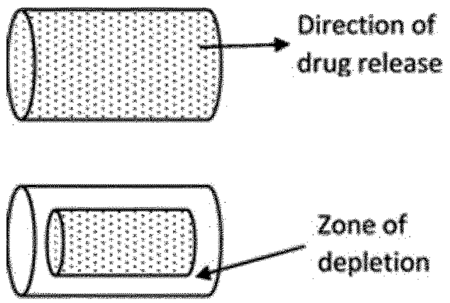
FIG. 1 shows drug release from an insoluble polymer matrix

The present invention relates to devices comprising one or more polymers, including for example implants comprising one or more polymers, for the administration of one or more active agents, including therapeutic agents, and to methods of manufacturing and using said devices.

The devices comprise one or more biocompatible polymers together with a eutectic mixture comprising one or more active agents, and are suitable for administration to, for example, via implantation or insertion into, a subject in need thereof. The devices provide one or more therapeutic or convenience benefits, such as maintained and/or stable drug concentration in a subject to whom they are administered, ready implantation and/or recovery, or a minimisation of surgical intervention, for example by reducing the number of drug administrations a given subject need undergo.

Those skilled in the art will recognise that the polymeric composition of the device, for example the implant, enables a wide variety of shapes to be made. For example, the implant may take any physical form suitable for implantation or insertion in the subject. Particularly contemplated are elongate implants enabling easy implantation and placement within the subject, and recovery from the subject. Examples of such implants are exemplified herein in the Examples.

Those skilled in the art will, on reading this disclosure, likewise recognise that the devices, including the implants, described herein are amenable for use in the delivery of any active agent or combination of active agent to a subject in need thereof.

As used herein, an "active agent" includes an agent capable of eliciting a therapeutic or biological response, for example, is capable of providing or modulating a therapeutic benefit, or of stimulating a biological response in a subject, or in one or more cells, tissues, or organs. Particularly contemplated active agents are those having therapeutic activity, such as one or more drugs, or those capable of modulating, modifying or extending the activity of one or more active agents. Without limitation, in certain examples contemplated herein, an active agent is a protein or polypeptide, a lipid, a polysaccharide, a nucleic acid, a chemokine, a vitamin, a hormone, a metabolite, a growth factor, a cytokine, an exosome, or the like. Particularly contemplated active agents are those that elicit or mediate a biological response, for example, a therapeutic response, including eliciting or modulating one or more of pain relief, one or more immune responses, tissue repair, wound healing and/or tissue regeneration, angiogenesis, hematopoeisis, protein expression, induction, or deposition, cellular proliferation or differentiation, cellular regulation including cell cycle regulation, apoptosis, or modulation of tumourigenesis.

Particularly contemplated active agents for use in the devices and methods described herein include pilocarpine, progesterone, etonogestrel, etonogestreVethinylestradiol, tetracycline, sirolimus, ganciclovir, morphine, noroxymorphone, bupivacaine, lidocaine, ibuprofen, prilocaine, ropivocaine, and tetracaine, including any combination of two or more thereof.

Particularly contemplated active agents for use in the devices and methods described herein include analgesics and anaesthetics. In one particularly contemplated embodiment, the anaesthetic is selected from the group comprising prilocaine, tetracaine, bupivacaine, lidocaine, and ropivocaine. For example, the anaesthetic is selected from the group comprising bupivacaine, lidocaine, and ropivacaine.

Other active agents or combinations thereof include other analgesics or anaesthetics including general/systemic anaesthetics, chemotherapeutics, NSAIDS, opiates, inflammatory modulators, wound healing agents, agents which regulate bleeding including anti-coagulants or coagulants, antibiotics, and antivirals.

Various aspects of the invention are described in further detail in the following subsections. Unless otherwise defined, all technical and scientific terms used herein have the same meaning as is commonly understood by one of ordinary skill in the art to which this invention belongs. In case of conflict, the meaning apparent from the present specification, including definitions, will prevail. Although methods and materials similar or equivalent to those described herein can be used in the practice of the invention, examples of suitable methods and materials are described below. The materials, methods, and examples described herein are illustrative only and are not intended to be limiting.

Those skilled in the art will appreciate the meaning of various terms of degree used herein. For example, as used herein in the context of referring to an amount (e.g., "about 9%"), the term "about" represents an amount close to and including the stated amount that still performs a desired function or achieves a desired result, e.g. "about 9%" can include 9% and amounts close to 9% that still perform a desired function or achieve a desired result. For example, the term "about" can refer to an amount that is within less than 10% of, within less than 5% of, within less than 1% of, within less than 0.1% of, or within less than 0.01% of the stated amount. It is also intended that where the term "about" is used, for example with reference to a figure, concentration, amount, integer or value, the exact figure, concentration, amount, integer or value is also specifically contemplated.

Biocompatible Polymers

Suitable polymeric materials or compositions for use in the device are those which are compatible with the physical and physiological environment in which they are to be used, for example so as to cause no substantial interference with the functioning or physiology of the insertion or implantation site, or with the health or wellbeing of the subject overall. Such materials are considered biocompatible. Such materials can be at least partially or fully biodegradable.

In various embodiments, the at least one biocompatible polymer is selected from the group comprising poly ethylene-vinyl-acetate (EVA), vinyl acetate, silicone, polycaprolactone, polylacticco-glycolic acid (PLGA), polylactic acid (PLA) and polyglycolic acid. In specific examples, the polymer is EVA.

In certain embodiments, for example embodiments in which the implantation of the implant is temporary, but nevertheless may be of significant duration, the polymer is or comprises a non-biodegradable polymer, and/or the implant is substantially non-degradable over the duration (including the expected duration) of implantation.

In certain embodiments, the device, for example the implant, comprises a biocompatible, non-degradable or non-erodible polymer that exhibits generally linear in vivo release kinetics for a wide variety of active ingredients. As used herein, "non-erodible" or "non-biodegradable" polymer refers to a polymer that is resistant to chemical and/or physical destruction by the environment of use (the body of a subject), such that the device, for example the implant, remains essentially intact throughout the release period and/or implantation period. In this instance, "intact" means that the device, for example the implant, retains its physical properties and structural integrity for the duration of use in the use environment, remains stable and retains full functionality after extended time in storage before use, and does not crumble or fragment during use. EVA and silicone are two representative polymer materials used in devices, for example in implants, as described herein. These polymers possess all of the properties mentioned above and are familiar to regulatory agencies such as the FDA.

A specifically contemplated polymer for use in devices, such as implants, as described herein is poly ethylene-vinyl-acetate (EVA). EVA consists of ethylene and vinyl acetate (VA) components. The physical properties of EVA depend upon the proportions of these two components, with the polymer varying from crystalline to rubbery forms. When the VA composition of the ethylene chain increases, the amorphous state of EVA increases which then deceases the overall rigidity of the polymer. It will be appreciated therefore that varying the proportion of ethylene and vinyl acetate is one manner by which the physical and release properties of the implant, for example, the tensile strength, hardness, rigidity/flexibility, permeability, and the like, can be manipulated.

Specific examples of non-degradable implants comprising EVA are exemplified herein, wherein the implant is intended for ready location and removal after a period of implantation, such as a therapeutically effective period of implantation.

Other non-erodible materials may be used, for example, silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, cross-linked poly(ethylene oxide), poly(alkylenes), poly(vinyl imidazole), poly(esters), poly(ethylene terephthalate), polyphosphazenes, and chlorosulphonated polyolefines, and combinations thereof. Biopolymers such as collagen may also be incorporated into devices contemplated herein.

In other embodiments, for example embodiments in which recovery of the device, such as an implant, is not anticipated or is not desirable, the polymer is or comprises a biodegradable polymer, and/or the implant is substantially biodegradable over the duration (including the expected duration) of implantation.

The term "biodegradable polymer" refers to a polymer or polymers which degrade in vivo, and wherein erosion of the polymer or polymers over time occurs concurrent with and/or subsequent to the release of a therapeutic agent. A biodegradable polymer may be a homopolymer, a copolymer, or a polymer comprising more than two polymeric units. In some embodiments, a "biodegradable polymer" may include a mixture of two or more homopolymers or copolymers.

Specifically contemplated examples of suitable polymeric materials for the polymer implant are polyesters. For example, polymers of D-lactic acid, L-lactic acid, racemic lactic acid, glycolic acid, polycaprolactone, and combinations thereof may be used for the polymer implant. In some embodiments, a polyester, if used, may be a homopolymer, a copolymer, or a mixture thereof.

In some devices, and particularly in biodegradable implants, copolymers of glycolic acid and lactic acid are used, where the rate of biodegradation can be controlled, in part, by the ratio of glycolic acid to lactic acid. The molar percentage (% mol) of polylactic acid in the polylactic acid polyglycolic acid (PLGA) copolymer will in certain examples be between 15 mol % and about 85 mol %. In some embodiments, the molar percentage of polylactic acid in the (PLGA) copolymer is between about 35 mol % and about 65 mol %. In some embodiments, a PLGA copolymer with 50 mol % polylactic acid and 50 mol % polyglycolic acid is used in the implant.

The polymers making up the device may also be selected based on their molecular weight.

Different molecular weights of the same or different polymeric compositions may be included in the implant, for example to modulate the release profile, or to provide one or more desired physical characteristics, such as desired tensile strength, desired flexibility or rigidity, and the like.

In some embodiments, the release profile of the active agent, such as the one or more therapeutic agents, or when biodegradable the degradation of the polymer, is affected by the molecular weight of one or more polymers in the polymer matrix. In some embodiments, the molecular weight of one or more of the polymer components, such as a poly (D,L-lactide) component, is advantageously selected to control the release of the therapeutic agent, or one or more physical characteristics, and/or the degradation of the polymer.

According to some embodiments, the average molecular weight (Mw) of a polymer, such as EVA, PLA, or poly (D,L-lactide), may be "low." According to some embodiments, the average molecular weight of a polymer, such as EVA, PLA, or poly (D,L-lactide), may be "medium." According to some embodiments, only low molecular weight polymer, such as EVA, PGA, or poly(D,L-lactide), is included in the implant. According to some embodiments, high molecular weight EVA, PLA, or poly(D,L-lactide)s are not present in implant, or they are only present in a negligible amount (such as about 0.1% by weight of an implant, based on the total weight of the implant). In certain embodiments, particularly those targeting rapid biodegradation, by limiting the amount of high molecular weight polymer present in an implant, the duration of implant degradation is shortened.

Eutectic Compositions

In specifically contemplated examples of the devices described herein, a eutectic composition comprising one or more active agents and an amphipathic component is included. It is believed, without wishing to be bound by any theory, that one or more amphipathic components present in the eutectic composition is at least in part responsible for the improved stability of the drug-delivery embodiments provided herein, and/or at least in part responsible for advantageous drug release kinetics.

Figure 2:
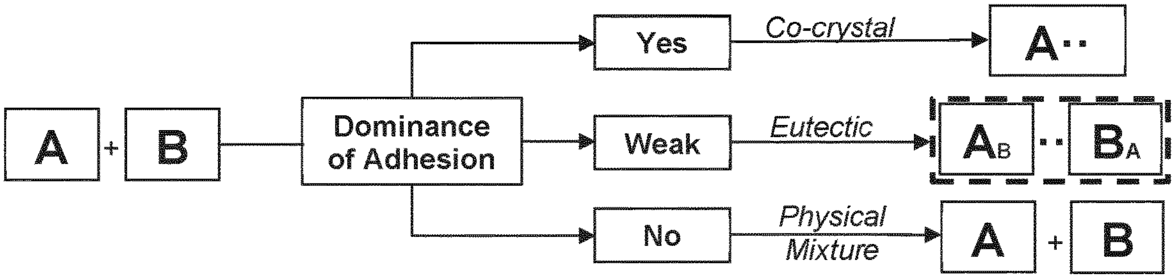
FIG. 2 is a graphical depiction of the impact adhesive interactions play in the formation of mixtures, eutectics, and co-crystals, wherein it is anticipated effective adhesive interactions are absent or weak in a eutectic, excluding the formation of a co-crystal.

A eutectic composition is a mixture of substances (in particular proportions) that melts and freezes at a single temperature that is lower than the melting points of the separate constituents or any other mixture of them. FIG. 2 herein presents a graphical representation of the anticipated impact adhesive interactions play in the formation of mixtures, eutectics, and co-crystals.

An amphipathic compound as contemplated herein has a structure comprising two distinct regions with contrasting hydrophobic and hydrophilic properties. Eutectic compositions contemplated herein comprise one or more amphipathic compounds, such as one or more fatty acids, one or more fatty amines, and one or more fatty alcohols.

In certain embodiments, the eutectic composition comprises a short chain fatty acid, a medium chain fatty acid, a long chain fatty acid, or a very long chain fatty acid. In certain embodiments, the fatty acid is a saturated fatty acid. In other embodiments, the fatty acid is an unsaturated fatty acid, such as a polyunsaturated fatty acid.

Representative saturated fatty acids include caprylic acid, capric acid, lauric acid, myristic acid, palmitic acid, stearic acid, arachidic acid, behenic acid, lignoceric acid, and cerotic acid.

Representative unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid.

Particularly contemplated fatty acids include myristic acid, oleic acid, stearic acid, palmitic acid, lauric acid, glycerol monostearate, and any combination of two or more thereof.

The fatty acid may be hexanoic acid (C6), hexanedioic acid (CM), a dicarboxylic fatty acid, capric acid (C10), decanedioic acid (C10), lauric acid (C12), dodecanedioic acid (C12), tetradecanedioic acid (C14), Capric acid, Myristic acid, Oleic acid.

The fatty alcohol may be 1-Dodecanol, Heneicosanol, Elaidyl alcohol, Petroselinyl alcohol, 1-tetradecanol, 1-Docosanol, 1-Tridecanol, 1-Nonadecanol, 1-Triacontanol, 1-Pentadecanol, 1-Nonanol, 1-Tricosanol, Cetyl alcohol, Stearyl alcohol, 1-Decanol, Isooctyl alcohol.

The fatty amine may be Pentadecylamine, Hexadecylamine, Docecylamine, Decylamine, Tridecylamine, Octadecylamine, Undecylamine, N, N-dimethyltetradecylamine, Dodecylamine, Octadecylamine In certain embodiments, the devices described herein comprise active agents that have the property of remaining soluble and/or not crystallising when formulated as a eutectic composition as described herein. The inventors have surprisingly found that this property enables the devices of the present invention to maintain stability at higher temperatures than would normally be possible using the active agents alone, or in non-eutectic formulations. This property also enables higher active agent loading (concentration) than would otherwise be possible using non-eutectic compositions. Further, crystallisation results in non-uniform distribution of active agents which can result in unpredictable and non-homogenous elution of active agent from the device. This unpredictability is typically undesirable in a clinical setting. Crystallisation of the active agents can be observed by "blooming" (bright spots) on the surface of the device, for example on the surface of an implant. Such "blooming" is one indicator of crystallisation and can be identified by methods known to those of skill in the art, for example Raman mapping to identify active agent dispersion in or on the device, for example as described in example 3. Other indicators of crystallisation will be known to those of skill in the art.

Methods of Manufacturing Implants

In another aspect, the invention relates to a method of manufacturing a device, such as an implant, as herein described. Broadly, the method comprises providing a eutectic mixture comprising one or more active agents and one or more of the group comprising one or more fatty acids, one or more fatty alcohols, and one or more fatty amines, including any combination of two or more thereof, and admixing said eutectic composition with one or more biocompatible polymers to form the device.

The devices described herein are amenable to manufacture by any methodology capable of forming biocompatible polymer containing compositions in which one or more active agents are or are to be present. It will be appreciated by those skilled in the art on reading this disclosure that certain active agents are, for example, more heat labile than others, while certain active agents require a particular physicochemical environment to enable requisite stability during and post device manufacture. Accordingly, the selection of an appropriate manufacturing process will be guided by, for example, the nature of the device, the one or more polymers present in the device, the structure of the device (for example, single layer, multi-layer, elongate, cross-section size and shape, etc), the composition of the eutectic, the one or more active agents or other agents present in the device, and the proposed use of the device. Other considerations, including manufacturing cost, long term stability, and the like, may also factor into the selection of the appropriate manufacturing process.

Notably, the inventors have observed that in certain embodiments when a eutectic composition is incorporated into the polymer composition, the melting point of the polymer is lowered. Accordingly, the devices and methods as herein described are particularly suited to use with heat-labile drugs and/or active agents that benefit by not being exposed to high temperatures, for example, during manufacture of devices lacking a eutectic mixture. It will be appreciated that, in certain embodiments not only is a stability benefit thus able to be achieved, but the incorporation of a eutectic composition will in certain embodiments also decrease the cost of production due to energy savings, less stringent temperature control of manufacturing plant, and the like.

According to some embodiments, devices are formed through suitable polymer processing methods. Representative methods of use herein include extrusion, such as hot-melt extrusion, co-extrusion, and the like, molding such as injection molding, additive manufacturing methods, and electrospinning.

In one example, the device, for example the implant, is manufactured using hot melt extrusion (HME). HME is a promising technology for manufacturing medical implants that involves application of heat, pressure, and agitation through an extrusion channel to mix materials together, then force them out through a die. HME blends materials while imparting high shear stress to break-up particles and disperse them. It offers several advantages over conventional manufacturing techniques including being a continuous, high throughput process, will typically be solvent-free, is amenable to use with poorly water-soluble drugs, produces devices needing little or no downstream processing, is compatible with low compressibility index active agents (e.g., low compressibility index Active Pharmaceutical Ingredients (APIs)), and provides readily controlled environmental conditions during manufacture, such as reduced exposure to oxygen or other gases in the extrusion channel.

Implantable compositions produced by HME typically have cylindrical forms, with dimensions of about 1 mm to about 5 mm in diameter, and are cut to desired length, for example from about 1 cm to up to 50 cm or more in length. In one example, implants for use herein are extruded through a die with a dimension of about 1.5 to about 5 mm, thereby to allow easy implantation via a surgical port. It will be appreciated that other forms of extrusions can be produced by HME, including sheets, for example, sheets suitable to forming into a bandage or wound dressing, and the like.

In one embodiment, a mixture of an active agent (such as lidocaine) is blended with EVA, PLA and/or PLGA polymers in a mixer, such as a Turbula mixer. In an embodiment, the implant is formed by extrusion. Extrusion can be performed by a suitable extruder, such as a Haake extruder. After the active agent and the polymer matrix have been blended together, they are force fed into an extruder and extruded into elongate rods or filaments. The extruded rods or filaments may then be cut into implants with a target weight/dosage, so as to deliver a target amount of active agent. Implants can then be sterilized and loaded into an injection device, such as a surgical applicator, for administration.

It will be appreciated that the example manufacturing parameters described herein are for descriptive purposes only. Other composition shapes and sizes and manufacturing techniques are contemplated and are within the skill of the art. For example, in one embodiment, the device is manufactured by co-extrusion, for example by simultaneous hot-melt extrusion of two or more materials through the same die, for example to create a multilayer extrudate. This approach enables the desirable attributes of various materials to be combined into a single structure to achieve enhanced performance.

Polymer selection is a paramount consideration for co-extrusion, with additional requirements needed to be accounted for compared to conventional monolayer hot melt extrusion. Despite the use of separate extruder barrels for each layer which can be controlled at different temperatures, a successful co-extrusion process requires the materials to melt at similar temperatures as the co-extrusion die is maintained at a single temperature. Moreover, materials with a similar melt viscosity and adequate adhesion between the layers are necessary to elicit high quality implants. Inter-diffusion of drug and/or polymer between the layers can be an unwanted complication of co-extrusion, but one that is amenable to resolution via appropriate selection of polymer and/or eutectic composition. Further, techniques such as Raman mapping (as exemplified herein) can be used to ascertain if migration/uniformity is a problem.

In certain embodiments, one or more plasticizers such as triacetin and triethyl citrate is added to the device, the implant, or a component thereof, for example to make manufacturing easier or more efficient.

Use of Eutectics to Enhance Lubricity.

FIGS. 40A to D illustrate the results of testing lubricity in EVA extrudates including eutectic fatty acid mixtures The eutectic system could be utilised as a lubricant for urinary catheters. For patients with urinary incontinence or retention, intermittent self-catherisation (ISC) provides an effective means of bladder management. However, the insertion and removal of a catheter can result in pain, mechanical injury, inflammation and bleeding. Furthermore, the local trauma can manifest in conditions such as urethritis and cystitis, which can be difficult to treat. Consequently, a catheter device with adequate lubrication to address this deleterious problem would be beneficial. A eutectic system which melts close to body temperature could be utilised as a means of providing a slippery catheter surface. This temperature responsive eutectic technology introduces a unique solution to addressing the shortcomings of other coated devices. The catheter would have a dry surface at ambient temperatures, improving the handling issues encountered with pre-lubricated catheters. Upon exposure to body temperature the device could be designed to elude the now molten oily liquid which could act as a lubricant. No preparation of the catheter would be required before use, in turn streamlining the catheterisation process. Sufficient lubrication and wetting on the catheter surface would reduce friction, easing the insertion and removal, and minimizing pain. Such a device, could improve user satisfaction, limit the risk of negative complications and reduce the likelihood of treatment on strained budgets.

In this new technology eutectics are utilized as a means of conferring enhanced lubricity to polymers without the drawbacks of coatings Lubricity Testing Control material tested consisted of polymer+no fatty acid Lubricity was measured for the following formulations in their eutectic ratios:

Oleic acid/capric acid (eutectic ratio 80 OA:20 CA)

Oleic acid/lauric acid (eutectic ratio 80 OA:20 LA)

Capric acid/lauric acid (eutectic ratio 65 CA:35 LA)

Capric acid/myristic acid (eutectic ratio 75 CA:25 MA)

All formulations were analysed in the following eutectic to polymer ratios, wherein the polymer was 12% EVA:

10% eutectic:90% polymer

20% eutectic:80% polymer

30% eutectic:70% polymer.

Coefficient of friction values were determined using a COF-1000 Coefficient of Friction machine in conjunction with EZ-Lab software For each run, two lengths of extrudate, approximately 6 cm long, were cut and stuck onto a 6 cm×6 cm sled weighing 219 g using carbon stickers The sled is then placed onto the test plate of the machine with the attached extrudates facing downwards and pulled along at a speed of 15 cm/min for a distance of 5 cm The software measures the force required to move the sled across the test plate which is then put into the following equation to determine coefficient of friction:

$$\mu=F/W$$

where μ=coefficient of friction, F is the horizontal force and W is the load applied.

Results

FIGS. 40A to 40D illustrate the results of testing lubricity in the extrudates including eutectic mixtures.

In all instances, the materials containing fatty acid eutectics are demonstrated to be more lubricious than the control polymer lacking fatty acid.

COF=Coefficient of Friction (the higher the value, the more friction)

Static COF=force required to initiate movement

Kinetic COF=calculated from average forces produced over the travelled distance after the initial movement These friction results are promising due to the majority of formulations demonstrating statistically significant reductions in friction compared to the control, especially the CA/LA and CA/MA formulations.

Furthermore, the majority of formulations comprising a eutectic composition demonstrated statistically significant reductions in friction compared to respective controls. This is particularly the case for the CA/LA and CA/MA formulations.

These data show that polymer devices as described herein can be prepared so as to have advantageous lubricity, for example to aid insertion and removal of insertable devices such as catheters, and/or reduce the risk of pain or tissue damage during the use of such devices.

Delivery of Active Agent

The development of dosage forms designed to release drug from the delivery platform to the surrounding biological fluids in a controlled manner, remains a continuing important aspect within the pharmaceutical industry. The purpose of controlled drug delivery is to maintain the drug concentration at therapeutic levels in the target tissues or blood for a required time. Consequently, controlled release systems can enhance the therapeutic outcomes whilst eradicating under- and over-dosing.

The devices, for example, the implants, described herein provide controlled release dosage forms via appropriate selection of polymer(s) and eutectic compositions, optionally together with various implant geometries and compositions, to tailor the release of drug from the system to the external environment. It will be recognised that the properties of both the drug and the polymer can influence the drug release. Important attributes of the former include, the hydrophobicity/hydrophilicity, solubility of the drug in the release media and the solubility/diffusion of drug in the polymeric matrix. It will likewise be appreciated that the solubility and or degradation characteristics of the polymer in the release environment, the degree of crystallinity of the polymer network, and its thermal properties, are all important considerations.

Drug elution from a drug-polymer implant is generally classified into three mechanisms; diffusion-controlled, erosion-controlled and swelling-controlled systems. A release system can function via any or all of these mechanisms. In certain embodiments of implants contemplated herein, the non-biodegradable, hydrophobic nature of EVA facilitates controlled release via controlled diffusion. It will be understood in the current context that diffusion occurs when there is random movement of drug molecules from an area of high concentration to an area of low concentration.

A typical matrix drug delivery platform consists of drug dissolved or dispersed within a polymeric matrix. The rate controlling process is the diffusion of drug through the matrix and the process is illustrated in FIG. 1. Drug present at the surface of the dosage form is dissolved first and diffuses from the matrix to the biological media. This poorly controlled release represents the burst effect. Subsequent release requires diffusion of drug though the matrix before dissolution in the media. Hence, the system is considered to be composed of an infinite number of layers containing drug with sequential release eliciting a greater zone of depletion.

The methods and devices described herein provide novel types of drug delivery systems, including those capable of rate-controlled delivery of active agent, in which the rate of drug delivery is controlled primarily by features of the implant and/or the eutectic composition, rather than by physiological or environmental conditions encountered by oral dosage forms and other matrix delivery systems. The devices provided herein include, for example, sustained release (SR) implants and extended release (ER) implants, including implants which effect one or more of (1) delayed total drug release some time after administration, (2) drug release in small aliquots intermittently after administration, (3) drug release slowly at a controlled rate governed by the delivery system, (4) drug release at a constant rate that does not vary, and/or (5) drug release for a significantly longer period than usual formulations.

Advantages of these devices for administration of one or more active agents include convenience to the subject; increased compliance and achievement of steady state drug levels with infrequent dosing; smoothening of plasma drug profiles to a constant level for extended time periods; prevention of drug toxicity; and elimination of breakthrough of therapeutic failure, for example at night. Rate-controlled delivery forms of the devices described herein include devices having drug release features based on time course, and/or location which are designed to accomplish therapeutic or convenience objectives not offered by conventional or immediate-release forms.

Of particular benefit is the enhanced active agent loading achievable with the devices described herein, which, together with the capacity for controlled delivery/release of active agent, enables the administration of a device as herein described to safely provide sufficient active agent to achieve therapeutic efficacy over durations that may otherwise require more frequent administration of the active agent, or of a larger implant, or bolus doses of active agent.

In certain embodiments, the device, for example the implant, comprising a eutectic composition as herein described has lower burst release of the active agent than a comparable device lacking the eutectic composition. For example, the device, for example the implant, comprising a eutectic composition as herein contemplated has a more controlled release of active agent than a comparable device lacking the eutectic composition.

In certain embodiments, the device, for example the implant, is coated with a degradable coating to further regulate active agent release. In various examples, a lipid excipient, such as an excipient comprising esters of behenic acid and glycerol, is applied to the external surface of the device to prevent the release of an initial burst of active agent shortly after administration, for example, shortly after the implant is implanted or inserted in a subject. In various embodiments, devices contemplated herein comprise one or more coatings or coating excipients.

Duration of the active agent release period and the desired plasma levels for different actives form additional design considerations. In certain embodiments, the amount of eutectic composition, and/or the concentration or amount of active agent present in the eutectic composition, and/or the location of the eutectic composition in the device, provide flexibility with respect to the release rate and kinetics.

In other embodiments, variation in thickness and diameter of the device, and/or variation in the length of device, and/or variation in the number of devices used in a subject provide flexibility in the amount of active agent released, for example, the amount of active agent released per hour. The optimal drug dosage rate dispensed by the device depends on factors including the condition for which the active agent is being administered, the physiology of the subject, species in which it is used, the location of implantation or insertion, and body weight of the patient.

The dosage rate will be readily ascertainable to physicians, veterinarians, and other medical experts. For treatment of pain, the analgesic active agent is desirably released at a rate that maintains plasma levels of the active agent at a therapeutically effective level. Moreover, depending upon the nature of the pain condition being treated and the particular subject, devices, such as implants, will in certain embodiments be used to release therapeutically effective amounts of one or more active agents for several weeks, months, or even up to two years or longer. In such contexts, a therapeutically effective amount refers to the amount of active agent required to render a desired therapeutic outcome—for example, a reduction in pain or analgesic relief of pain, or a reduction in self-administration of non-prescribed or other analgesic active agents.

In specifically contemplated embodiments, after subcutaneous implantation in a subject, an implant as described herein releases one or more active agents for analgesia, including for pre-emptive analgesia and/or other pain management therapies continuously in vivo at a rate that results in a plasma level of at least about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, or 10 ng/ml.

In specifically contemplated embodiments, after implantation in a subject, an implant as described herein releases one or more active agents for pain management therapies at a rate of at least about 0.01, 0.05, 0.1, 0.5, 1, 2, 3, 4, 5, 6, 7, 8, 9, 10, 20, 30, 50, or 100 mg/day in vivo. Two exemplified embodiments described below release about 240 mg/day in vivo.

For example, after intraperitoneal or subcutaneous implantation in a subject, an implant as described herein comprising lidocaine releases lidocaine in vivo at a rate of at least about 0.1, 0.5, 1, 2, 3, 4, 5, 6, or at least about 7 g/day.

In specifically contemplated embodiments, after intraperitoneal or subcutaneous implantation in a subject, an implant as described herein releases one or more active agents for analgesia in vivo at a rate of at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 $mg \cdot kg^{-1} \cdot h^{-1}$.

For example, after intraperitoneal or subcutaneous implantation in a subject, an implant as described herein comprising lidocaine releases lidocaine in vivo at a rate of at least about 0.1, 0.2, 0.3, 0.4, 0.5, 0.6, 0.7, 0.8, 0.9, 1, 2, or at least about 3 $mg \cdot kg^{-1} \cdot h^{-1}$.

Particularly contemplated embodiments of devices for implantation, for example implantation into the peritoneal cavity, include elongate implantable compositions, for example devices having a generally cylindrical form, whereby a desired dose of active agent can be readily provided by preparing the device to a desired dimension, such as a desired length. In one example, a device for peritoneal implantation and administration of one or more analgesics or anaesthetics is prepared as a cylinder, for example a cylinder of about 1 mm to about 5 mm in diameter, and is cut to desired length sufficient to deliver a desired dose of analgesic or anaesthetic. Specific representative embodiments of such a cylindrical device are exemplified herein in the Examples, in which a total length of 159.5 cm of cylindrical extrudate composition was implanted in the peritoneal cavity of an animal model. In this exemplified embodiment, the total length of extruded composition when implanted provided an administered dosage of 2.57 g of lidocaine. It will be appreciated that a different administered dose was readily achievable by cutting the extruded composition to differing lengths, administering one or more fewer or additional lengths of composition, or any combination thereof—without recourse to preparing a composition having a different drug loading per unit length, weight, or diameter. It will likewise be understood that further flexibility in dose administration can easily be accommodated by changing the formulation (such as the drug loading/concentration) of the composition, or the physical form of the composition, such as by increasing or decreasing the thickness of one or more drug eluting layers of the device.

A specifically contemplated use for devices such as those exemplified in the Examples is the administration of one or more anaesthetics, such as lidocaine, to the peritoneal cavity of a subject who has undergone surgery, in whom effective pain relief can be achieved with a lessened reliance on systemic pain relief.

The local administration of an anaesthetic such as lidocaine to the peritoneal cavity is thought, without wishing to be bound by any theory, to target the vagus nerve, and in so doing reduce the need for or reliance on systemic pain relief. Furthermore, the implantation of a device as contemplated herein allows for controlled, and if desired constant, release of anaesthetic within the peritoneal cavity without the need for infusion or perfusion, active external pumps, and the like previously required to achieve the pain management benefits observed with localized delivery of a local anaesthetic to the peritoneal cavity.

As a result, implantable devices as contemplated herein provide effective pain relief with a reduced reliance on or reduced dosages of systemic analgesics such as opiates, enabling treatment including post-operative care with fewer side effects.

Embodiments contemplated herein include devices for combination therapy. As used herein, "combination therapy" includes treatment methods that administer two or more active agents. Combination therapies may be used to treat one or more conditions and therapies for treating two or more conditions may target related or unrelated conditions. One example of a device, for example an implant, including two or more active agents comprises a single core or compartment for disposing two or more active ingredients. To provide different release profiles, one or more active ingredients may be coated with a bio-erodible or biodegradable polymer. Two or more coatings may be applied to the same active ingredient and the degradation rates of the coatings may be varied to provide faster or slower release rates.

Another example of a device, such as an implant, comprises two layers for disposing one or more active ingredients. In one example, the multi-layer embodiment has two coaxial layers, wherein an inner core and an outer layer each include one or more active agents, at least one of which is a eutectic composition as herein contemplated, and will in certain examples also comprise one or more polymers. The device will in certain embodiments additionally include at least one outer coating on the external surface of the device. A second coating may be applied to the outside of the inner core to separating the inner and outer layers.

In this example, the inner core and outer core are concentric layers comprising drug delivery systems made of one or more polymer materials. The material composition of each concentric layer may include the same polymer with different layers having different concentrations, monomer ratios, or degree of crosslinking. Alternatively, the concentric layers may further include one or more different polymers for each layer with different layers having different compositions or the same compositions with different concentrations, monomer ratios, or degree of crosslinking. It will be appreciated that each layer may include a eutectic composition as herein contemplated, wherein the eutectic comprises the same or a different fatty acid, fatty alcohol, fatty amine, or combination thereof.

Accordingly, active agents are loaded into each layer, for example, into the polymer matrix of each concentric layer. In this example, the active agent loaded into the inner core is different from the active agent loaded into the outer core. This arrangement is ideal for combination treatments requiring two or more active agents. Other examples include the same active agent in each layer or two or more active agents in a single layer. In embodiments having two or more active agents in one layer, one or more of the active agents may be coated with a non-erodible or biodegradable polymer to regulate the rate of active agent release.

Outer coatings may be added to the external surface of one or more concentric layers. In one example, the device comprises an outer coating around the external surface of the outer core. The outer coating can help regulate drug release by preventing an initial burst of the active ingredient, for example immediately after the implant is inserted into a subject, particularly when one or more active agents is present in the implant without being formulated in a eutectic composition as contemplated herein. In this example the outer coating encloses the outer surface of the device in a layer of bio-erodible polymer. Once the device has established equilibrium in vivo, for example shortly after implantation or insertion, the outer coating erodes to dispense the active agent(s), usually through pores on the external surface of the device. The delay provided by the outer coating will help keep the release of agent constant for the full life of the device and reduces risk of side effects associated with elevated plasma levels of one or more active agents, such as but not limited to liver and kidney damage, upset stomach, and loss of appetite, or anaesthetic overdose. The length of the delay provided by the outer coating may be varied by changing the composition of the outer coating. Coatings comprising more robust polymers may provide a delay of several days or weeks. Alternatively, readily degradable coatings may only provide a few minutes or hours of delay.

The devices provided herein are amenable to use with any active agent.

Specifically contemplated devices and compositions include those useful in pre-emptive analgesia techniques. Examples of such devices, particularly implants, and compositions support the release of multiple active ingredients from the same drug delivery device. Active ingredients included in such implants and compositions include any species of the group comprising local anaesthetics, NSAIDs, opioids, α-2 adrenoceptor agonists, NMDA antagonists, steroids and corticosteroids, and combinations thereof, such as local anaesthetics and NSAIDs.

In certain embodiments, the anaesthetic is selected from the group comprising morphine, noroxymorphone, bupivacaine, lidocaine, ibuprofen, prilocaine, or ropivocaine, including any combination of two or more thereof.

In other embodiments, the implant or eutectic compositions comprises Carprofen, Carprofen with morphine, Carprofen with Amantadine, Carprofen with Gabapentin, Carprofen with Tramadol, Meloxicam with Gabapentin, Meloxicam, Meloxicam with Morphine, Meloxicam with Amantadine, Tramadol with Gabapentin, Tramadol with Amantadine, Tramadol with Amitriptyline, Dexmedetomidine with Morphine, Xylazine with Morphine, Dexmedetomidine with Remifentanil, Dexmedetomidine with Fentanyl, Amantadine and Amitriptyline combination, Amantadine with Morphine, Amantadine, Dexmedetomidine with morphine, Dexmedetomidine with Fentanyl, Dexmedetomidine with Buprenorphine, Dexmedetomidine with Ketamine, Xylazine with Ketamine, Xylazine with Morphine, Xylazine in combination with Fentanyl, Xylazine with Buprenorphine, Cinchophen and prednisolone (corticosteroid), Duloxetin, Pamidronate, Zoledronate, Morphine with benzodiazepines, Morphine with acepromazine, Morphine with Romifidine, Morphine with Xylazine, Morphine with Medetomidine, Morphine with Dexmedetomidine, Fentanyl with benzodiazepines, Fentanyl with Xylazine, Fentanyl with Dexmedetomidine, Fentanyl with Medetomidine, Fentanyl with Romifidine, Fentanyl with acepromazine, Buprenorphine with Medetomidine, Buprenorphine with Dexmedetomidine, Buprenorphine with Romifidine, Buprenorphine with Xylazine, Buprenorphine with benzodiazepines, Buprenorphine with acepromazine, and Pamidronate with zoledronate.

Particularly contemplated embodiments, including several exemplified herein in the Examples, comprise the anaesthetic lidocaine. Lidocaine, or 2-(diethyl-amino)-N-(2,6-dimethylphenyl)-acetamide, has a molecular weight of 234.34 g/mol and consists of a benzene ring and tertiary amine group linked by

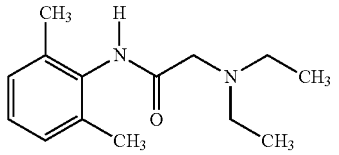 [SMILES: CCN(CC)CC(=O)Nc1c(C)cccc1C]

an amide bond, as shown below.

Lidocaine

The short half life of local anaesthetics such as lidocaine, prilocaine, rupivocaine, bupivacaine and tetracaine limits the duration of their analgesic effect, but does mean that in the event of an overdose or adverse event they are cleared rapidly from the body.

The devices including implants described herein achieve sustained effect through the sustained release of drug into the body. Toxicity can readily be monitored or predicted by monitoring plasma levels.

The devices, such as an implant, contemplated herein will in certain embodiments comprise, or be administered together with, a pharmaceutically acceptable carrier.

The term "pharmaceutically acceptable carrier" refers to a carrier (adjuvant or vehicle) that may be administered to a subject together with the one or more active agent, or a pharmaceutically acceptable salt or solvate thereof.

One such carrier is saline (0.9% sodium chloride), though other carriers are applicable.

Pharmaceutically acceptable carriers that may be used in the device and/or eutectic compositions include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives may also be advantageously used to enhance delivery. The implant may additionally comprise or be administered together with an oil solutions or suspensions, which may in turn also contain a long-chain alcohol diluent or dispersant, or carboxymethyl cellulose or similar dispersing agents.

It will be appreciated that a pharmaceutically acceptable carrier in the context of the methods and devices described herein will typically allow for administration to a subject by any parenteral route, including subcutaneous, subdermal, intramuscular, peritoneal, and intravenous administration. It will likewise be appreciated that for devices as described herein for use in topical administration, suitable pharmaceutically acceptable carriers are well known in the art.

Therapeutic Methods

The methods and devices described herein are in certain embodiments used in therapeutic methods, for example, in the treatment of one or more diseases, disorders, pathologies, or conditions in a subject in need thereof.

A "subject" as used herein is an animal, usually a mammal, including a mammalian companion animal or a human. Representative companion animals include feline, equine, and canine. Representative agricultural animals include bovine, ovine, caprine, cervine, and porcine.

In will be appreciated that the various methods of therapy contemplated herein will typically embody the administration of an effective amount of one or more active agents.

An "effective amount" is an amount sufficient to effect beneficial or desired results including clinical results. An effective amount can be administered in one or more administrations by various routes of administration. The effective amount will vary depending on, among other factors, the disease or condition indicated, the severity of the disease or condition, the age and relative health of the subject, the potency of the agent administered, the mode of administration and the treatment desired. A person skilled in the art will be able to determine appropriate dosages having regard to these any other relevant factors.

Specifically contemplated diseases, disorders, pathologies or conditions to be treated include those that would benefit from minimisation of pain and/or inflammation in the subject.

The term "treatment", and related terms such as "treating" and "treat", as used herein relates generally to treatment, of a human or a non-human subject, in which some desired therapeutic effect is achieved. The therapeutic effect may, for example, be inhibition, reduction, amelioration, halt, or prevention of a disease or condition.

In certain embodiments, the eutectic composition is utilised as a lubricant or provides lubricity, for example for urinary catheters. For patients with urinary incontinence or retention, intermittent self-catherisation (ISC) provides an effective means of bladder management. However, the insertion and removal of a catheter can result in pain, mechanical injury, inflammation and bleeding. Furthermore, the local trauma can manifest in conditions such as urethritis and cystitis, which can be difficult to treat.

Consequently, a catheter device with adequate lubrication to address this deleterious problem is of significant benefit.

In certain embodiments, the device, such as an implant, comprises a eutectic composition which melts close to body temperature to provide a slippery device surface. Advantageously, particularly for handling by end-uses/subjects who have not undergone extensive medical training, the device, such as the urinary catheter, has a dry surface at ambient temperatures, avoiding the handling issues encountered with pre-lubricated catheters. Upon exposure to body temperature, the device is configured to elude the now molten oily eutectic composition, which acts as a lubricant. No preparation of the catheter would be required before use, in turn streamlining the catheterisation process. Sufficient lubrication and wetting on the catheter surface would reduce friction, easing the insertion and removal, and minimizing pain. It will be appreciated that user satisfaction is thus improved, while the risk of negative complications is reduced.

Accordingly, in certain embodiments of the devices described herein, the eutectic composition is utilized as a means of conferring enhanced lubricity to polymer devices without the drawbacks of lubricated coatings.

The invention is further described with reference to the following examples. It will be appreciated that the invention as claimed is not intended to be limited in any way by these examples.

EXAMPLES

Example 1: Assessment of Drug Loading of EVA Polymers

This example describes the assessment of the drug loading capacity of various EVA formulations.

Various extrudates and solvent caste films comprising EVA and lidocaine were assessed. At higher concentrations of lidocaine in EVA, crystallisation of drug occurred on storage. As will be appreciated, crystallisation presents a number of problems, not only stability issues, with implant composition/drug availability changing with time, but drug crystals are easily dislodged from the polymer surface, leading to inaccurate dosing and altered drug release, with rapid dissolution of drug crystals potentially causing an increase in burst release.

Briefly:

From DSC testing, LIDO in EVA 12% systems yielded a crystalline drug within a semi-crystalline carrier.

A 5% LIDO/EVA 33% extrudate existed as a single phase amorphous drug/EVA within a semi-crystalline carrier.

For a 20% LIDO/EVA 33% composition, crystallisation occurred with a significant decrease in the Tg and presence of a melting peak for LIDO present on DSC. This is in agreement with the Raman mapping data for 20% LIDO/EVA 33% extrudates, where crystalline LIDO was prominent at the circumference with amorphous LIDO found at the cross-section.

Stability studies (20° C./75% RH) revealed rapid recrystallisation of LIDO from all drug loadings of the LIDO/EVA 12% extruded systems and the 20% LIDO/EVA 33% formulation. This yielded unsuitable devices as drug loss was possible due to LIDO shearing from the surface. In contrast, the 5% LIDO/EVA 33% extrudates maintained LIDO in the amorphous form for the duration (48 weeks) of the stability test.

In summary, these data show that, when including lidocaine into a solvent cast EVA film or EVA polymer implant, concentrations of lidocaine over 9-10% w/w crystallise out. In the context of pharmaceutically-advantageous drug loadings, in the drug/EVA compositions tested above, the drug crystallised at loadings of 20%. Thus, these data confirm that simple polymer compositions have limited ability to support high concentrations of drug and still provide for safe and/or effective administration.

Example 2: Formation and Assessment of Eutectic Compositions

This study assessed the formation of eutectic compositions comprising lidocaine and various fatty acids. Table 1 below presents the physical and chemical properties of the agents assessed in this example.

TABLE 1

Physical and chemical properties of lidocaine, myristic acid, stearic acid and glycerol monostearate.

| Chemical | Chemical Structure | Molecular Formula | LogP | Polar Surface Area (Å$^2$) |
|---|---|---|---|---|
| Lidocaine (231) | 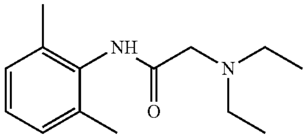 [SMILES: CCN(CC)CC(=O)Nc1c(C)cccc1C] | $C_{14}H_{22}N_2O$ | 2.84 | 32.34 |
| Myristic Acid (232) | 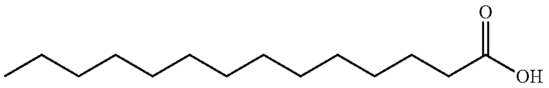 [SMILES: CCCCCCCCCCCCCC(=O)O] | $C_{14}H_{28}O_2$ | 5.37 | 37.30 |

TABLE 1-continued

| Physical and chemical properties of lidocaine, myristic acid, stearic acid and glycerol monostearate. | | | | |
|---|---|---|---|---|
| Chemical | Chemical Structure | Molecular Formula | LogP | Polar Surface Area ($Å^2$) |
| Stearic Acid (233) | 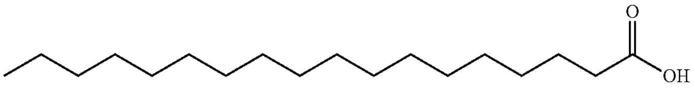 [SMILES: CCCCCCCCCCCCCCCCCC(=O)O] | $C_{18}H_{36}O_2$ | 7.15 | 37.30 |
| Glycerol Monostearate (234) | 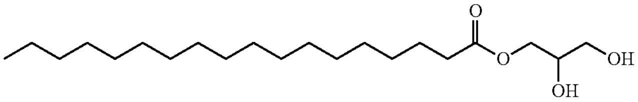 [SMILES: CCCCCCCCCCCCCCCCCC(=O)OCC(O)CO] | $C_{21}H_{42}O_2$ | 5.97 | 66.76 |

The compositions prepared herein were analysed using the following methods, which enabled the identification of eutectic compositions of particular interest.

Differential Scanning Calorimetry (DSC)

DSC was utilised to determine the melting point, recrystallisation temperature and enthalpy of the relevant samples. Samples were weighed into Perkin-Elmer Aluminum Non-Hermetic DSC pans and subsequently crimped using a Perkin-Elmer press. Nitrogen was used as the purge gas at a flow rate of 50 mL $min^{-1}$. Preliminary DSC studies were conducted on the pure excipients.

Lidocaine (LIDO), stearic acid (SA), myristic acid (MA), and glycerol monostearate (GMS), were accurately weighed (5-10 mg) into the DSC pans. The second set of experiments involved using DSC to establish the influence on the thermal events when the selected lipids were combined with LIDO. Initial screening experiments involved DSC runs at 10° C. min-1 and mixing the two excipients using various methods, including cryo-milling and blending with a mortar and pestle. These results facilitated optimization of the current method.

To ensure accurate molar ratios of the binary mixture and to overcome potential issues with achieving homogenous mixtures, relevant masses of LIDO and the lipid were weighed directly into the DSC pan (total weight: circa 10 mg). The same DSC method was applied for the pure excipients and the binary mixtures. A heating and cooling rate of 1° C. $min^{-1}$ was used to ensure the compositions were given sufficient time to respond to the input of energy. Consequently, a slow heating rate provides experimental conditions that facilitates enhanced contact of the starting components and does not inhibit solubilisation, where applicable. In addition, a slow cooling rate assists optimal recrystallisation of the molten form. The DSC was equilibrated at −90° C. and a heat/cool/heat cycle was employed:

1. Heat from −90° C. to 85° C., at 1° C. $min^{-1}$
2. Cool from 85° C. to −90° C., at 1° C. $min^{-1}$
3. Heat from −90° C. to 85° C., at 1° C. $min^{-1}$ The resulting melting points (2nd heat) and recrystallisation temperatures (1st cool) were plotted graphically as a function of lidocaine percentage molar ratio to construct phase diagrams.

Powder X-Ray Diffraction (PXRD)

PXRD was employed to determine the physical state of LIDO in the LIDO:fatty acid compositions. To ensure intimate mixing of each formulation, the systems were prepared by melting, permitting interactions at a molecular level. The components were weighed according to Table 2 and heated at 80° C. until molten. Subsequently, the molten sample was transferred to a frosted glass slide. The sample was left for 24 hours to allow it to cool and solidify, where applicable. The pure starting components were prepared in the same manner to facilitate accurate comparisons. To ascertain the impact of melting the compounds, analysis of the pure starting compounds with no thermal history was conducted. A uniform particle size was achieved by passing the materials through a 250 μm sieve and subsequently the resultant sample was prepared on a frosted glass slide before insertion to the diffractometer. PXRD was performed using a 20 scanning range of 3-40° at a scanning speed of 2° min-1 was employed. The operating voltage and current applied were 30 kV and 15 mA, respectively.

Two-Dimensional Correlation Fourier-Transform Infrared Spectroscopy

Two-dimensional correlation Fourier-transform infrared spectroscopy (2DCOS FTIR) was utilised to evaluate the formation and underlying mechanism of formation of eutectic compositions comprising lidocaine and myristic acid, in the presence or absence of EVA polymers.

Binary mixtures: 2-3 mg of sample was triturated in ~200 mg KBr to prepare pellets and analysed in transmission mode. The samples were:

Lidocaine (100%) Lido:MA 1:2

Lido:MA 1:1 Lido:MA 2:1

MA (100%)

All samples were analysed in Transmission mode and data recorded. A 2D Cross correlation analysis of the five mixtures of lidocaine and myristic acid was run and the synchronous and asynchronous maps were compared with the spectra.

Thermogravimetric Analysis (TGA)

TGA was utilised to determine thermal stability. Initially the starting materials (LIDO, MA, SA and GMS) were analysed to deduce the degradation temperature. The excipients were exposed to a heating ramp from room temperature (circa 20° C.) to 500° C., at 10° C. min-1.

LIDO and the relevant lipids were weighed and heated at 80° C. until molten. The samples were given 24 hours to cool/solidify before they were ground using a mortar and pestle for 2 min. The resultant systems were heated at 10° C. min-1 from room temperature to 350° C. All TGA experiments were conducted in triplicates, using Perkin-Elmer Aluminum Non-Hermetic DSC pans. Nitrogen (60 mL min-1) was used as the purge gas. The degradation temperature was reported at 5% weight loss. Analysis was performed using TA Universal analysis software.

Molar Binary Compositions

To provide a thorough understanding and to aid characterisation of the binary systems, three molar ratios of each binary system were investigated in further studies as shown in Table 2.

These compositions were selected in accordance with the DSC results and represent:

1. COMPOSITION 1: LIDO/LIPID (x:y moles). For LIDO/MA and LIDO/SA: the experimentally determined eutectic composition. For LIDO/GMS: as no composition tested had a single endotherm on the heating ramp, the composition with the greatest enthalpy pertaining to solidus A was selected (data not shown);
2. COMPOSITION 2: LIDO IN EXCESS (2x:y moles);
3. COMPOSITION 3: LIPID IN EXCESS (x:2y moles).

TABLE 2

Summary of the molar ratios for each formulation.

| Formulation | Composition 1 LIDO/LIPID (moles) | Composition 2 LIDO/LIPID (moles) | Composition 3 LIDO/LIPID (moles) |
|---|---|---|---|
| LIDO/MA | 1:1 | 1:0.5 | 1:2 |
| LIDO/SA | 1:0.47 | 1:0.24 | 1:0.94 |
| LIDO/GMS | 1:0.67 | 1:0.33 | 1:1.33 |

Statistics

The level of significance for the statistical analysis, was denoted at $p<0.05$ (hence, individual probability values were not quoted). The effect of incorporating a second component on the FTIR band positions and the degradation temperature deduced using TGA, were statistically evaluated using a one-way ANOVA. To determine individual differences a Tukey-Kramer post hoc test was subsequently applied.

Results

Differential Scanning Calorimetry (DSC)

Lidocaine and Myristic Acid—Melting

The DSC data demonstrate the addition of MA to the LIDO system elicits an endothermic melt at approximately 20° C., across all the molar ratios explored (except 4.6% moles of LIDO). Furthermore, a second endothermic melt at a higher temperature (>20° C.) is observed at all compositions except for 48.9% moles of LIDO. A summary of the experimentally determined melting points and corresponding enthalpies for the observed endotherms is shown by each data point in FIG. 3.

Figure 3:
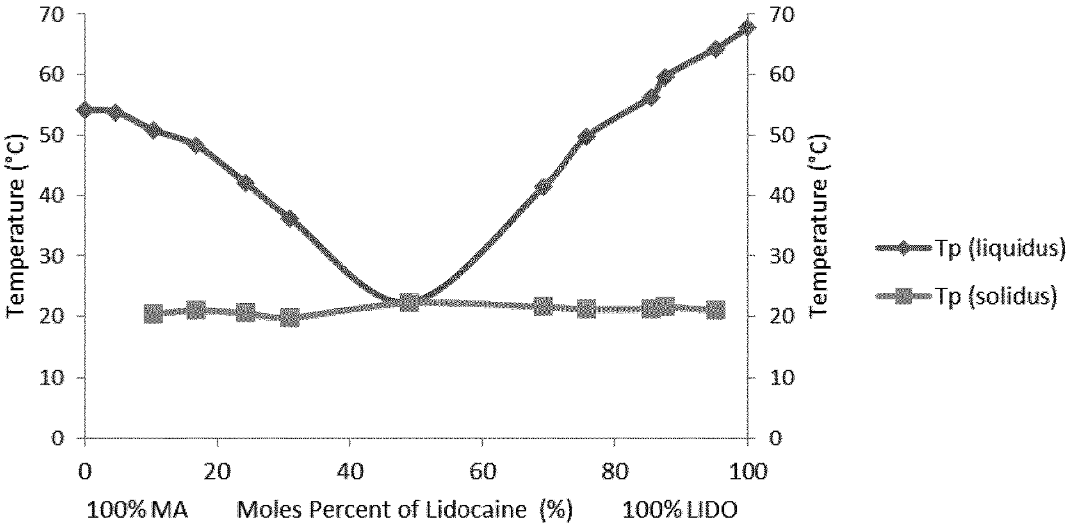
FIG. 3 is a graph depicting the melting point of the binary mixtures of lidocaine and myristic acid during the second heating cycle.

The two endothermic peaks observed at certain compositions of the LIDO/MA system are depicted in the phase diagram (FIG. 3). The observed melts correspond to eutectic systems and can be defined as:

Liquidus melting point: the system is completely liquid at temperatures above this point, Solidus melting point: the system is completely solid at temperatures below this point.

Lidocaine and Stearic Acid—Melting

Figure 4:
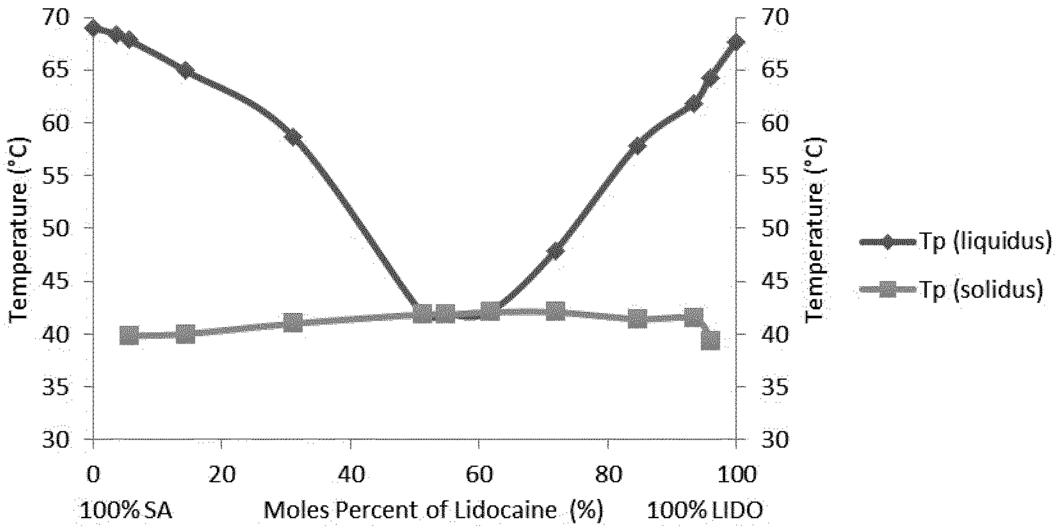
FIG. 4 is a phase diagram depicting the melting point of the binary mixtures of lidocaine and stearic acid during the second heating cycle

FIG. 4 illustrates the phase diagram for the LIDO/SA system during the second heating cycle and displays the observed endotherms. Melting points and corresponding enthalpies for the observed endotherms were experimentally determined (data not shown). FIG. 4 demonstrates the addition of SA to the LIDO system elicits an endothermic melt at approximately 40° C., across all the molar ratios explored (except 3.7% moles of LIDO, some data not shown). Furthermore, a second endothermic melt at a higher temperature (>40° C.) is observed at all compositions except for 61.7% moles of LIDO.

Liquidus Melting Point

Figure 5:
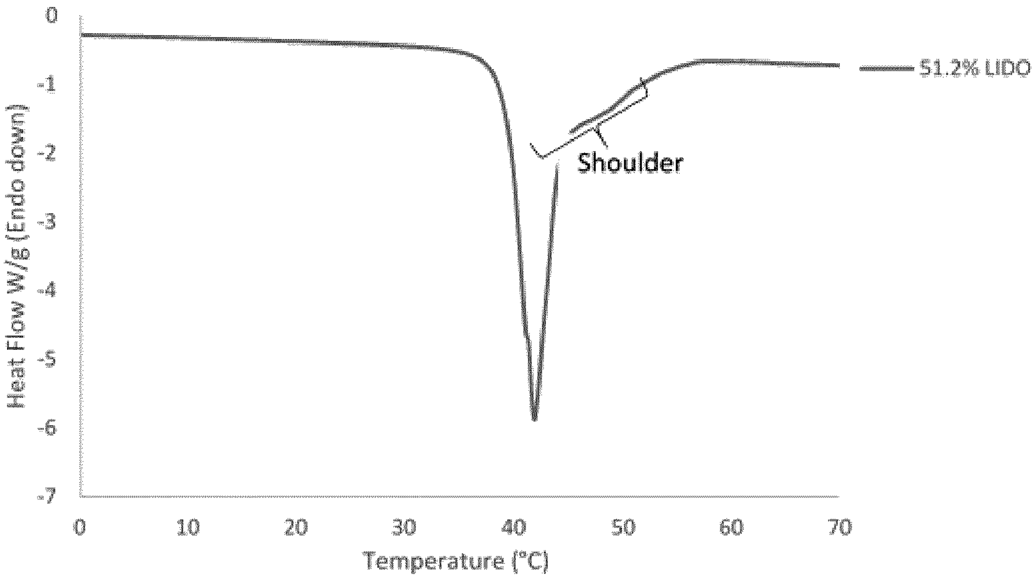
FIG. 5 is a thermogram depicting the second heating cycle for 51.2% moles of LIDO for the LIDO/SA binary mixture.

FIG. 4 illustrates due to multiple endotherms, LIDO is the dominant species for the LIDO/SA binary system, in the range, 71.8-95.9% moles of LIDO. In light of the addition of SA, the liquidus melting point and enthalpy of pure LIDO decreases proportionality to 47.86° C., 6.16 J $g^{-1}$ (71.8% moles of LIDO). Compared to pure LIDO (67.70° C., 71.10 J $g^{-1}$), this is a reduction in the liquidus melting point and enthalpy of 19.84° C. and 64.94 J $g^{1}$, respectively (data not shown). At 3.7-54.8% moles of LIDO, SA is the dominant species in the system. Pure SA has a peak melting point temperature of 68.98° C., with an enthalpy of 215.2 J $g^{-1}$. Increasing the quantity of LIDO in the binary system results in a reduction of the melting point and enthalpy of SA. At 31.1% moles percent of LIDO the greatest depression in the melt and enthalpy is observed to 58.70° C. and 65.16 J $g^{-1}$, respectively. The shoulder observed on the solidus melting peak for 51.2% and 54.8% moles of LIDO are due to the melting point depression of SA. The former is illustrated in FIG. 5.

Solidus Melting Point

FIG. 4 depicts that at 61.7% moles of LIDO, the second heating ramp elicits a single endothermic peak. This event corresponds to the solidus melting point. Furthermore, the solidus melt is detected at all the binary systems analysed, with the exception of 3.7% moles of LIDO. As such, the recorded solidus melting points are imperceptible across the binary ratios (41.32±0.87° C.). In contrast, the enthalpy values vary. The greatest enthalpy (117.50 J $g^{-1}$) was observed experimentally at 61.7% moles of LIDO. With increasing amounts of the respective dominant species the enthalpy associated with the solidus melt decreases, to 26.99 J $g^{-1}$ and 7.48 J $g^{-1}$, for 93.3 and 5.5% moles percent of LIDO, respectively.

Lidocaine and Glycerol Monostearate—Melting

Figure 6:
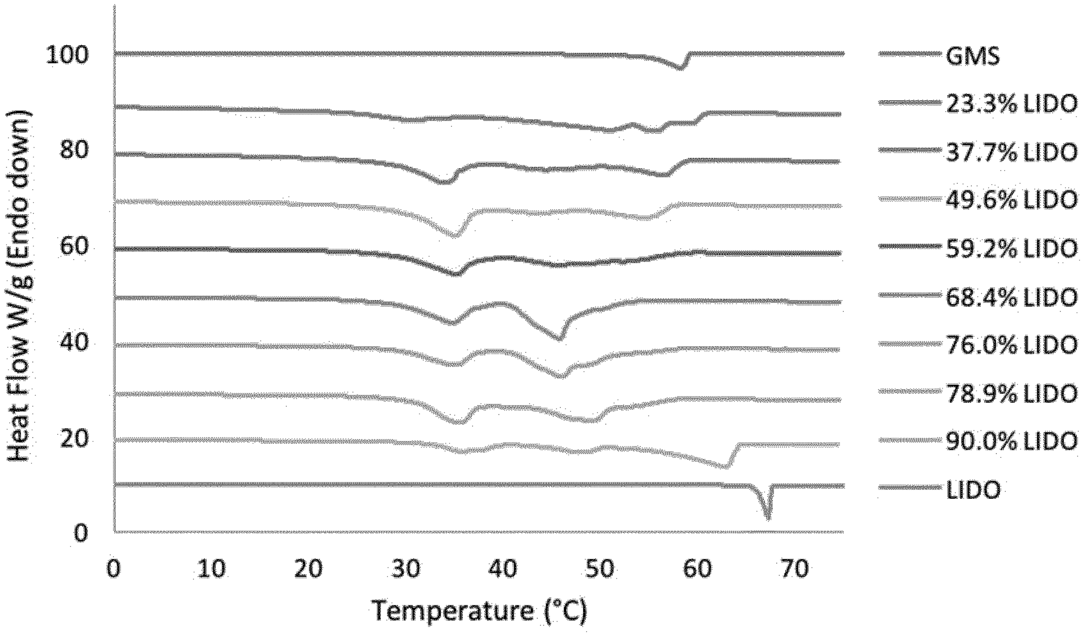
FIG. 6 is a DSC thermogram depicting the second heating cycle for the binary mixtures of lidocaine and glycerol monostearate at varying percentage moles.
Figure 7:
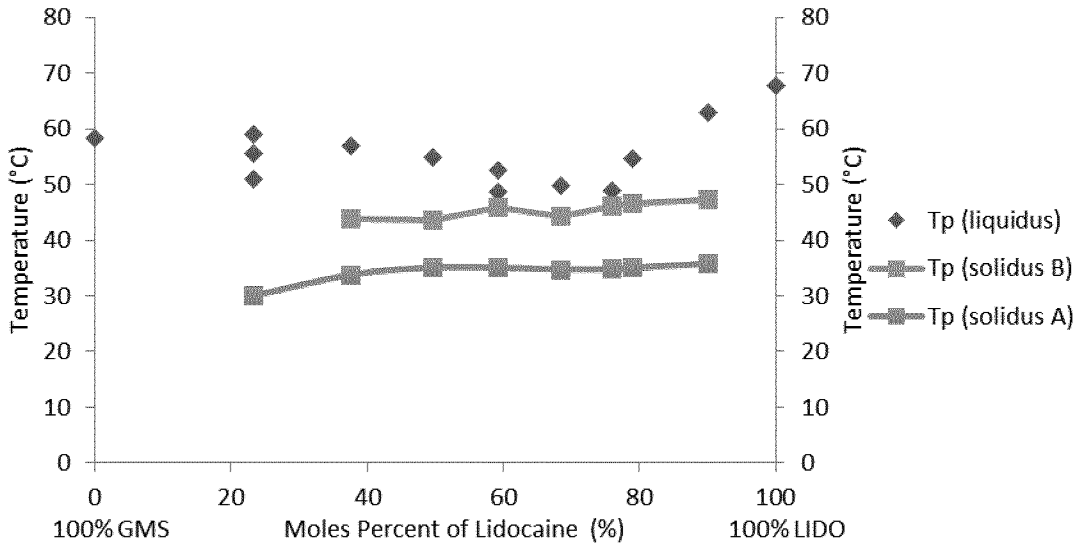
FIG. 7 is a phase diagram depicting the melting point of the binary mixtures of lidocaine and glycerol monostearate during the second heating cycle.

FIG. 6 illustrates the DSC profiles for various molar ratios of the LIDO/GMS system. The addition of GMS to the LIDO system elicits two invariant endothermic eutectic melts at approximately 34° C. and 45° C. Furthermore, a number of endothermic melts at higher temperatures were observed at all compositions. In light of the DSC plots recorded in FIG. 6, for LIDO and GMS, a phase diagram was generated (FIG. 7).

Powder X-Ray Diffraction (PXRD)

PXRD provides a tool to evaluate the solid state (crystalline or amorphous) of materials (289). This data shows that in the eutectic (preferred ratio of 1:1 lidocaine:myristic acid) there are no lidocaine crystals present.

The technique was applied to the binary systems to distinguish the physical state predominately of LIDO in the presence of the various lipids. Furthermore, PXRD provides a valuable means of determining the solid state classification of a given system.

The PXRD diffractogram for LIDO (FIG. 8) depicts sharp diffraction peaks demonstrating its existence as a crystalline solid. Significant peaks were positioned at 2θ: 10.10°, 12.48° and 24.86°. A similar diffractogram was observed when LIDO was analysed before melting (data not shown), with differences in the positions of the crystalline peaks considered negligible. Subsequently, the PXRD pattern for LIDO was ascertained when lipids were incorporated into the system at various molar ratios.

Figure 8:
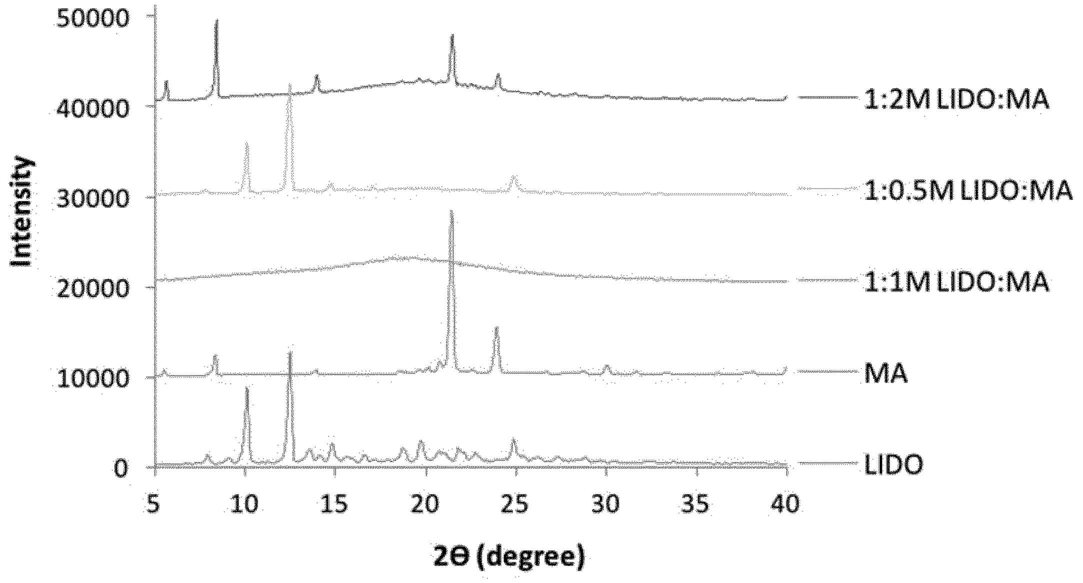
FIG. 8 is a diffractogram for the binary mixtures of lidocaine and myristic acid.

FIG. 8 depicts the crystalline nature of MA with sharp peaks detected at 2θ: 5.56°, 8.34°, 13.94°, 21.42°, 23.90° and 30.04°. In comparison, the diffractogram obtained for MA before melting displayed negligible differences (data not shown). An amorphous halo was ascertained for the 1:1M LIDO/MA binary system. It is significant to note that this system did not solidify when left for 24 hours at room temperature following melting and hence was analysed by PXRD in a liquid state. Crystalline peaks were observed for the 1:0.5M LIDO/MA system at 2θ: 10.08°, 12.46° and 24.86°. The 1:0.5M and 1:2M LIDO/MA systems were semi-crystalline in nature exhibiting an amorphous halo (albeit very slight for the 1:0.5M LIDO/MA system) corresponding to the halo evoked by the 1:1M LIDO/MA system (ara 2θ: 15-25). In addition, distinct peaks were detected at positions 2θ: 5.64°, 8.40°, 13.98°, 21.48° and 23.98°, for the 1:2M LIDO/MA formulation.

Importantly, these data show that when the eutectic is present 1:1 M Lido:MA there are no peaks due to the presence of crystals.

Figure 9:
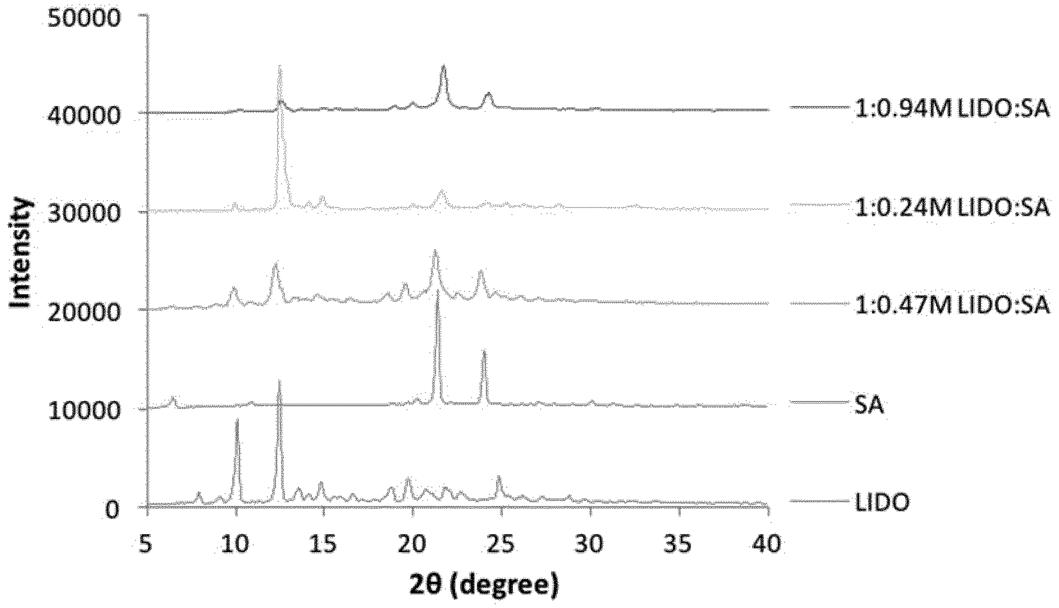
FIG. 9 is a diffractogram for the binary mixtures of lidocaine and stearic acid.

The crystalline nature of SA was demonstrated in FIG. 9, where several peaks were visible at positions 2θ: 6.50°, 10.88°, 20.26°, 21.38° and 24.00°. No significant differences were observed for the XRD profile of SA powder prior to melting (data not shown). The crystalline nature of the LIDO and SA molten binary systems was evident from the distinct peaks depicted in FIG. 9.

Peaks were identified at 2θ: 9.88°, 12.28°, 19.58°, 21.24° and 23.80°, for the 1:0.47M LIDO/SA system. The 1:0.4M LIDO/SA exhibited peaks at 26 9.94°, 12.48° and 21.58°. The crystalline character of 1:0.94M LIDO/SA was ascertained by the peaks detected at positions 2θ: 12.58°, 21.74° and 24.18°.

Figure 10:
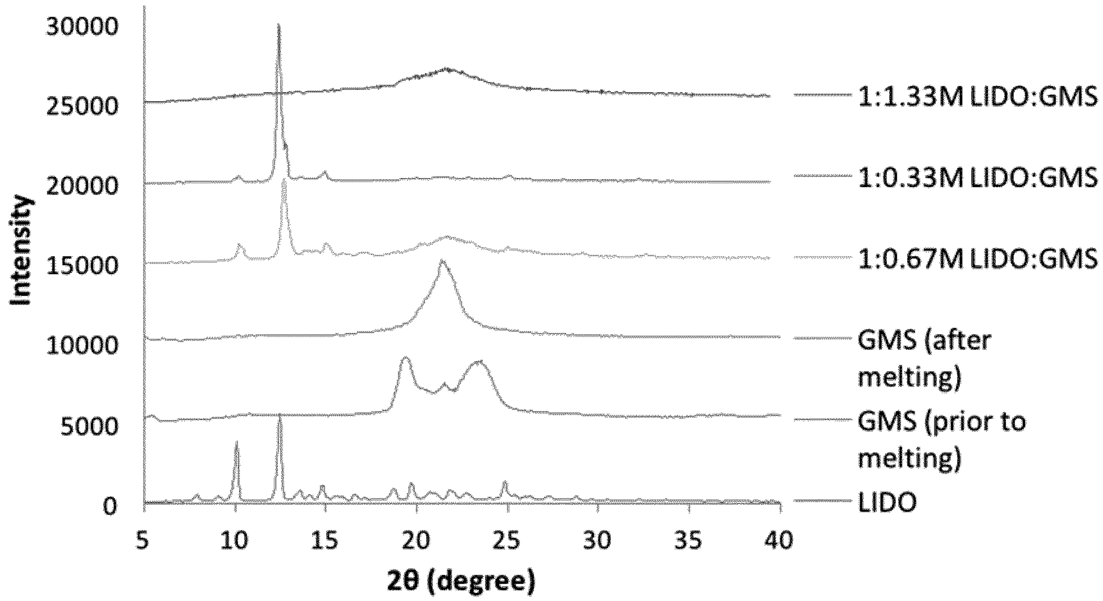
FIG. 10 is a diffractogram for the binary mixtures of lidocaine and glycerol monostearate.

Comparing the PXRD profile of GMS before and after melting reveals the polymorphic character. FIG. 10 depicts three peaks, broad in nature, associated with GMS prior to melting. The 2θ positions for said peaks were, 19.44°, 21.52° and 23.50°, and attributed to the f-form of GMS. In contrast, one broad peak at 2θ: 21.38°, was evident for the α-form of GMS analysed post melting (285). The binary molten systems of LIDO with GMS exhibited peaks indicating the crystalline nature of the combination. The 1:0.67M LIDO/GMS formulation presented peaks at 2θ: 10.26°, 12.72°, 15.1°, 21.46° and 25.06°. Distinct peaks were displayed at 2θ positions, 10.24°, 12.40°, 14.88° and 24.96°, for 1:0.33M LIDO/GMS system. The binary system of 1:1.33M LIDO/GMS provided one broad peak at 2θ, 21.44°.

Polarised Light Microscopy

PLM analysis (data not shown) of binary mixtures, and the cross sections of extrudates was consistent with the data generated by DSC and Raman mapping, showing an absence of crystallisation in the eutectic compositions, and a uniform distribution of drug across the extrudate. Crystallisation in the extrudate was absent despite the drug being present at a concentration higher than the solubility limit in non-eutectic embodiments.

2DCOS FTIR Analysis

2DCOS map of lidocaine:myristic acid mixtures showed a shift in frequency of the C═O band of myristic acid and the N—H band of lidocaine, suggesting hydrogen bonding between these functional groups. Lidocaine and myristic acid mixtures in different ratios were further evaluated. A shift in Myristic acid's C═O peak was evident when combined with lidocaine in any proportion (see Table 3).

In contrast, the shift in N—H band of lidocaine with a corresponding flattening of the N—H peak was observed only in the Lidocaine:Myristic acid 1:2 and 1:1 mixtures, suggesting that myristic acid needs to be present at either higher or at least the same molar concentration as lidocaine to engage lidocaine's N—H group completely. In the Lidocaine:Myristic acid (2:1) mixture, a significant reduction in intensity of the N—H peak was observed without band shift, possibly because N—H group of all the lidocaine molecules was not involved in hydrogen bonding.

TABLE 3

Summary of FTIR analysis

| Sample Name | v(N—H) Lidocaine | v(C═O) Lidocaine | v(C═O) Myristic acid |
|---|---|---|---|
| Lidocaine | 3254 | 1664 | — |
| Myristic acid | — | — | 1702 |
| Lidocaine:Myristic acid (2:1) | 3247.3 | 1660 | 1688 |
| Lidocaine:Myristic acid (1:1) | 3455.0* | 1663.3 | 1685.8 |
| Lidocaine:Myristic acid (1:2) | 3426.9* | 1689.7** | |

*Flattened peaks

**Lidocaine and Myristic acid C═O peaks could not be resolved

Meanwhile, the C═O of lidocaine's amide bond did not seem to be affected during the interaction between lidocaine and myristic acid.

Thermogravimetric Analysis

TGA thermal analysis was employed to establish the thermal stability of the binary systems. This is pertinent as future work will entail processing using hot melt extrusion (HME). The greatest drawback of hot melt extrusion is the risk of thermal degradation of the polymeric or lipid carrier, but the risk is especially pertinent to thermally-labile drugs.

Consequently, TGA is an essential technique used to inform the suitability of these materials and processing conditions of HME. The thermal degradation temperature was reported at 5% weight loss.

Figure 11:
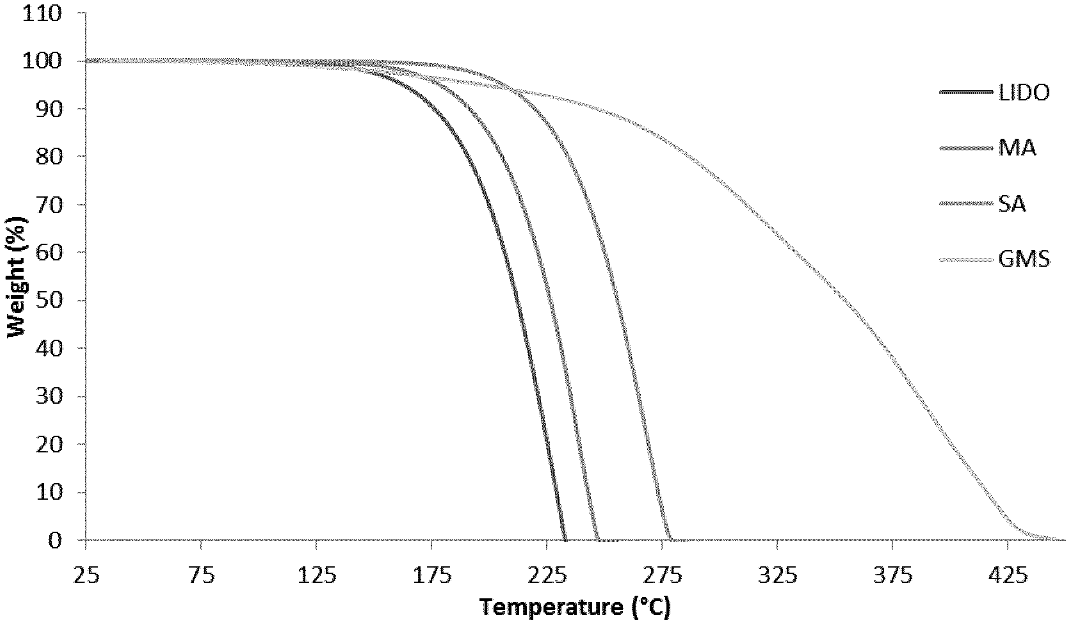
FIG. 11 is a thermogram for pure lidocaine, myristic acid, stearic acid and glycerol monostearate.

Table 4 summarises the thermal degradation temperature of the starting excipients (FIG. 11) and the LIDO/lipid systems at various molar ratios. Thermal degradation of lidocaine was observed at 164.40° C. The thermal degradation temperature was determined at 177.55° C., 201.75° C. and 197.34° C. for MA, SA and GMS, respectively. Greater aliphatic chain length elicited an increase in degradation temperature.

The 1:1M LIDO/MA system was a liquid before it was exposed to the TGA conditions, whilst the 1:2M LIDO/MA and 1:0.5M LIDO/MA combinations were semi-solids. The LIDO/SA and LIDO/GMS formulations were in the solid state when TGA was initiated. Significantly different thermal degradation temperatures were reported when comparing LIDO to: 1:1M LIDO/MA, 1:2M LIDO/MA, 1:0.94M LIDO/SA and 1:1.33M LIDO/GMS. The 1:1M LIDO/MA exhibited the highest degradation temperature of the binary systems.

The degradation temperature of lidocaine is increased when it is in the eutectic mix. Therefore it has increased thermal stability.

TABLE 4

Summary of the TGA data for the LIDO/lipid formulations.

| Formulation | Molar Ratio (Lidocaine:Lipid) | Mean Degradation Temperature ± SD (° C.) |
|---|---|---|
| LIDO | — | 164.40 ± 1.30 |
| MA | — | 177.55 ± 0.82 |

TABLE 4-continued

| Summary of the TGA data for the LIDO/lipid formulations. | | |
|---|---|---|
| Formulation | Molar Ratio (Lidocaine:Lipid) | Mean Degradation Temperature ± SD (° C.) |
| LIDO/MA | 1:1 | 176.76 ± 4.93 |
| | 1:0.5 | 171.86 ± 3.35 |
| | 1:2 | 175.79 ± 4.12 |
| SA | — | 201.75 ± 4.12 |
| LIDO/SA | 1:0.47 | 169.36 ± 1.93 |
| | 1:0.24 | 171.27 ± 3.65 |
| | 1:0.94 | 173.95 ± 0.88 |
| GMS | — | 197.34 ± 8.23 |
| LIDO/GMS | 1:0.67 | 172.87 ± 1.57 |
| | 1:0.33 | 169.29 ± 3.08 |
| | 1:1.33 | 176.03 ± 4.19 |

Results Summary

This example demonstrates the preparation and characterisation of eutectic compositions comprising one or more fatty acids and lidocaine, including compositions having improved thermal stability. The eutectic compositions prepared in this example are suitable for incorporation into polymer implants.

Example 3—Preparation and Assessment of Polymer Compositions Comprising Eutectic Compositions This example describes the assessment of polymer compositions comprising the eutectic compositions prepared in Example 2 above.

This example describes the

1. Fabrication of lidocaine-lipid-EVA hot melt extrudates;
2. Assessment of the stability of the drug loaded extrudates;
3. Characterisation of the solid state of the drug within the extrudates;
4. Determination of whether molecular interactions exist between lidocaine, lipid and EVA;
5. Determination of mechanical properties of the various systems, including to ascertain if these are influenced by formulation factors or affect drug release.

Materials and Apparatus

Materials

Glycerol monostearate, Alfa Aesar (Lancashire, UK)

Lidocaine, Swati Spentose Private Ltd (Mumbai India)

Poly(ethylene co-vinyl acetate) Ateval) 3325AC (33% VA content), Celanese (Edmonton, Alberta Canada)

Myristic acid ≥99%, Sigma-Aldrich (Dorset, UK)

Stearic acid reagent grade 95%, Sigma-Aldrich (Dorset, UK)

Apparatus

DSC Q100, Thermal Analysis Instruments (New Castle, USA)

Jasco FT/IR—4100 Fourier Transform Infrared Spectrometer (Maryland, USA)

Pike MIRacle™ ATR (Madison, USA)

RamanStation R3, Avalon Instruments (Belfast, UK)

RamanMicro 300, Raman Microscope, Perkin Elmer (Berkshire, UK)

Rigaku Miniflex II Desktop X-Ray Diffractomer (Kent, UK)

TA.XT plus Texture Analyser, Stable Microsystems (Surrey, UK)

10 mm Twin Screw Extruder Microlab, Rondol (Strasburg, France)

Methods

Hot Melt Extrusion (HME)

Fabrication of extrudates was performed on a co-rotating, intermeshing twin-screw extruder with a 2 mm cylindrical die (20:1 L/D, 10 mm Twin Screw Extruder Microlab, Rondol). Table 6 displays the formulations prepared by HME for evaluation. 10% and 20% drug loadings were investigated. To provide a thorough understanding and to aid characterisation, three molar ratios of each LIDO/lipid systems were formulated to represent: the eutectic ratio, LIDO in excess and lipid in excess.

The processing conditions are shown in Table 5. Rod shaped samples were prepared by manually mixing LIDO, lipid and the corresponding EVA carrier using a mortar and pestle before feeding the mixed sample into the hopper. Extrudates were pelletised before re-extrusion at the same conditions to produce the final product.

TABLE 5

| Hot melt extrusion processing conditions. | | | | | |
|---|---|---|---|---|---|
| Temperature (° C.) Feed Zone | Zone 1 | Zone 2 | Zone 3 | Die | Screw Speed (RPM) |
| 50 | 80 | 80 | 70 | 65 | 20 |

TABLE 6

| Formulations prepared by HME for pharmaceutical evaluation. | | | | |
|---|---|---|---|---|
| Formulation Reference | % w/w Lidocaine Loading | Lipid | LIDO:LIPID Molar Ratio | Polymer to 100% w/w |
| 10% LIDO/GMS/EVA 33% (1:0.67M) | 10 | GMS | 1:0.67 | EVA 33% |
| 10% LIDO/GMS/EVA 33% (1:0.33M) | 10 | GMS | 1:0.33 | EVA 33% |
| 10% LIDO/GMS/EVA 33% (1:1.33M) | 10 | GMS | 1:1.33 | EVA 33% |
| 20% LIDO/GMS/EVA 33% (1:0.67M) | 20 | GMS | 1:0.67 | EVA 33% |
| 20% LIDO/GMS/EVA 33% (1:0.33M) | 20 | GMS | 1:0.33 | EVA 33% |
| 20% LIDO/GMS/EVA 33% (1:1.33M) | 20 | GMS | 1:1.33 | EVA 33% |
| 10% LIDO/MA/EVA 33% (1:1M) | 10 | MA | 1:1 | EVA 33% |
| 10% LIDO/MA/EVA 33% (1:0.5M) | 10 | MA | 1:0.5 | EVA 33% |
| 10% LIDO/MA/EVA 33% (1:2M) | 10 | MA | 1:2 | EVA 33% |
| 20% LIDO/MA/EVA 33% (1:1M) | 20 | MA | 1:1 | EVA 33% |
| 20% LIDO/MA/EVA 33% (1:0.5M) | 20 | MA | 1:0.5 | EVA 33% |
| 20% LIDO/MA/EVA 33% (1:2M) | 20 | MA | 1:2 | EVA 33% |
| 10% LIDO/SA/EVA 33% (1:0.47M) | 10 | SA | 1:0.47 | EVA 33% |
| 10% LIDO/SA/EVA 33% (1:0.24M) | 10 | SA | 1:0.24 | EVA 33% |
| 10% LIDO/SA/EVA 33% (1:0.94M) | 10 | SA | 1:0.94 | EVA 33% |
| 20% LIDO/SA/EVA 33% (1:0.47M) | 20 | SA | 1:0.47 | EVA 33% |
| 20% LIDO/SA/EVA 33% (1:0.24M) | 20 | SA | 1:0.24 | EVA 33% |
| 20% LIDO/SA/EVA 33% (1:0.94M) | 20 | SA | 1:0.94 | EVA 33% |

Powder X-Ray Diffraction (PXRD) and Stability

PXRD was used to deduce the solid state form (crystalline or amorphous) of the materials. Stability studies were conducted using PXRD to ascertain the solid state form of LIDO within the various formulations. Stability testing was performed at 20° C./75% RH for 12 months. Following extrusion, samples were pelletised and subsequently stored at 20° C., 75% RH. Analysis by PXRD was performed periodically (day 0, 2 weeks, 4 weeks, then every 12 weeks, or until recrystallisation was observed) to determine the stability of LIDO within the system. The pellets were arranged in a mosaic fashion on a frosted glass slide. A 2θ scanning range of 3-40° at a scanning speed of 2°/minute was employed. The operating voltage and current applied were 30 kV and 15 mA, respectively.

Differential Scanning Calorimetry (DSC)

Thermal analysis of the extrudates was conducted after the stability studies had concluded. The heating rate required needed to be rapid enough to prevent drug solubilizing into the polymeric carrier during the DSC, whilst preserving the resolution. The latter consideration was pertinent for this system given the overlapping melting point of the drug and polymer. The samples were heated from −90° C. to 150° C., at 20° C. min-1 following instrument equilibration at −90° C.

Two-Dimensional Correlation Fourier-Transform Infrared Spectroscopy

Two-dimensional correlation Fourier-transform infrared spectroscopy (2DCOS FTIR) was performed as described above, with the following adjustments. Sample mixtures of eutectics in EVA were weighed and dissolved in dichloromethane in which the blank KBr pellets were dipped. Films were allowed to dry on the KBr pellets under laminar flow overnight and analysed in transmission mode after 24 hours. The samples were:

EVA (100%) EVA+Lido (6%)

EVA+Lido (6%)+MA (~6%, equivalent to 1:1 molar ratio to Lido)

EVA+Lido (9%) EVA+Lido (15%)

EVA+Lido (9%)+MA (~9%, equivalent to 1:1 molar ratio to Lido)

EVA+Lido (15%)+MA (~15%, equivalent to 1:1 molar ratio to Lido)

EVA+Lido (18%)+MA (~18%, equivalent to 1:1 molar ratio to Lido)

All samples were analysed in Transmission mode and data recorded. A 2D Cross correlation analysis of the five mixtures of lidocaine and myristic acid was run and the synchronous and asynchronous maps were compared with the spectra.

Raman Mapping

Raman was employed to further investigate the 20% LIDO/MA/EVA 33% (1:1M) extrudate as this formulation yielded promising stability results. Raman was performed on the excipients and solid and molten LIDO. The latter was necessary, to deduce the Raman spectrum of the amorphous form. Previous attempts at quench cooling molten LIDO under liquid nitrogen, were futile as LIDO rapidly reverted to the crystalline state. Raman mapping of the extrudate was performed using the following parameters; 0.2 mm spacing and 25 points (width and height), eliciting a map of 4.8×4.8 mm. Raman mapping was performed by comparing the correlation of the individual points on the sample map to a LIDO reference spectra. 1541-1708 cm-1 was selected as the Raman shift range for comparison because this region was void of EVA and MA peaks but contained significant LIDO Raman shift peaks. The samples were placed on aluminum foil covering a glass slide. The slide was subsequently mounted onto the Raman stage. A 785 nm laser (300 mW) was used and analysis was performed between 200 and 3200 cm-1. The exposure time and number of exposures was, 5 s and 4, respectively.

Tensile Analysis

Tensile analysis was performed to compare the tensile properties of the various formulations. In embodiments relating to pharmaceutical applications, administration requires the surgeon to retrieve the device and consequently mechanical integrity following placement in the peritoneum for 10 days is paramount. In light of this, the extrudates were also analysed following 10 days exposure to PBS. Tensile properties, namely, Young's Modulus and the tensile strength at break, were determined using the Texture Analyser. Extrudates 30 mm in length were prepared and the diameter of each sample was determined using a digital caliper (average of 5 readings). The gauge (strain height) was set at 5 mm and the sample was secured between the upper and lower clamps. The texture analyser was calibrated with a 1.0 kg load weight. A test speed of 5 mm s-1 was employed. Only the data of samples (n=5) that broke in the middle region were recorded. The Young's Modulus was calculated from the gradient of linear portion (elastic deformation) of the stress-strain curve, and the tensile strength at break was determined.

Statistics

The level of significance for the statistical analysis, was denoted at $p<0.05$ (hence, individual probability values were not quoted). Where appropriate, results were statistically evaluated using a one-way/two-way ANOVA or paired/unpaired student t-test. To determine the former test individual differences a Tukey-Kramer post hoc test was subsequently applied.

Results

Powder X-Ray Diffraction (PXRD) and Stability

Stability was determined by PXRD. Analysis by PXRD was performed periodically (up to 48 weeks) to determine the stability of LIDO within the various formulations. Stability is inferred by the LIDO remaining amorphous within an extrudate, as crystallization of LIDO yields unsuitable devices as drug loss is possible due to LIDO shearing from the surface. The results for 20% LIDO/lipid/EVA 33% are summarized in Table 7 and FIGS. 12, 13, and 14.

TABLE 7

Summary of stability results for the 20% LIDO/LIPID/EVA 33% extrudates

| Lipid | z | Formulation | Recrystallisation Observed (time) | No Recrystallisation to 48 weeks |
|---|---|---|---|---|
| — | | 20% LIDO/EVA 33% HME | ✓ Day 0 | — |
| MA | | 20% LIDO/MA/EVA 33% (1:1M) | — | ✓ |
| | | 20% LIDO/MA/EVA 33% (1:0.5M) | ✓ Day 14 | — |
| | | 20% LIDO/MA/EVA 33% (1:2M) | Not tested* | Not tested* |
| SA | | 20% LIDO/SA/EVA 33% (1:0.47M) | ✓ Day 14 | — |
| | | 20% LIDO/SA/EVA 33% (1:0.24M) | ✓ Day 0 | — |
| | | 20% LIDO/SA/EVA 33% (1:0.94M) | ✓ Day 14 | — |

TABLE 7-continued

Summary of stability results for the 20% LIDO/LIPID/EVA 33% extrudates

| Lipid | z | Formulation | Recrystallisation Observed (time) | No Recrystallisation to 48 weeks |
|---|---|---|---|---|
| GMS | | 20% LIDO/GMS/EVA 33% (1:0.67M) | ✓ Day 14 | — |
| | | 20% LIDO/GMS/EVA 33% (1:0.33M) | ✓ Day 14 | — |
| | | 20% LIDO/GMS/EVA 33% (1:1.33M) | Not tested* | Not tested* |

*Samples unable to be prepared for testing.

Figure 12:
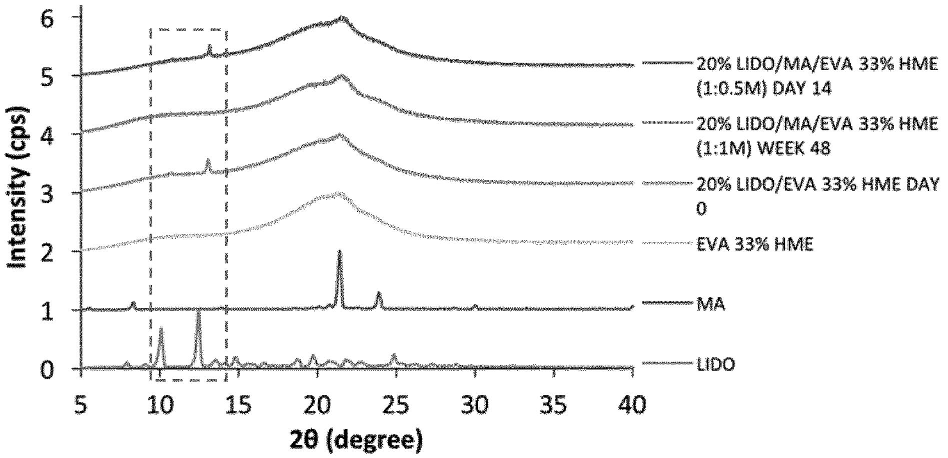
FIG. 12 is a diffractogram for the 20% LIDO/MA/EVA 33% Hot Melt Extrudates (HME). Area of interest highlighted by red dashed box.

At day 0, the 20% LIDO/EVA 33% extrudates (devoid of lipid) evoked peaks corresponding to LIDO at 2θ positions: 10.66° and 13.08° (FIG. 12). Hence, this indicates this formulation was extremely unstable eliciting crystalline LIDO immediately post-extrusion and prior to exposure of the stability conditions (20° C./75% RH).

The absence of LIDO peaks shown in FIG. 12 for the 20% LIDO/MA/EVA 33% (1:1M) formulation, signifies it remained amorphous during the 48 weeks stability testing period. In contrast, when greater LIDO was present in the 20% LIDO/MA/EVA 33% (1:0.5M) formulation, a LIDO peak at 13.18° was evident at day 14 post-extrusion. The 20% LIDO/MA/EVA 33% (1:2M) extrudates were unable to be prepared for PXRD analysis, as the high proportion of MA present in the system and extrusion processing conditions used generated a poorly formed extrudate that could not be pelletised (required form for PXRD analysis). Neither 20% LIDO/MA/EVA 33% extrudate exhibited MA peaks in the diffractogram.

Extrudates of 20% Lidocaine in EVA33% crystallised after manufacture. When 20% lidocaine was incorporated into EVA as a eutectic (1:1 lidocaine:myristic acid) then no crystallisation was observed, even at 48 weeks.

Figure 13:
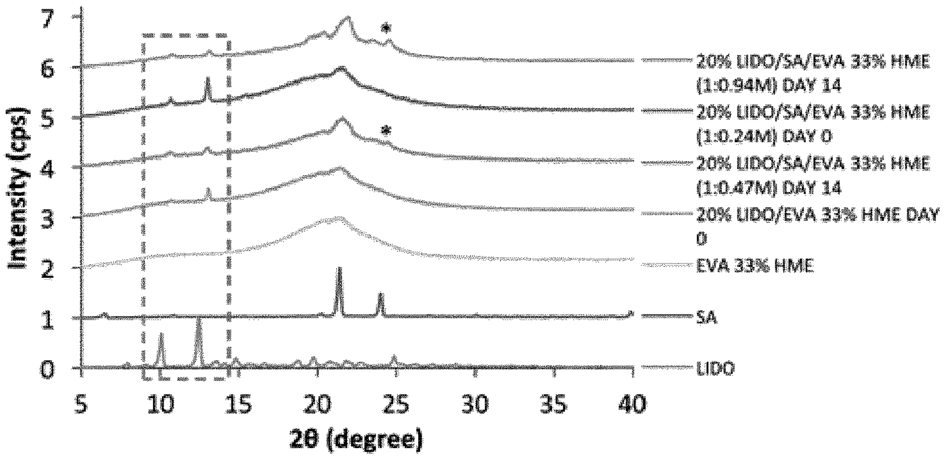
FIG. 13 is a diffractogram for the 20% LIDO/SA/EVA 33% Hot Melt Extrudates (HME). Area of interest highlighted by red dashed box. Asterisk indicates SA peaks.
Figure 14:
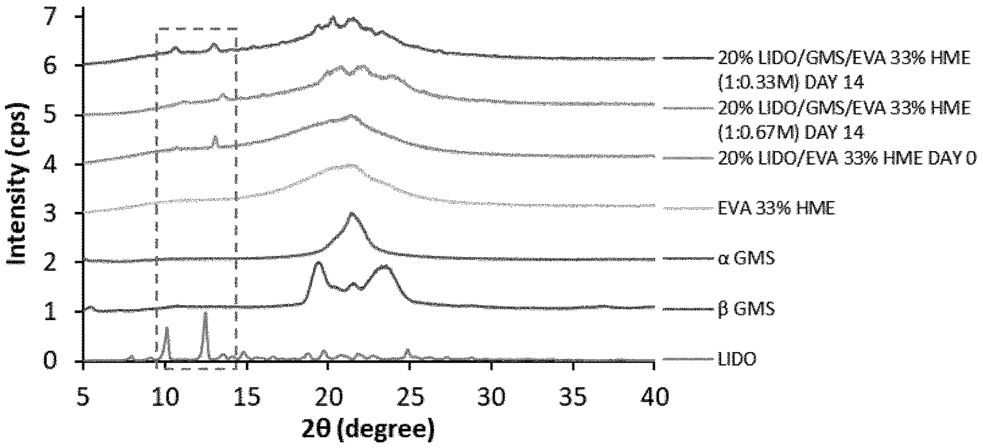
FIG. 14 is a diffractogram for the 20% LIDO/GMS/EVA 33% Hot Melt Extrudates (HME). Area of interest highlighted by red dashed box.

FIG. 13 shows LIDO peaks were observed at 2θ positions: 10.68° and 13.06°, at day 14 for the 20% LIDO/SA/EVA 33% (1:0.47M). Increasing the LIDO with respect to the SA, elicited crystallisation more rapidly. On the day of extrusion, 20% LIDO/SA/EVA 33% (1:0.24M) evoked LIDO peaks at, 10.68° and 13.04°. Peaks at 2θ: 10.78° and 13.14°, were attributed to LIDO on day 14 post-extrusion for the 20% LIDO/SA/EVA 33% (1:0.94M) extrudate. SA peaks (shown by asterisks in FIG. 13) were identified in the 20% LIDO/SA/EVA 33% 1:0.47M and 1:0.94M formulations, this finding was the same for the 10% LIDO/SA/EVA 33% 1:0.47M and 1:0.94M extrudates. In contrast, the extrudate composed of lower SA content (0.24M) exhibited no SA peaks.

On day 14 post-extrusion, LIDO peaks at; 11.08° and 13.54°, and, 10.68° and 12.90°, were respectively observed for 20% LIDO/GMS/EVA 33% (1:0.67M) and 20% LIDO/GMS/EVA 33% (1:0.33M) HME. The sharper peaks in the 20-25° range exhibited by the LIDO-rich formulation, 20% LIDO/GMS/EVA 33% (1:0.33M), are postulated to be due to crystalline LIDO.

2DCOS FTIR

Lidocaine at concentrations >10% in EVA 33% crystallises out. Since the Lidocaine-Myristic acid eutectic was more stable in EVA polymer than lidocaine alone, especially at higher concentrations, drug-polymer and eutectic-polymer interactions were also studied by 2DCOS FTIR in a concentration dependent manner.

At concentrations of up to 9% lidocaine in EVA, a shift in lidocaine's N—H peak was observed due to hydrogen bonding with EVA's carboxylic (C=O) group, causing the lidocaine molecules to assemble on an EVA backbone. However, as the lidocaine concentration exceeds beyond 9% in EVA, the C=O group in EVA is either insufficient or too closely spaced to be able to interact with N—H group of all lidocaine molecules. Consequently, the N—H peaks show reduced intensity without N—H band shift (see Table 8).

Mechanism of Crystalisation and Inhibition of Crystalisation

In the absence of any other C=O groups, the N—H of lidocaine molecules interacts with C=O of adjacent lidocaine molecules resulting in crystallization. On addition of Myristic acid, N—H group of lidocaine interacts with the C=O of Myristic acid in preference to C=O of adjacent lidocaine molecules (as suggested by the shift in N—H band and flattening of the peak in presence of myristic acid), thus preventing crystallization.

TABLE 8

Summary of FTIR analysis

| Sample Name | v(N—H) Lidocaine | v(C=O) Lidocaine | v(C=O) Myristic acid | v(C=O) EVA |
|---|---|---|---|---|
| Lidocaine | 3254 | 1664 | — | — |
| Myristic acid | — | — | 1702 | — |
| EVA | — | — | — | 1738.3 |
| EVA + Lido 6% | 3449.1* | 1691.8 | — | 1738.1 |
| EVA + Lido + MA 6% | 3450.1* | 1698.2** | | 1738.2 |
| EVA + Lido 9% | 3449.1* | 1688.7 | — | 1738.1 |
| EVA + Lido + MA 9% | 3308.0 | 1688.7** | | 1737.4 |
| EVA + Lido 15% | 3449.1/ 3306.6 | 1688.7 | — | 1737.8 |
| EVA + Lido + MA 15% | 3442.0* | 1688.7** | | 1737.9 |
| EVA + Lido 18% | 3291.0 | 1690.5 | — | 1737.7 |
| EVA + Lido + MA 18% | 3449.1* | 1685.5** | | 1737.1 |

*Flattened peaks

**Lidocaine and Myristic acid C=O peaks could not be resolved

Evaluation of Other Eutectic Mixtures

Based on the FTIR findings, interaction of the different local anaesthetics with saturated (e.g. palmitic acid and lauric acid) and unsaturated fatty acids (e.g. oleic acid) was evaluated.

Raman Mapping

Raman mapping shows that the drug is uniformly dispersed across the cross section of the extruded strand. This indicates 1) the final product is stable and did not exhibit crystallisation and 2) the manufacture process is able to uniformly mix the components. In the event of surface crystallisation, bright spots blooming on the outside of the extruded strand would be observed. If crystallisation occurred within the polymer, then a non-uniform distribution of drug would be observed. The uniform distribution of drug throughout the eutectic polymer implants described herein indicates these implants possess advantageous properties for clinical use.

Figure 15:
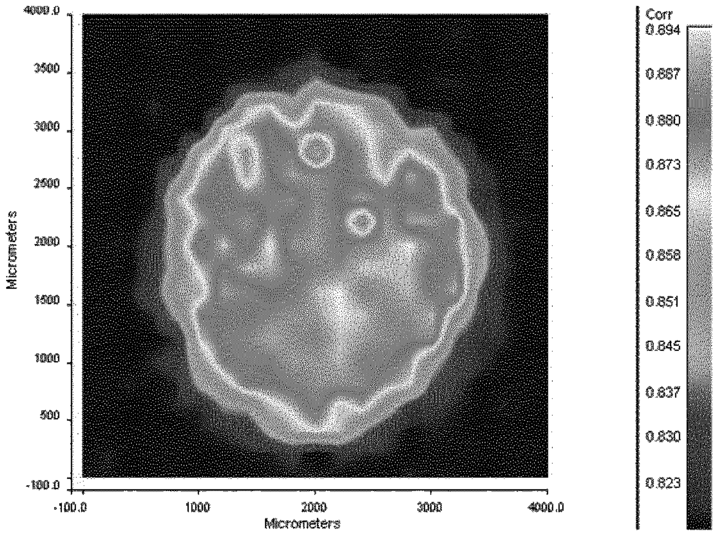
FIG. 15 shows a Raman map of LIDO containing eutectic (1:1M) within EVA 33% HME correlated to LIDO spectra.

The eutectics in EVA 33% extrudate were further evaluated by Raman mapping. The correlation between LIDO at the cross-section to a reference Raman spectra of LIDO at a range (1541-1708 cm-1) void of interfering EVA or MA peaks, but containing significant C=O LIDO peaks was used. The colours of the Raman map are correlated to a rainbow colour spectrum in the following descending intensity order red <orange <yellow <green <blue <indigo <violet <black. As clearly seen in FIG. 15, the eutectic in EVA 33% has a uniform distribution of LIDO throughout the observed cross-section. In contrast, the extrudates in which LIDO recrystallisation (no eutectic present) was evident typically exhibited Raman maps where LIDO was concentrated at the edges. Hence, the uniform distribution observed for eutectics in EVA 33% extrudate supports the PXRD, DSC and FTIR finding which indicates LIDO does not recrystallise within this system. It also shows the drug-comprising eutectic does not migrate/separate to the surface.

Tensile Analysis

Tensile analysis was performed to compare the tensile properties of the various formulations on formation, and following 10 days exposure to PBS, and these samples are referred to as 'before release', and 'after release', respectively herein.

Table 9 displays the tensile strength (TS) of the extrudates and is a measure of the maximum stress a material can withstand before rupture. A trend was observed, whereby incorporating lipid resulted in the TS decreasing. For the 10% drug loadings, no significant difference was observed between 10% LIDO/EVA 33% HME and both the 10% LIDO/SA/EVA 33% (1:0.47M) and 10% LIDO/GMS/EVA 33% (1:0.67M) extrudates. Whereas at 20% drug loading all the lipid loaded systems were significantly different compared to 20% LIDO/EVA 33% HME.

TABLE 9

Summary of the tensile properties for the investigated hot melt extrudates (HME).

| | Young's Modulus Mean ± SD (N $mm^{-2}$) | | Tensile Strength at Break Mean ± SD (N) | |
|---|---|---|---|---|
| Formulation | Before Release | After Release | Before Release | After Release |
| EVA 33% HME | 2.406 ± 0.156 | 1.491 ± 0.395 | 4.708 ± 0.939 | 4.367 ± 0.578 |
| 10% LIDO/EVA 33% HME | 1.796 ± 0.351 | 1.287 ± 0.205 | 3.540 ± 0.480 | 4.481 ± 0.538 |
| 20% LIDO/EVA 33% HME | 1.245 ± 0.399 | 0.784 ± 0.086 | 3.123 ± 0.250 | 3.561 ± 0.215 |
| 10% LIDO/MA/EVA 33% (1:1M) | 0.656 ± 0.164 | 0.669 ± 0.061 | 1.84 ± 0.330 | 5.313 ± 1.012 |
| 10% LIDO/MA/EVA 33% (1:0.5M) | 0.851 ± 0.260 | 1.018 ± 0.110 | 2.183 ± 0.241 | 5.959 ± 0.557 |
| 10% LIDO/MA/EVA 33% (1:2M) | 0.505 ± 0.079 | 0.848 ± 0.288 | 1.767 ± 0.324 | 4.835 ± 0.310 |
| 20% LIDO/MA/EVA 33% (1:1M) | 0.481 ± 0.063 | 0.774 ± 0.064 | 1.216 ± 0.137 | 2.349 ± 0.195 |
| 20% LIDO/MA/EVA 33% (1:0.5M) | 0.446 ± 0.050 | 1.012 ± 0.251 | 1.646 ± 0.107 | 2.844 ± 0.438 |
| 10% LIDO/SA/EVA 33% (1:0.47M) | 1.04 ± 0.572 | 1.017 ± 0.107 | 3.113 ± 0.193 | 4.952 ± 0.854 |
| 10% LIDO/SA/EVA 33% (1:0.24M) | 1.004 ± 0.125 | 1.095 ± 0.170 | 2.693 ± 0.281 | 3.414 ± 1.934 |
| 10% LIDO/SA/EVA 33% (1:0.94M) | 1.255 ± 0.287 | 0.909 ± 0.072 | 2.498 ± 0.173 | 4.081 ± 0.245 |
| 20% LIDO/SA/EVA 33% (1:0.47M) | 0.558 ± 0.075 | 1.024 ± 0.137 | 2.029 ± 0.301 | 2.703 ± 0.182 |
| 20% LIDO/SA/EVA 33% (1:0.24M) | 0.568 ± 0.112 | 1.493 ± 0.336 | 1.933 ± 0.990 | 3.144 ± 0.465 |
| 20% LIDO/SA/EVA 33% (1:0.94M) | 0.907 ± 0.315 | 1.275 ± 0.287 | 1.635 ± 0.253 | 2.088 ± 0.139 |
| 10% LIDO/GMS/EVA 33% (1:0.67M) | 0.767 ± 0.105 | 1.328 ± 0.326 | 2.814 ± 0.059 | 3.374 ± 0.481 |
| 10% LIDO/GMS/EVA 33% (1:0.33M) | 0.746 ± 0.26 | 1.156 ± 0.149 | 2.551 ± 0.059 | 2.984 ± 0.272 |
| 10% LIDO/GMS/EVA 33% (1:1.33M) | 0.929 ± 0.219 | 1.34 ± 0.304 | 1.561 ± 0.744 | 3.504 ± 0.301 |
| 20% LIDO/GMS/EVA 33% (1:0.67M) | 0.604 ± 0.128 | 0.998 ± 0.248 | 1.627 ± 0.147 | 3.170 ± 0.205 |
| 20% LIDO/GMS/EVA 33% (1:0.33M) | 0.742 ± 0.128 | 1.014 ± 0.191 | 2.335 ± 0.366 | 2.086 ± 0.187 |
| 20% LIDO/GMS/EVA 33% (1:1.33M) | 0.580 ± 0.240 | 1.595 ± 0.203 | 1.201 ± 0.329 | 3.412 ± 0.499 |

Exposure of the extrudates to PBS for 10 days typically elicited an increase in the TS for the systems with lipid. In contrast, to the extrudates without lipid there was no change (data not shown).

When comparing the LIDO/LIPID/EVA 33% HME systems before and after release the following elicited a significant increase in TS:

All LIDO/MA/EVA 33% HME formulations
10% LIDO/SA/EVA 33% (1:0.47M) HME
10% LIDO/SA/EVA 33% (1:0.94M) HME
10% LIDO/GMS/EVA 33% (1:1.33M) HME
20% LIDO/GMS/EVA 33% (1:0.67M) HME
20% LIDO/GMS/EVA 33% (1:0.33M) HME Preliminary stability studies (20° C./75% RH) revealed rapid recrystallisation of LIDO from all drug loadings of the LIDO/EVA 12% extruded systems and the 20% LIDO/EVA 33% formulation. This yielded unsuitable devices as drug loss was possible due to LIDO shearing from the surface. In contrast, the 5% LIDO/EVA 33% extrudates maintained LIDO in the amorphous form for the duration (48 weeks) of the stability test.

Example 4—Preparation of Co-Extrudates and Testing In Vitro and In Vivo

This example describes the co-extrusion of a polymer implant and the assessment of its performance, both in vitro and in vivo. Co-extrusion was used to achieve two layers of EVA with different VA percentages and different properties. The outer shell contained the drug-comprising eutectic, and the inner core gave greater tensile strength and in some cases was radio-opaque for ease of monitoring and recovery.

Briefly, this example describes 1. the fabrication and characterization of a lidocaine loaded co-extrudate;
2. the assessment of the drug content uniformity;
3. the determination and mathematical modelling of in vitro drug release;
4. the determination of mechanical properties of the systems and of drug release (in vitro and in vivo);
5. Release of lidocaine from the melt extrudate in PBS and peritoneal fluid; and
6. an in vivo study in an animal model to ascertain the release, safety and tensile properties of the lidocaine loaded co-extrudate.

Methods

Hot Melt Extrusion (HME) Fabrication (Monolayer)

Fabrication of 20% w/w $BaSO_4$/EVA 12% HME (monolayer) was performed on a co-rotating, intermeshing twinscrew extruder with a 2 mm cylindrical die (20:1 L/D, 10 mm Twin Screw Extruder Microlab). The processing conditions are shown in Table 10. Rod shaped samples were prepared by manually mixing $BaSO_4$ and the EVA carrier using a mortar and pestle before feeding the mixture into the hopper. Extrudates were pelletised before re-extrusion at the same conditions to produce the final product.

TABLE 10

Hot melt extrusion processing conditions.

| Parameter | Extruder Zone Feed Zone | Zone 1 | Zone 2 | Zone 3 | Die | Screw Speed (RPM) |
|---|---|---|---|---|---|---|
| Temperature (° C.) | 50 | 80 | 80 | 70 | 65 | 20 |
| Screw Design | 5 × Convey | 2 × Convey<br>2 × 60°<br>1 × 90° | 5 × Convey | 1 × 60°<br>1 × 90°<br>2 × Convey | — | — |

Co-Extrusion Fabrication (Bilayer)

Figure 16:
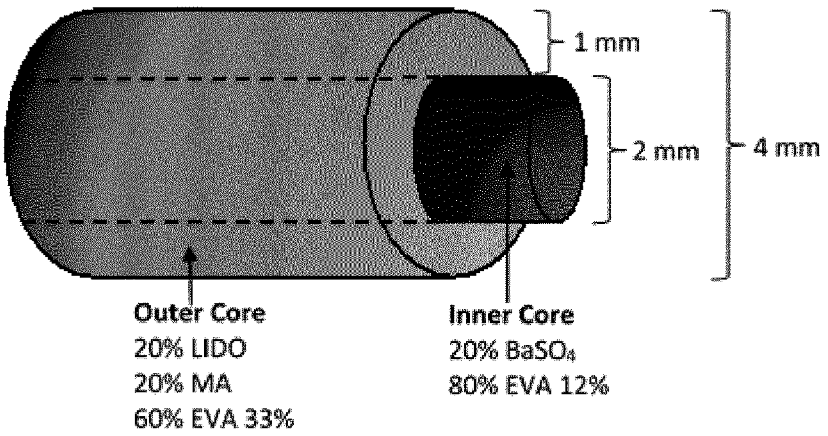
FIG. 16 is a diagram with dimensions of a LIDO loaded co-extrudate.

Co-extrusion of the bilayer spherical rod, as shown in FIG. 16, was prepared. The materials for the inner core were initially compounded before co-extrusion (described herein).

Compounding

Compounding was performed on a Dr Collin ZK 25 twinscrew extruder, with co-rotating, intermeshing 25 mm diameter screws with a 30:1 L/D. The extruder was attached to a Dr Collin, air cooled die face pelletising system. The compounding processing temperatures/conditions for the inner core are shown in Table 11. The outer core could not be compounded due to the low viscosity and stickiness of the materials rendering it impossible to produce a valid pellet. Hence, the outer core compounds were extruded directly to product (bilayer co-extrudate).

TABLE 11

Compounding processing conditions of the inner core.

| Core | Temperature (° C.) Feed Zone | Zone 1 | Zone 2 | Zone 3 | Zone 4 | Zone 5 | Die | Screw Speed (RPM) | Output (kg $h^{-1}$) |
|---|---|---|---|---|---|---|---|---|---|
| Inner | 75 | 95 | 100 | 100 | 100 | 95 | 100 | 90 | 1.6 |

Bilayer Co-Extrudate

The desired dimensions for the co-extrudate were an inner core diameter of 2.0 mm and outer layer thickness of 1.0 mm, to give a total diameter of 4.0 mm. FIG. 16 shows the dimensions and the composition of the layers. A blank co-extrudate was also fabricated with the outer layer composed solely of EVA 33%, whilst the inner core was unchanged (20% BaSO4 and 80% EVA 12%). The bilayer strand was produced using a modified over coating cross head die with the inside strand fed from a Killion 25 mm single screw extruder and the outer layer fed from a Dr Collin ZK 25 twin screw extruder. The strand was cooled in the short water cooling section of the Dr Collin tube line with the die in the horizontal position. Vertical extrusion was attempted to improve the layer ratio, however, no major improvements were observed. The processing conditions are shown in Table 12 and images of the setup are displayed in FIG. 5.4. In addition to the drug loaded co-extrudates blank co-exrudates were prepared with the eutectic absent from the outer layer.

TABLE 12

Inner core (Killion 25 mm single screw extruder) and outer shell (Dr Collin ZK 25 twin screw extruder) processing conditions for the bilayer co-extrudate.

| | Temperature (° C.) | | | | | | | Screw | |
|---|---|---|---|---|---|---|---|---|---|
| | Feed Zone | Zone 1 | Zone 2 | Zone 3 | Zone 4 | Zone 5 | Die | Speed (RPM) | Pressure (PSI) |
| Inner core 20% $BaSO_4$ and 80% EVA 12% VA | 80 | 100 | 115 | 110 | 100 | 95 | 90 | 6 | 820 |
| Outer shell (no drug)100% EVA 33% | 70 | 90 | 90 | 90 | 90 | 90 | 90 | 70 | 60 |
| Outer shell (eutectic) 20% lidocaine ~20% myrisitic acid and 60% EVA 33% | 45 | 65 | 65 | 65 | 65 | 65 | 90 | 70 | 0 |

Co-Extrudate Dimensions and Theoretical Drug Loading

Co-extrudate samples were visualised using a Leica light microscope and LAS EZ software was employed to determine the dimensions. For each sample (n=3), four measurements were recorded for the inner core diameter and the outer layer width. Subsequently, the mean values for these measurements were used to calculate the total diameter.

LIDO was only present in the outer layer and the theoretical drug loading of the co-extrudate was calculated by weighing 1 cm samples of co-extrudate (n=3). The volume of the inner core for 1 cm length of the coextrudate was calculated from the radius of the core. Assuming a density of 1 g cm-3 the theoretical weight of the outer layer was calculated by subtracting the theoretical weight of the inner core from the actual weight of the total co-extrudate. Subsequently the theoretical drug loading of a 20% w/w LIDO loaded co-extrudate was determined.

Raman Mapping

Raman mapping of the co-extrudate was performed to deduce the distribution of the LIDO in the core and outer layer using the following parameters; 0.2 mm spacing and 25 points (width and height), eliciting a map of 4.8×4.8 mm. Raman mapping was performed by comparing the correlation of the individual points on the sample map to a LIDO reference spectra. 1541-1708 cm-1 was selected as the Raman shift range for comparison because this region was void of EVA peaks but contained significant LIDO Raman shift peaks. The samples were placed on aluminum foil covering a glass slide. The slide was subsequently mounted into the Raman stage. A 785 nm laser (300 mW) was used and analysis was performed between 200 and 3200 cm-C. The exposure time and number of exposures was, 5 s and 4, respectively.

High Performance quid Chromatography (HPLC)

An HPLC assay was performed using the conditions outlined in Table 13. Three LIDO stock solutions of 100 μg mL-1 were prepared in the mobile phase and diluted to a multitude of concentrations. A calibration curve was plotted (area vs concentration) and linear regression analysis applied. The assay method was validated as per the ICH guideline on the validation of analytical procedures Q2(R1). The inter-day and intra-day precision, and intra-day accuracy was established using a minimum of 9 determinations over a minimum of 3 concentration levels covered the specified range. The limit of detection (LoD) and limit of quantification (LoQ) were determined by applying Equation 5.11 and 5.12, respectively.

TABLE 13

HPLC lidocaine assay conditions.

| Parameter | Condition |
|---|---|
| Column | Poroshell 120, EC-C18, 4.6 × 150 mm, 4 μm Guard: Poroshell 120, UHPLC Grd, EC-C18, 4.6 mm, 4 μm |
| Flow Rate | 1 ml $min^{-1}$ |
| UV Detection | 230 nm |
| Column and Injector Temperature | 25° C. |
| Injection Volume | 20 μL |
| Mobile Phase | Potassium Dihydrogen Phosphate buffer (pH 5.5, 20 mM): Acetonitrile [70:30] |
| Retention Time | ~4.5 min |

$$LoD = \frac{3.3\sigma}{s}. \quad \text{Equation 5.11}$$

$$LoQ = \frac{10\sigma}{s}. \quad \text{Equation 5.12}$$

Where,

σ=standard deviation of the response

S=slope of the calibration curve

Drug Content Uniformity

Drug content uniformity evaluates the consistency of the extruded preparation. Within a batch, segments of the extrudate should contain LIDO within a narrow range. To establish the drug content uniformity LIDO was extracted from the sample.

Three samples (~50 mg) were taken from evenly separated locations from the extruded samples. To dissolve the EVA 33% and LIDO, the samples were added to 50 mL of dichloromethane (DCM) and sonicated for 40 min. Subsequently 1 mL of the resulting solution was withdrawn and added to a volumetric flask to evaporate the DCM by exposure to 60° C. for 60 min. To dissolve the LIDO from the resulting drug film, 10 mL of methanol was added and sonicated for 30 min. The methanolic solutions containing LIDO were decanted to remove the insoluble EVA 33%. The resultant solution was quantified for LIDO using HPLC.

In vitro Drug Release

The effect of the following parameters on drug release was investigated:

1. EVA grade
2. Drug loading

3. Lipid incorporation
4. Fabrication as a co-extrudate

Figure 17:
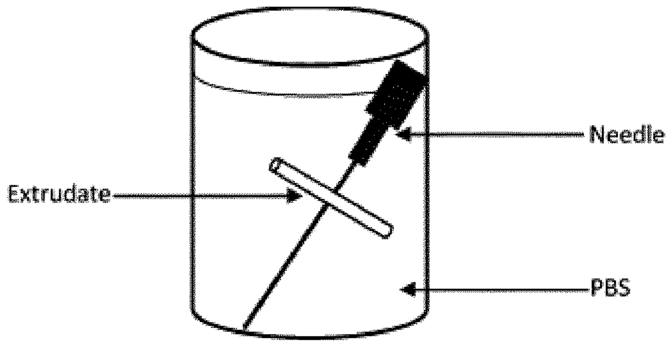
FIG. 17 is a diagrammatic representation of the in vitro drug release experimental set-up.

Samples of the extrudates, 2 cm in length, were weighted with a needle (FIG. 17) and placed in a sealed glass vial containing 45 ml of PBS (pH 7.4). The samples were incubated at 37° C. and 40 RPM. At predetermined time points the media was removed and replaced with 45 mL of fresh media. Sink conditions were maintained throughout the duration of the drug release study. This was achieved by ensuring the volume of PBS was at least 10 times the saturation volume required to dissolve the amount of LIDO released at each time point. The samples were filtered using a Millex-GS 0.22 μm and quantification of lidocaine was achieved by HPLC.

Release of Lidocaine from the Melt Extrudate

Release of lidocaine from melt extrudate containing 20% lidocaine, 20% myristic acid and 60% EVA (33% VA), under (a) sink and (b) non-sink conditions was tested both in PBS and PF media containing 6 mM of sodium azide. Falcon tubes containing melt extrudate with PF and PBS were sealed with a cap and agitated at 40 oscillations per minute in a water bath maintained at 37° C. Samples were withdrawn at pre-determined time intervals and centrifuged. The supernatant was extracted before analysis by HPLC as described above.

The release study was conducted under both sink and non-sink conditions. For sink conditions, the final concentration of lidocaine in the medium remained below 10% of the saturated solubility (0.4 mg/mL) if all the lidocaine from the melt extrudate was released, whereas for non-sink condition it would reach over 40% of saturated solubility (2.1 mg/mL) when all lidocaine was released. Approximately 40 mg and 200 mg of the melt extrudate were used for the release test under sink and non-sink conditions, respectively.

In Vivo Sheep Study

In vivo studies were performed in a sheep animal model following ethical approval (Protocol number: 1657). Sheep were selected as the model for humans due to their body size. This facilitated the administration of the same amount of extrudate to be implanted as anticipated for humans. Moreover, the use of sheep permitted multiple blood samplings. The data generated from this in vivo study has direct relevance to human clinical utility, hence the specific objectives of the animal study were to ensure drug is released as was predicted from the in vitro study, and to investigate any potential local and/or system toxicity.

This example includes a brief overview of results of an in vitro in vivo correlation (IVIVC). The fabrication of the co-extrudates used for the study and the subsequent tensile analysis was conducted as described above.

A total of 11 sheep were used in this study. The animals were divided into 3 groups, in which 5 sheep received the drug loaded implant for 7 days, 3 sheep received the blank implant for 7 days, while a further 3 sheep received drug loaded implants for 3 days. (Table 14). Each group had 4×40 cm implants placed in the abdominal cavity. Group 3 was necessary following preliminary results showing greater inflammation and adhesions from the drug loaded extrudates (Group 1) compared to Group 2 at day 7. Consequently, Group 3 facilitated the histological examination of tissues at day 3 as the device would still be clinically attractive if administration was restricted to 3 days. Moreover, lidocaine release data up to day 3 from Group 1 was applicable to Group 3, increasing the sample size to 8.

TABLE 14

In vivo study group descriptions.

| Group | Number of sheep | Extrudate Type | Length of Implantation (days) |
|---|---|---|---|
| 1 | 5 | Drug loaded | 7 |
| 2 | 3 | Blank | 7 |
| 3 | 3 | Drug loaded | 3 |

In all sheep a silicone drain was implanted to facilitate sampling of peritoneal fluid and as a comparator implanted material. A midline incision was made using scalpel for skin and diathermy for deeper layers. Upon entering the peritoneal cavity a jejunal segment of small bowel was identified for resection. A small mesenteric resection was made along with a 5 cm segment of small bowel. The mesentery was ligated using a 2-0 silk. The small bowel ends were spatulated and inspected for adequate blood supply. Hand sewn continuous end to end anastomosis was performed with 3-0 PDS. The anastomosis was then inspected for any defects and leak tested using the small bowel content. Any defects notes were secured using a single interrupted 3-0 PDS. The mesenteric defect was closed using the same PDS suture in a loose continuous fashion. The bowel was then returned and orientation was corrected as much as possible.

A 15 French silicone fluted Blake drain was placed left lateral side of the sheep spigotted. A second tract was created parallel to the Blake drain for the implant. One length of the implant (40 cm) was passed through this tract and protruded for 5 mm from the surface of the skin. 2-0 Silk was used to secure both the drain and implant. Three more lengths of the implant were then placed inside the peritoneal cavity and fixed to the peritoneum right lateral of the laparotomy wound. The fascia was then closed with heavy linen suture followed by the skin with 3-0 silk.

The neck was prepped and draped in a sterile manner with iodine in preparation for line insertion. The catheter was prepared using heparinized saline. A central venous catheter was then placed into the left internal jugular using Seldinger technique. The line was secured using 3-0 silk.

The sheep were transferred to pens when they were able to hold their heads up unassisted.

Blood samples were obtained postoperatively at 1 hr, 2 hrs, 4 hrs, 6 hrs, day 1, day 2, day 3, day 5 and day 7 for the first 8 procedures using the central venous line. The line was locked with heparinized saline after each use. Peritoneal samples were also obtained at the same time points from the abdominal drain for as long as the drain was patent. The drain was spigotted after each use. For the final 3 sheep blood samples and peritoneal samples were obtained at 1 h, 2 h, 4 h, 6 h, day 1, day 2 and day 3.

Samples were centrifuged (5844 g for 10 min) to remove cells and debris, and subsequently, plasma and peritoneal fluid was collected and stored at −20° C. for LIDO quantification. The stability of LIDO in plasma has been demonstrated in the literature. Extraction of LIDO from the biological samples was performed by adding 800 μL of acetonitrile and 100 μL of water to 100 μL of the sample to precipitate the proteins. The resulting solutions were vortexed and allowed to stand overnight before centrifuging them at 5844 g for 10 min. Subsequently, the supernatant was withdrawn and analysed by HPLC.

The sheep were euthanised on day 3 or 7 of the study, dependent on the study group. The implant was removed by gentle pulling on the exteriorized piece of implant. The peritoneal cavity was opened during a post-mortem to recover tissues from sites close to the implant and the histology examined by New Zealand Veterinary Pathology, Auckland. The recovered implants were also evaluated for their tensile properties, including their Young's Modulus and tensile strength, as outlined below.

Pharmacokinetic Analysis

Two and three compartment models, parameterised in terms of absorption half time (Tabs), clearance (CL/F), volume of distribution (V/F) and assuming first order elimination from the central compartment, were investigated. A variety of absorption profiles from the insert into the peritoneal space were tested, including a single short bolus, zero order and first order absorption profiles, and dual absorption processes (combinations of the above). The duration of zero and first order absorption profiles was assumed to be over the duration of the study (168 h). Theory based allometric scaling was used to scale parameter estimates for size using body weight. Population parameter variability was described using exponential models, which is equivalent to assuming a log-normal distribution and avoids biologically inappropriate parameter values of zero or less. Additive and proportional error models were used to describe unknown PK residual error.

Data were analysed using nonlinear mixed effects models (NONMEM 7.4, Globomax LLC, Hanover, MD, USA). First order conditional estimation method with interaction, using ADVAN=13 with TOL=6 was used. Convergence criterion was three significant digits. Model selection required a statistically significant improvement in the NONMEM objective function between nested models, equating to a reduction >3.84 based on a chi-square distribution with one degree of freedom, and inspection of standard goodness of fit. Non-parametric bootstrap methods, with 1000 simulations, were used to estimate confidence intervals as a measure of parameter uncertainty. A prediction corrected visual predicted check was used to visualise prediction intervals superimposed on observed data to evaluate how well the model predicted the distribution of observations (using 1000 simulation replicates).

Lidocaine and Myristic Acid Remaining Post-Implantation

Lidocaine and Myristic acid remaining in the co-extrudate samples recovered after implantation for 3 or 7 days in sheep was determined by LCMS-MS. The sample preparation method was similar to that used for determining uniformity of drug content. Three 1±0.2 cm sections of the implant were taken from each sheep taking care to avoid the regions tied with sutures. The components of the outer coating were dissolved by sonication in dicholoromethane and the volume was then made up to 50 ml. Two ml of this solution was dried for 1 h at 50° C. and reconstituted in 100 ml methanol. The methanolic solutions were appropriately diluted in the mobile phase for assay by LCMS-MS. Nitrolidocaine and lauric acid were used as the internal standard for assay of lidocaine and myristic acid, respectively.

Histopathology

Sheep were euthanized after 3 or 7 days post-implantation and the perioneal cavity was opened to recover tissues from the implant and drain site. The recovered peritoneal tissue was stained with haematoxylin and histopathological images were observed by two independent masked observers. The extent of inflammation in tissue and granulation tissue and fibrosis at implant and drain site in each sheep was graded as described in Table 15.

TABLE 15

Histopathaloigcal grading criteria for inflammation, granulation and fibrosis

| Score | Inflammation | Granulation and Fibrosis |
|---|---|---|
| 0 | No inflammatory cells | No granulation tissue |
| 1 | Restricted to surface of tract | restricted to surface of tract |
| 2 | extension into muscle | radiating to dermis |
| 3 | fat infiltration | radiating to muscle |
| 4 | — | extension to fat |

Evaluation of the Implants Pre and Post-Surgery

Implants were evaluated for tensile properties, remaining lidocaine and surface morphology before and after surgery.

Tensile Analysis

Tensile analysis investigated the tensile properties of the 20% Barium/EVA 12% extrudate and the co-extrude (blank and drug loaded. The pharmaceutical application requires the surgeon to retrieve the device and consequently mechanical integrity following placement in the peritoneum for 10 days is paramount. In light of this, the extrudates were also analysed following 10 days exposure to PBS. Furthermore, the co-extrudates used in the in vivo study were examined after implantation in the sheep for 7 days and 3 days, for 1 and 3, respectively.

Tensile properties, namely, Young's modulus and the tensile strength at break, were determined using the Texture Analyser. Extrudates 30 mm in length were prepared and the diameter of each sample was determined using digital calipers (average of 5 readings). The gauge (strain height) was set at 5 mm and the sample was secured between the upper and lower clamps. The texture analyser was calibrated with a 1.0 kg load weight. A test speed of 5 mm s-1 was employed. Only the data of samples (n=5) that broke in the middle region were recorded. The Young's modulus was calculated from the gradient of linear portion (elastic deformation) of the stress-strain curve. The tensile strength at break was determined using established methods.

Results

Co-Extrudate Dimensions and Drug Loading

TABLE 16

Summary of the dimensions of the LIDO loaded and blank co-extrudates

| Sample | Inner Core Diameter Mean ± SD (mm) | Outer Layer Thickness Mean ± SD (mm) | Calculated Total Diameter (mm) |
|---|---|---|---|
| LIDO loaded Co-extrudate | 2.05 ± 0.02 | 0.71 ± 0.04 | 3.47 |
| Blank Co-extrudate | 1.85 ± 0.04 | 1.03 ± 0.15 | 3.90 |

Figure 18A:
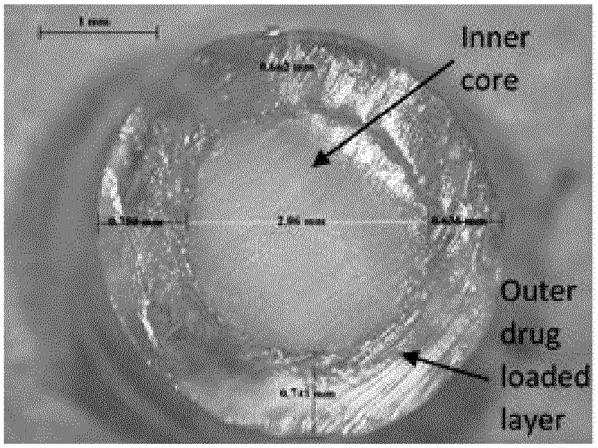
FIG. 18 shows light microscope co-extrudate images with dimensions A) LIDO loaded co-extrudate. Inner core: 20% BaSO4/EVA 12%. Outer layer: 20% LIDO/MA/EVA 33% (1:1M) and B) Blank co-extrudate. Inner core: 20% BaSO4/EVA 12%. Outer layer: EVA 33%.
Figure 18B:
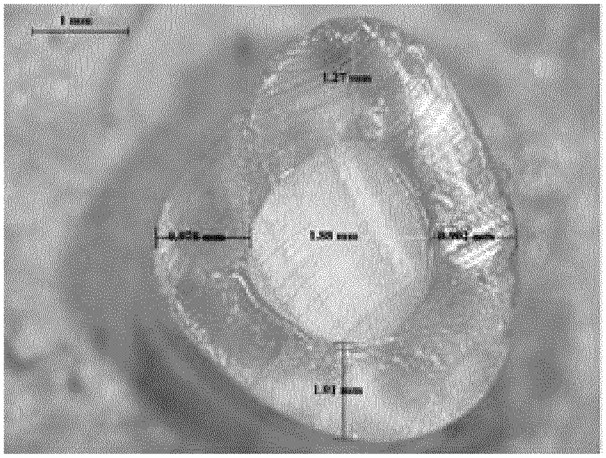

FIG. 18 illustrates the colourless outer LIDO loaded layer and the white hue in the inner core due to the presence of BaSO4. The desired dimensions of the final product was an inner core diameter of 2.0 mm and outer layer thickness of 1.0 mm, to give a total diameter of 4.0 mm (as shown in FIG. 16). Table 16 summarises the mean dimensions of the drug loaded and blank co-extrudates. The inner core of the LIDO loaded co-extrudate was close to the target diameter at 2.05 mm, and the outer layer thickness was ~0.70 mm resulting in a smaller total diameter of 3.47 mm. The blank co-extrudate inner core had a slightly smaller diameter (1.85 mm), whilst the outer layer was 1.06 mm, providing a total diameter of 3.90 mm.

The dimensions of the core and shell, which define the overall dimensions, can be modified through the manufacture process. This can be used to alter the total drug loading of the co-extruded strand, the tensile properties and the release profile. Co-extrudates with different layers, a different number of layers, or a different arrangement of layers, for example to further modify properties, are contemplated for future study. For example, a third layer could be added over the top to reduce drug release rates.

Drug Loading

The total mass of the drug loaded extrudate was 0.114 g per cm of co-extrudate (mean, n=3). The volume of the inner core was 0.033 cm3 per cm of co-extrudate, giving a theoretical mass of drug eluting outer layer (assuming density of 1 g cm-3) of 0.805 g per cm of co-extrudate. At 20% w/w drug loading in the outer shell this yields 16.106 mg LIDO per cm of co-extrudate, with a drug loading per total mass of coextrudate of 14.1% w/w.

Drug content uniformity was calculated using an extraction method. The percentage theoretical LIDO recovered is expressed in relation to the expected drug loading, as determined from 3 samples positioned at different locations along the co-extrudate. The % theoretical LIDO loading was 103.4%±6.6%, indicating reasonable consistent loading along the co-extrudate. Myristic acid loading was lower with more variation, 79.5%±13.0% of the theoretical loading achieved.

Raman Mapping

Figure 19A:
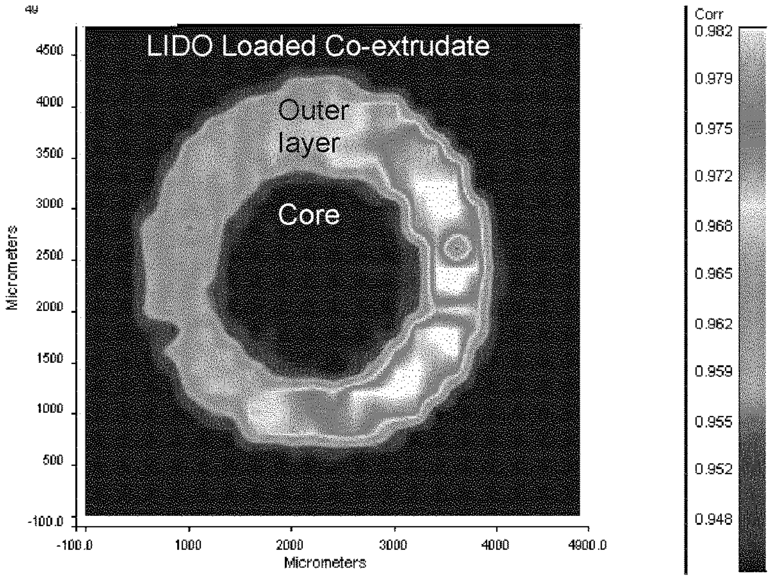
FIG. 19A shows a Raman map of LIDO loaded co-extrudate. Inner core: 20% BaSO4/EVA 12%. Outer layer: 20% LIDO/MA/EVA 33% (1:1M). Correlated to LIDO spectra.
Figure 19B:
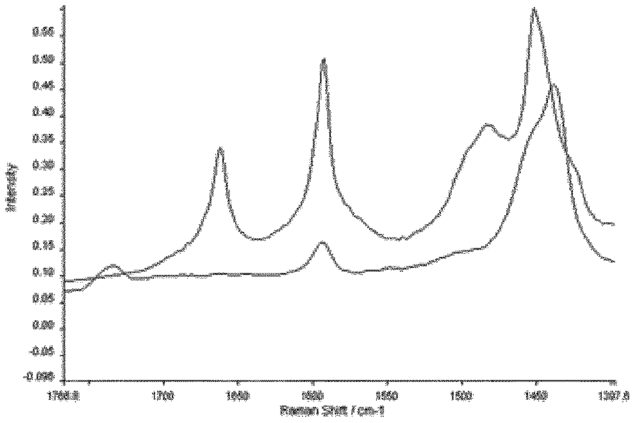
FIG. 19B shows Black spectra: Raman spectra at outer layer. Blue spectra: LIDO.
Figure 19C:
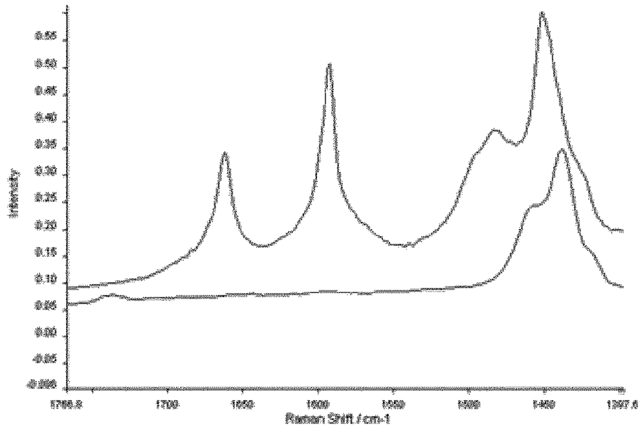
FIG. 19C shows Black spectra: Raman spectra at inner core. Blue spectra: LIDO.

Raman mapping was employed to ascertain the distribution of LIDO within the co-extrudate and to deduce if any migration had occurred during manufacture. FIG. 19, illustrates that in the outer layer there was an exceptionally high correlation with LIDO. Significantly no LIDO was found in the inner core demonstrating no migration of the drug. Furthermore, within the outer layer drug distribution is fairly even with minor distribution differences observed. The drug does not accumulate at the circumference of the co-extrudate, which is associated with poor stability.

Tensile Analysis

Tensile analysis was performed to compare the tensile properties of the various formulations. The pharmaceutical application requires the surgeon to retrieve the device and consequently mechanical integrity following placement in the peritoneum for 10 days is paramount. In light of this, the extrudates were also analysed following 10 days exposure to PBS and these samples are referred to as 'after release' herein.

Figure 20:
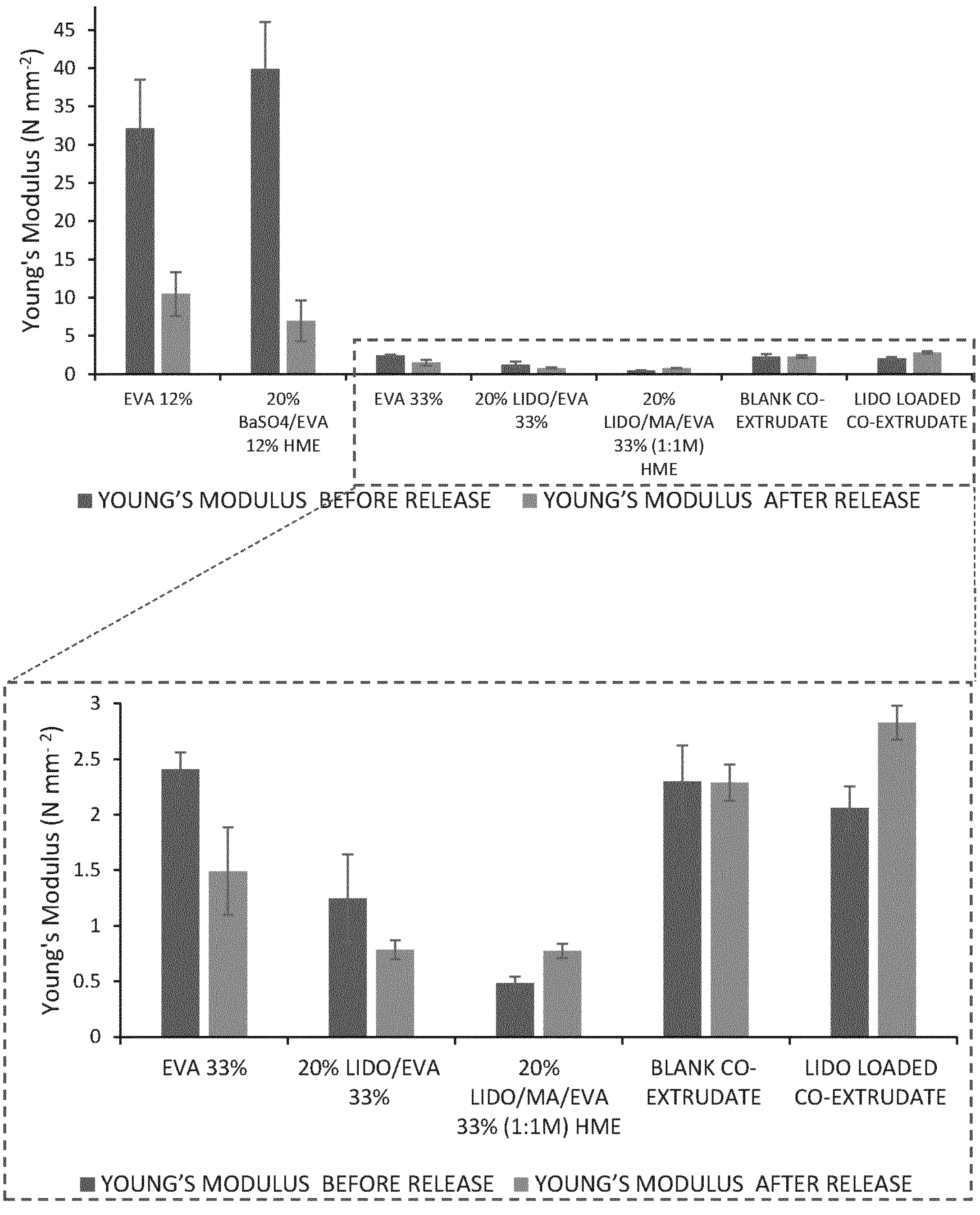
FIG. 20 shows Young's modulus for the investigated hot melt extrudates (HME) before and after release. Bottom image provides an enhanced view of selected extrudates

FIG. 20 displays the experimentally determined results for the Young's modulus (YM); a measure of a materials stiffness. Evaluating the extrudates before exposure to PBS indicated EVA 12% HME and 20% $BaSO_4$/EVA 12% HME elicited a significantly greater Young's modulus compared to the other formulations. Indeed, 20% $BaSO_4$/EVA 12% HME resulted in the most rigid extrudate with a YM of 39.924 N $mm^{-2}$. Comparing the individual extrudates before and after release resulted in significantly different YM for the following extrudates:

EVA 12% HME

20% $BaSO_4$/EVA 12% HME

EVA 33% HME

20% LIDO/MA/EVA 33% (1:1M) HME

LIDO loaded co-extrudate

Interestingly, the only increase in YM after release was for the 20% LIDO/MA/EVA 33% (1:1M) HME and the LIDO loaded co-extrudate, however, the increase was very small. Most noteworthy was the significant improvement in stiffness of the LIDO co-extrudate compared to the 20% LIDO/MA/EVA 33% (1:1M) HME monolayer, both before and after exposure to PBS.

Figure 21:
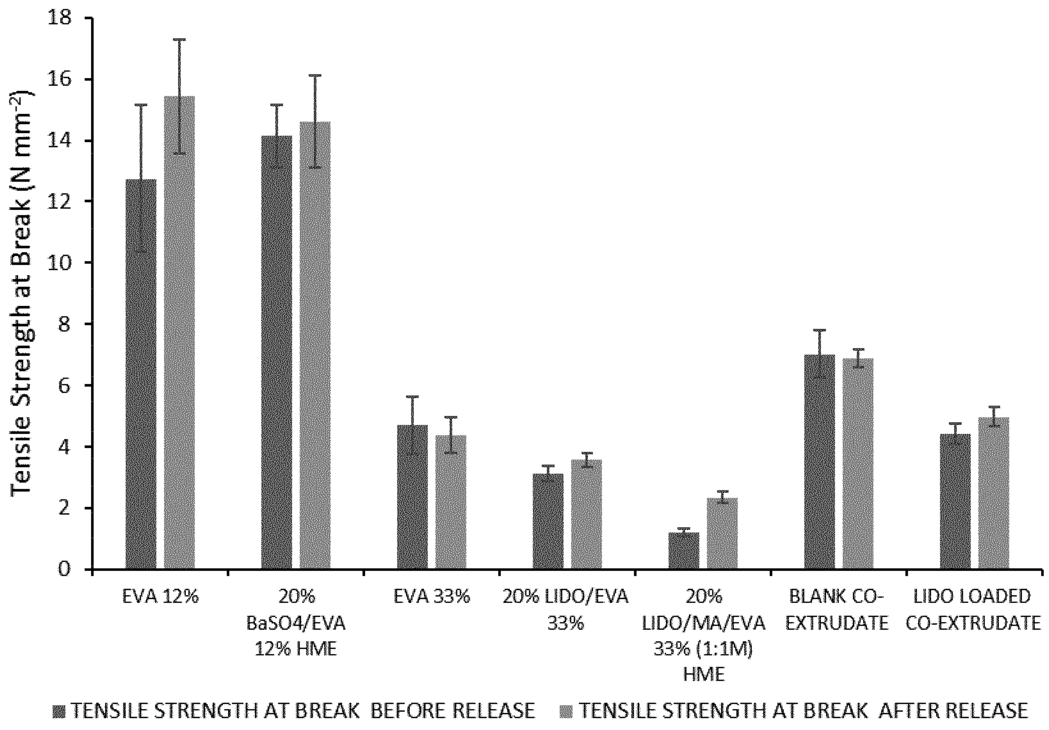
FIG. 21 shows tensile strength at break for the investigated hot melt extrudates (HME) before and after exposure to PBS for 10 days.

FIG. 21 and Table 17 displays the tensile strength (TS) of the extrudates and is a measure of the maximum stress a material can withstand before it breaks. EVA 12% HME and 20% BaSO4/EVA 12% HME yielded a significantly stronger TS before release: 12.733 and 14.147 N mm-2, respectively. Whereas, the weakest tensile strength at break was observed for the 20% LIDO/MA/EVA 33% (1:1M) HME formulation at 1.216 N mm-2. Comparing the TS for the individual extrudates before and after exposure to PBS revealed a significant increase in TS for the 20% LIDO/MA/EVA 33% (1:1M) HME, 20% LIDO/EVA 33% HME and the LIDO loaded co-extrudate, whereas the others exhibited no significant difference. Importantly, a significant enhancement in TS was observed when comparing the LIDO co-extrudate compared to 20% LIDO/MA/EVA 33% (1:1M) HME, both before and after exposure to PBS.

Table 18 summarises the tensile properties of the lidocaine loaded co-extrudate following the in vivo study. The YM recorded for Group 1 was significantly greater than the YM recorded for the LIDO loaded co-extrudate before and after PBS release (Table 5.9) and statistically similar to Group 3. Group 1 yielded the greatest tensile strength at break (8.288 N mm-2) and alongside Group 3 was signifi-

TABLE 17

Summary of the tensile properties for the investigated hot melt extrudates (HME) before and after exposure to PBS for 10 days.

| FORMULATION | YOUNG'S MODULUS MEAN ± SD (N $mm^{-2}$) BEFORE RELEASE | YOUNG'S MODULUS MEAN ± SD (N $mm^{-2}$) AFTER RELEASE | TENSILE STRENGTH AT BREAK MEAN ± SD (N $mm^{-2}$) BEFORE RELEASE | TENSILE STRENGTH AT BREAK MEAN ± SD (N $mm^{-2}$) AFTER RELEASE |
|---|---|---|---|---|
| EVA 12% HME | 32.142 ± 6.327 | 10.476 ± 2.872 | 12.733 ± 2.405 | 15.427 ± 1.848 |
| 20% $BaSO_4$/EVA 12% HME | 39.924 ± 6.95 | 6.933 ± 2.665 | 14.127 ± 1.015 | 14.612 ± 1.493 |
| EVA 33% HME | 2.406 ± 0.156 | 1.491 ± 0.395 | 4.708 ± 0.939 | 4.367 ± 0.578 |
| 20% LIDO/EVA 33% HME | 1.245 ± 0.399 | 0.784 ± 0.086 | 3.123 ± 0.250 | 3.561 ± 0.215 |
| 20% LIDO/MA/EVA 33% (1:1M) HME | 0.481 ± 0.063 | 0.774 ± 0.064 | 1.216 ± 0.124 | 2.349 ± 0.195 |
| BLANK CO-EXTRUDATE | 2.299 ± 0.322 | 2.288 ± 0.165 | 7.026 ± 0.770 | 6.901 ± 0.293 |
| LIDO LOADED CO-EXTRUDATE | 2.061 ± 0.195 | 2.826 ± 0.131 | 4.407 ± 0.340 | 4.975 ± 0.320 |

cantly greater than the tensile strength observed for the LIDO loaded co-extrudate before and after PBS release (Table 17).

TABLE 18

Summary of the tensile properties for the LIDO loaded co-extrudate before and after exposure to PBS for 10 days and following the in vivo study.

| | YOUNG'S MODULUS MEAN ± SD (N mm$^{-2}$) | | | | TENSILE STRENGTH AT BREAK MEAN ± SD (N mm$^{-2}$) | | | |
|---|---|---|---|---|---|---|---|---|
| FORMULATION | BEFORE RELEASE | AFTER RELEASE | IN VIVO (Group 1) | IN VIVO (Group 3) | BEFORE RELEASE | AFTER RELEASE | IN VIVO (Group 1) | IN VIVO (Group 3) |
| LIDO LOADED CO-EXTRUDATE | 2.061 ± 0.195 | 2.826 ± 0.152 | 5.458 ± 1.846 | 3.853 ± 0.355 | 4.407 ± 0.340 | 4.975 ± 0.320 | 8.288 ± 0.867 | 6.550 ± 0.338 |

Delamination of the bilayers in the LIDO loaded co-extrudate was observed following elongation on the texture analyser. However, this was not evident following exposure to PBS after 10 days or following the in vivo study. Neither was it evident for the blank co-extrudate, before or after release.

EVA Grade and Drug Loading

Figure 22:
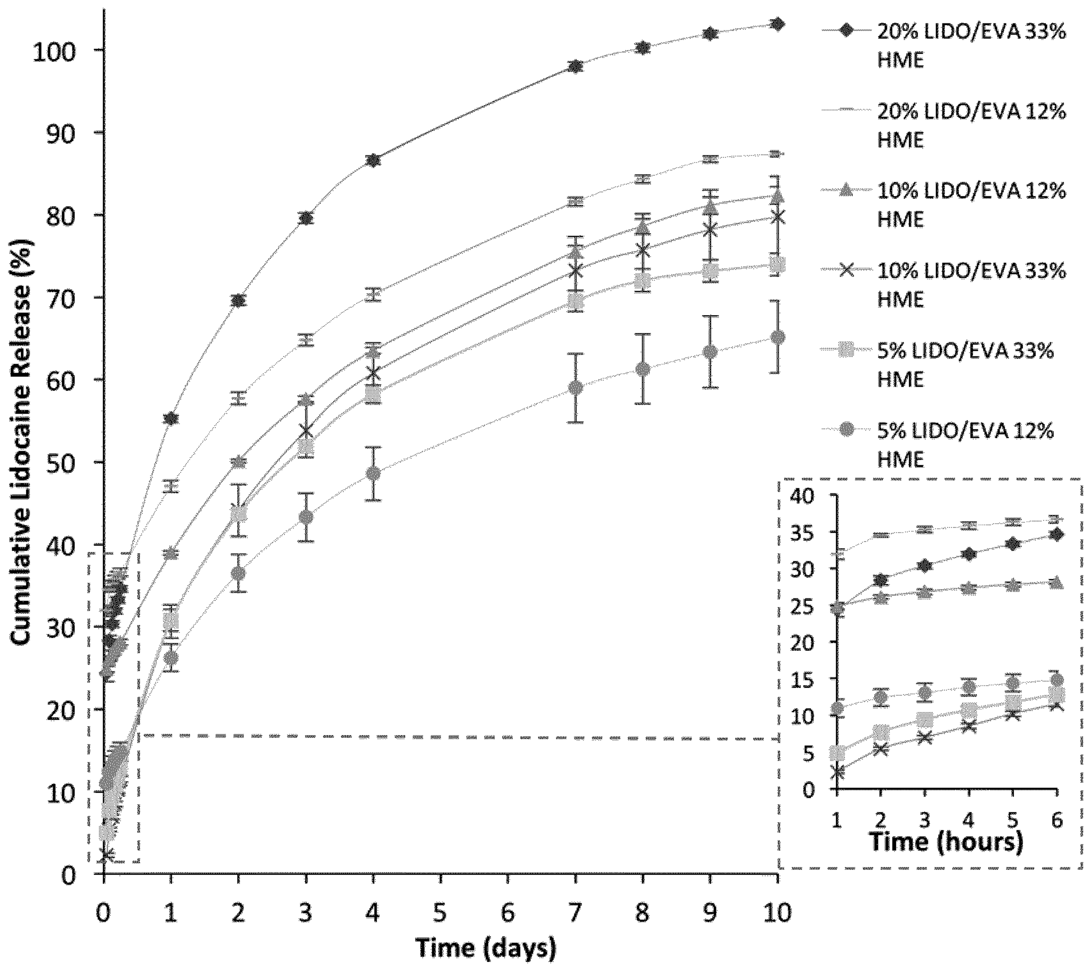
FIG. 22 is a graph depicting cumulative release of LIDO release from the 12% and EVA 33% carriers at different drug loadings, over a period of 10 days.

FIG. 22 exhibits the cumulative release of LIDO release from EVA 12% and EVA 33% carriers at different drug loadings, over a period of 10 days. An inset plot displays an enhanced view of the initial release of LIDO at 1-6 h. The cumulative release for days 1, 4 and 10 for each formulation is stated in Table 19.

There was a trend across all formulations (FIG. 22) where a burst release was observed in the first 24 hours, with subsequent release more controlled. The magnified inset in FIG. 22 shows the release at 1-6 h for 5% LIDO/EVA 12%, 5% LIDO/EVA 33% and 10% LIDO/EVA 33% was in the range of 0-15%. In contrast, during the same period the release for 10% LIDO/EVA 12%, 20% LIDO/EVA 33% and 20% LIDO/EVA 12%, was approximately 24-36%. It has been proposed that surface crystallisation may account for the differences in early drug release. Table 19 accentuates the burst release observed on day 1 for all extrudates. The greatest release for day 1 was evident from the 20% LIDO/EVA 33% formulation, which elicited a substantial burst of 55.25%. Sequential release was more sustained for all formulations. At day 10, the order of cumulative release was: 5% LIDO/EVA 12%<5% LIDO/EVA 33%<10% LIDO/EVA 33%<10% LIDO/EVA 12%<20% LIDO/EVA 12%<20% LIDO/EVA 33%.

TABLE 19

Summary of the cumulative drug release from the EVA 12% and EVA 33% carriers at different drug loadings, over a period of 10 days

| HME | Percentage (%) Cumulative Lidocaine Release Mean ± SD at Time (days) | | |
|---|---|---|---|
| Formulation | 1 | 4 | 10 |
| 5% LIDO/EVA 12% | 26.23 ± 1.67 | 48.56 ± 3.23 | 65.18 ± 4.40 |
| 10% LIDO/EVA 12% | 38.97 ± 0.26 | 63.51 ± 0.42 | 82.33 ± 1.04 |
| 20% LIDO/EVA 12% | 47.06 ± 0.72 | 70.32 ± 0.72 | 87.39 ± 0.32 |
| 5% LIDO/EVA 33% | 30.79 ± 1.34 | 58.21 ± 1.10 | 73.99 ± 1.35 |
| 10% LIDO/EVA 33% | 30.65 ± 2.04 | 60.79 ± 3.64 | 79.75 ± 4.93 |
| 20% LIDO/EVA 33% | 55.25 ± 0.42 | 86.63 ± 0.54 | 103.17 ± 0.42 |

With regards to the EVA grade, formulations consisting of EVA 33% compared to EVA 12% generally elicited statistically significantly greater LIDO release on days 1, 4 and 10. Comparisons were conducted on the corresponding drug loading for each EVA grade, i.e. 5% LIDO/EVA 12% vs 5% LIDO/EVA 33% etc. Exceptions to the trend were observed when comparing 5% LIDO/EVA 12% to 5% LIDO/EVA 33% on day 10 and 10% LIDO/EVA 12% to 10% LIDO/EVA 33% on day 4 and 10 (no significant difference). Furthermore, the 10% LIDO/EVA 12% exhibited greater release on day 1 compared to 10% LIDO/EVA 33%.

It was anticipated that increasing the drug load would elicit greater drug release (comparisons were performed within each EVA grade, i.e. 12% or 33%). Exceptions to this pattern were observed for the following; 5% LIDO/EVA 33% and 10% LIDO/EVA 33% at days 1, 4 and 10. Furthermore, on day 10 no significant difference was detected when comparing 10% LIDO/EVA 12% and 20% LIDO/EVA 12%.

20% LIDO/LIPD/EVA 33%

Figure 23:
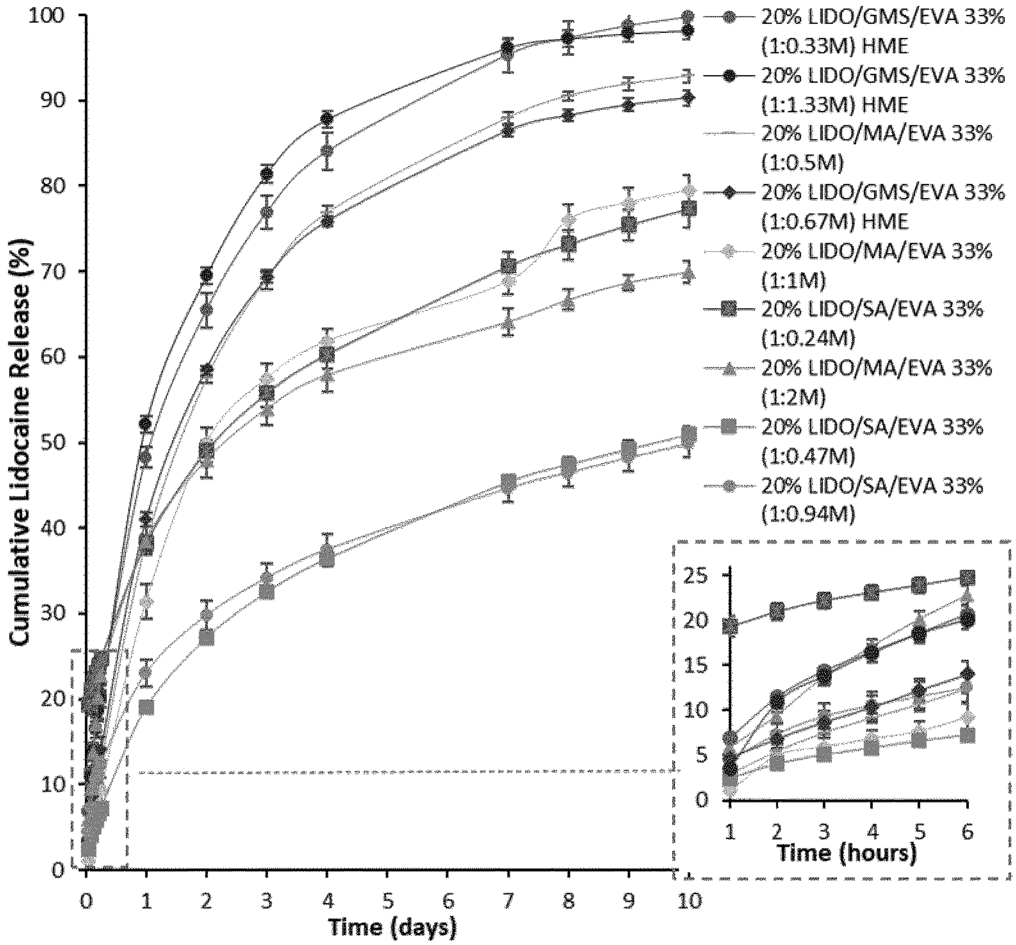
FIG. 23 is a graph depicting cumulative release of LIDO release from 20% LIDO/LIPID/EVA 33% hot melt extrudates (HME) over a period of 10 days.

FIG. 23 demonstrates a burst effect was observed for all formulations during the first 24 h of release. The 20% LIDO/SA/EVA 33% (1:0.24M) extrudate yielded substantial release within the first hour (as shown in the inset). Subsequent release, typically slowed after day 4. However, the release plot shows for the 20% LIDO/SA/EVA 33% 1:0.47M and 1:0.94M extrudates drug release was more gradual across all time points.

Except for the 20% LIDO/GMS/EVA 33% 1:0.33M and 1:1.33M formulations, the incorporation of lipids at the 20% drug loading generally resulted in a decrease in drug release compared to the 20% LIDO/EVA 33% extrudate void of lipid. Table 20 shows, for the MA extrudates, the 20% LIDO/MA/EVA 33% (1:1M) exhibited the statistically lowest release on day 1. The highest release on day 4 and 10 was exhibited by the LIDO/MA 1:0.5M formulation. The 1:1M and 1:2M samples elicited statistically similar release of LIDO on day 4. However, by day 10, the latter extrudate provoked the lowest drug release of the three MA ratios. For the GMS extrudates, it was determined that the 20% LIDO/GMS/EVA 33% (1:0.67M) extrudate induced the statistically lowest drug release across the three days evaluated. Whilst, the 1:0.33M and 1:1.33M extrudates exhibited similar release profiles over days 1, 4 and 10. The 20% LIDO/SA/EVA 33% (1:0.24M) sample provided the highest drug release over the three days evaluated when comparing the SA extrudates. The 1:0.47M and 1:0.94M formulations were similar across days 1, 4 and 10.

Overall, the 20% LIDO/SA/EVA 33% (1:0.47M) and 20% LIDO/SA/EVA 33% (1:0.94M) extrudates had the lowest drug release of all the 20% LIDO/LIPID/EVA 33% formulations. Whilst, the highest drug release was observed from the 20% LIDO/GMS/EVA 33% (1:0.33M) and 20% LIDO/GMS/EVA 33% (1:1.33M) extrudates.

TABLE 20

Summary of the cumulative drug release for the 20% LIDO/LIPID/EVA 33% hot melt extrudates (HME) over a period of 10 days.

| HME | Percentage (%) Cumulative Lidocaine Release Mean ± SD at Time (days) | | |
|---|---|---|---|
| Formulation | 1 | 4 | 10 |
| 20% LIDO/EVA 33% | 55.25 ± 0.42 | 86.63 ± 0.54 | 103.17 ± 0.42 |
| 20% LIDO/MA/EVA 33% (1:1M) | 31.39 ± 2.05 | 61.85 ± 1.49 | 79.49 ± 1.83 |
| 20% LIDO/MA/EVA 33% (1:0.5M) | 38.52 ± 1.68 | 76.84 ± 0.89 | 92.83 ± 0.75 |
| 20% LIDO/MA/EVA 33% (1:2M) | 38.52 ± 1.68 | 57.93 ± 1.95 | 69.97 ± 1.29 |
| 20% LIDO/SA/EVA 33% (1:0.47M) | 19.02 ± 0.37 | 36.43 ± 0.85 | 50.92 ± 1.00 |
| 20% LIDO/SA/EVA 33% (1:0.24M) | 38.19 ± 1.00 | 60.29 ± 1.71 | 77.33 ± 2.23 |
| 20% LIDO/SA/EVA 33% (1:0.94M) | 23.05 ± 1.54 | 37.45 ± 1.77 | 49.78 ± 1.53 |
| 20% LIDO/GMS/EVA 33% (1:0.67M) | 41.01 ± 0.81 | 75.86 ± 0.54 | 90.31 ± 0.88 |
| 20% LIDO/GMS/EVA 33% (1:0.33M) | 48.24 ± 1.19 | 84.02 ± 2.22 | 99.74 ± 1.85 |
| 20% LIDO/GMS/EVA 33% (1:1.33M) | 52.13 ± 1.73 | 87.80 ± 4.47 | 98.17 ± 3.27 |

Co-Extrudate

Figure 24:
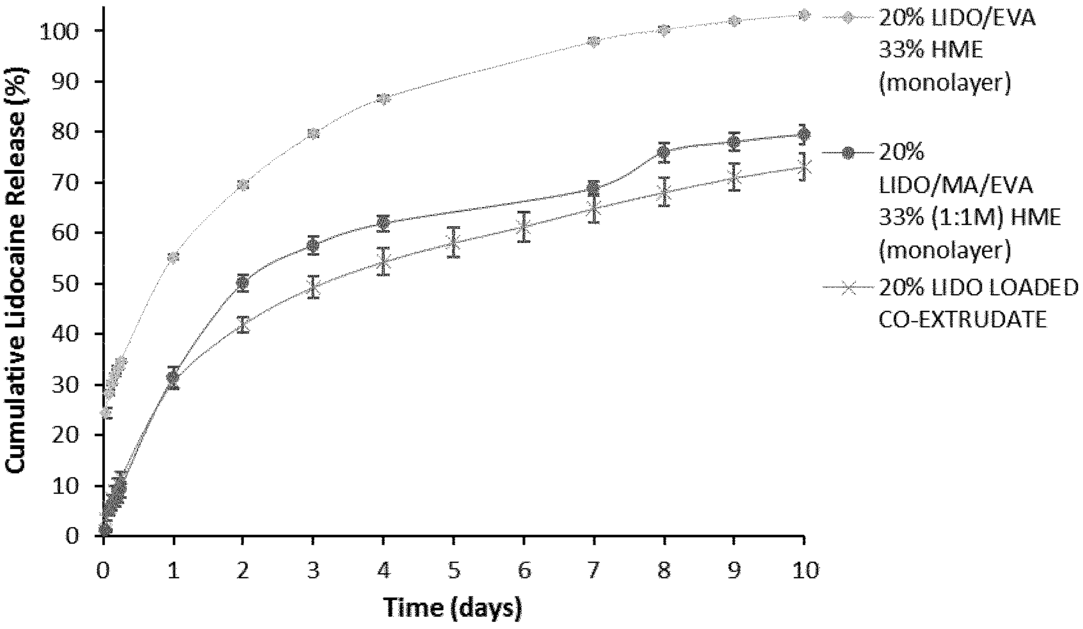
FIG. 24 is three graphs depicting A) cumulative release of LIDO release from 20% LIDO/EVA (33% VA), 20% LIDO/MA/EVA (33% VA) (1:1M) monolayer hot melt extrudates (HME) and the 20% LIDO loaded co-extrudate over a period of 10 days, B) release of lidocaine from melt extrudate containing 20% lidocaine, 20% myristic acid and 60% EVA (33% VA), under sink conditions, and C) release of lidocaine from melt extrudate containing 20% lidocaine, 20% myristic acid and 60% EVA (33% VA), under non-sink conditions, as described herein in Example 4.
Figure 25:
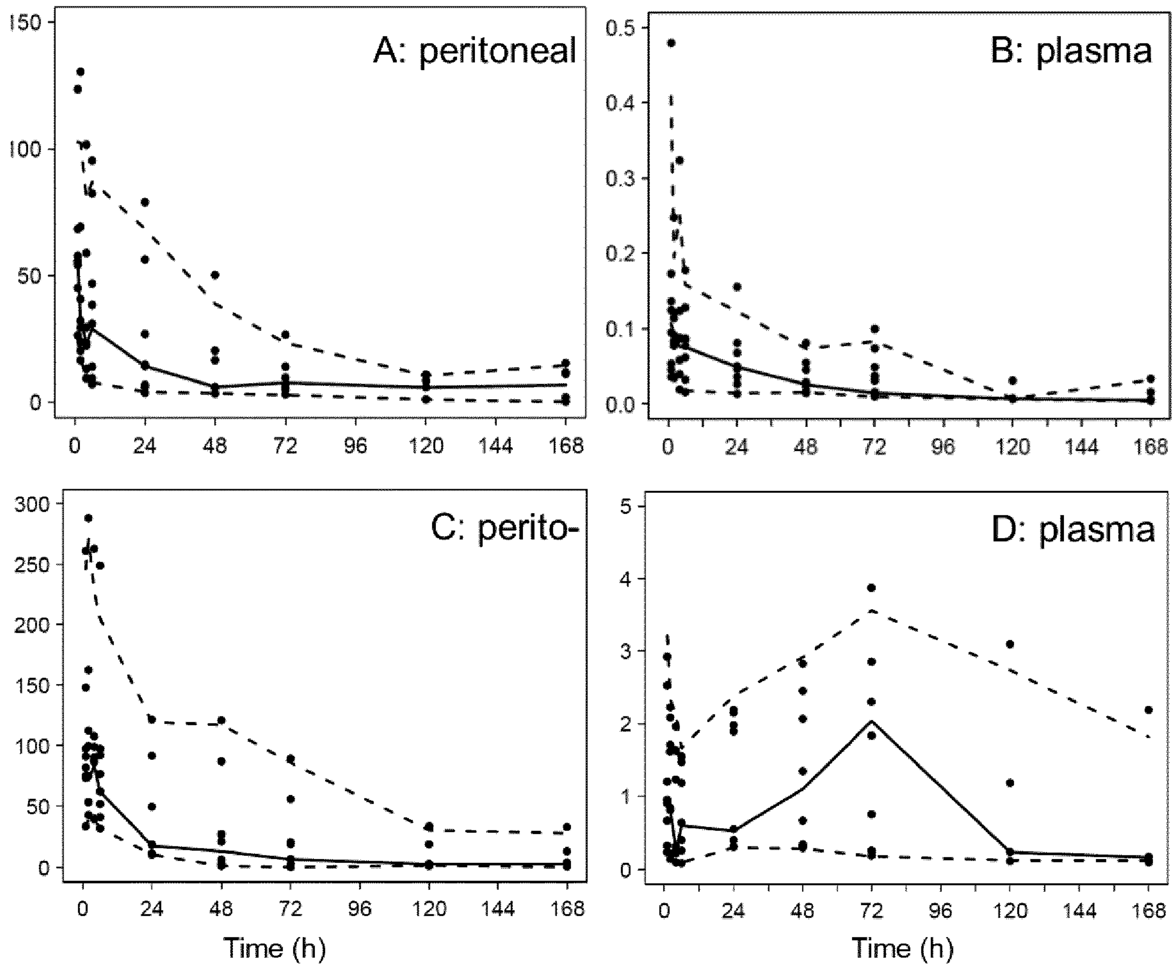
FIG. 25 is four graphs showing concentrations of lidocaine were several folds higher in peritoneal fluid (A) compared to plasma (B). Myristic acid concentrations were higher than those seen for lidocaine, with higher concentrations again observed in peritoneal fluid (C) compared to plasma (D). Data points represent individual values, the solid line represents mean values with the dashed lines representing 10 and 90th percentiles.

The 20% LIDO loaded co-extrudate was composed of an outer layer of 20% LIDO/MA/EVA 33% (1:1M) and an inner core of 20% $BaSO_4$/EVA 12%. Drug release was performed and comparisons were made with the 20% LIDO/MA/EVA 33% (1:1 M) monolayer to deduce the impact of co-extrusion processing. A t-test revealed there was no significant difference between the co-extruded and the monolayer formulation at day 1 (data not shown), while on days 4 and 10 there was significant difference, with the co-extrudate eliciting slightly lower release of lidocaine. The 20% LIDO loaded co-extrudate exhibited statistically significant lower drug release on days 1, 4 and 10 when compared to the 20% LIDO/EVA 33% monolayer device devoid of lipid (See FIG. 24).

Release from eutectic in the co-extruduate was similar to release from a single EVA strand containing the eutectic. The formation of the co-extrudate maintained the advantages of the eutectic observed in single strands, the ability to stabilize drug and achieve sustained release. The co-extrudate had the added advantage of tensile strength and radio-opacity.

Release of Lidocaine from EVA Melt Extrudate

The release profiles of lidocaine from the melt extrudate are shown in FIGS. 24B and 24C. The release of lidocaine under sink conditions (FIG. 24B) occurred at a faster rate into PF than PBS. During the first 3 h the release profiles were similar, with about 11 and 12% of lidocaine being released into PF and PBS, respectively. However, the release rate of lidocaine into PF continued to increase rapidly after 3 h. The release of lidocaine from the EVA melt extrudate under non-sink condition is displayed in FIG. 24C. The release profile generated under non-sink condition showed a similar trend, with higher release rates of lidocaine observed in PF compared to PBS. This experiment demonstrates that implants according to the invention have the potential to achieve very high drug elution in to biological fluids under both sink and non-sink conditions.

In Vivo Sheep Study

Ovine Surgery and Implantation

All of the sheep made it to the end point of the experiment and no early euthanasia was required. For the lignocaine implants that were in situ for 7 days fibrin tracts had started to form and active inflammation was seen on the omentum (data not shown). The tracts were more significant for the 7 day lignocaine implants than in the blank implants and the silicone drains. Of note, the fibrinous tracts were softer at 3 days and were the same compared to the silicone drain (data not shown).

Pharmacokinetics of Lidocaine and Myristic Acid

Lidocaine and myristic acid were measured in peritoneal fluid and blood at the first time point, 1 hour, indicating release and absorption processes begin quickly following administration. The general trend for lidocaine levels in both peritoneal fluid and blood was slowly decreasing levels over 7 days.

Peritoneal levels, and blood levels, of lidocaine and myristic were determined by HPLC-MS and are reported in FIGS. 25A to D, respectively.

Considerable inter-animal variation was noted, which is not unexpected. Concentrations achieved in the local peritoneal environment were several orders of magnitude higher than in the blood. The circulating blood levels were well below the reported toxic levels in humans.

These data show the implants functioned as sustained release vehicles following implantation in the body.

A two compartment model best described lidocaine concentrations overtime in the peritoneal and central compartments. A dual absorption profile for dosing to the peritoneal compartment was selected on the basis of goodness of fit plots over single absorption processes. Models for enterohepatic recirculation and adherence of lidocaine to the insert (using an additional compartment within the peritoneal compartment) were explored by not supported by the data. The final model consisted of a bolus input with a first order infusion absorption profile, with 51% of the dose contributing to the first order release profile. Bioavailability could not be estimated in this dataset as i.v. data were not available. CL from the central compartment, at 6.84 L/h/kg was similar to reported values (2.82 L/h/kg in non-pregnant ewes for lidocaine following bolus dose described using a 2 compartment model describing central and peripheral tissues). The volume of distribution parameter was estimated at just 0.04 L/kg, much less than previous reports (0.95-1.5 L/kg).

Table 21 below shows the pharmacokinetic parameter estimates for lidocaine. Bio describes the proportion of the total dose estimated to contribute to the bolus release components; Tabs describes the half time for absorption for first order release component; CL and V are clearance and volume parameters relating to the central compartment; Q is intercompartmental CL between central and peritoneal compartments; Vp is volume of the peritoneal compartment; ERRADD is residual unknown variability; PPV is the coefficient of variation of between subject; Cl is the confidence interval estimated using bootstrap methods and 500 simulations. 'Fix' denotes parameters that are fixed and not estimated.

TABLE 21

Pharmacokinetic parameters for lidocaine in the in vivo model

| Parameter | Estimate | PPV | 95% CI |
|---|---|---|---|
| Bio | 0.51 | 0 Fix | — |
| Tabs (h) | 0.065 | 0 Fix | — |
| CL/F ($L \cdot h^{-1} \cdot 70\ kg^{-1}$) | 479 | 0.51 | |
| V/F ($L \cdot 70\ kg^{-1}$) | 2.47 | 0.26 | |
| Q/F ($L \cdot h^{-1} \cdot 70\ kg^{-1}$) | 1.16 | 0.50 | |
| Vp/F ($L \cdot 70\ kg^{-1}$) | 30.7 | 0.35 | |

TABLE 21-continued

Pharmacokinetic parameters for lidocaine in the in vivo model

| Parameter | Estimate | PPV | 95% CI |
|---|---|---|---|
| Peritoneal $ERR_{ADD}$ ($mg \cdot L^{-1}$) | 1.87 | — | |
| Peritoneal $ERR_{PROP}$ (%) | 55.4 | — | |
| Plasma $ERR_{ADD}$ ($mg \cdot L^{-1}$) | 0.02 | — | |
| Plasma $ERR_{PROP}$ (%) | 27.7 | — | |

Figure 26:
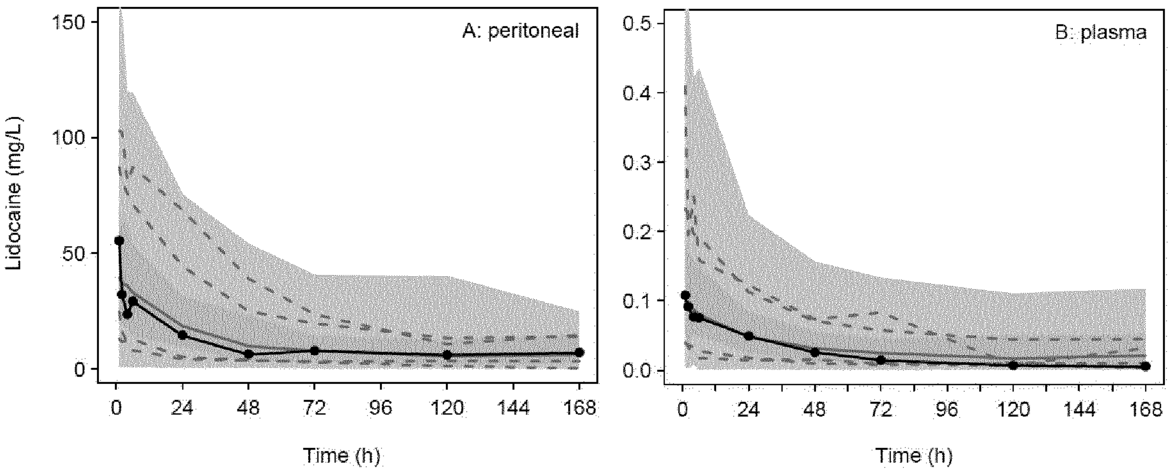
FIG. 26 presents visual predictive check plots for the lidocaine pharmacokinetic model. Observation percentiles from the observed data are given in black (median, solid line; 10th and 90th percentile, dashed line). These are overlaid with model predictions (median, 10th and 90th prediction percentiles given in red; solid and dashed lines respectively). Shaded areas are 95% confidence intervals for the prediction percentiles.

FIG. 26 presents visual predictive check plots for the lidocaine pharmacokinetic model. Observation percentiles from the observed data (black: median, solid line; 10th and 90th percentile, dashed line) were overlaid with model predictions (median, 10th and 90th prediction percentiles given in red; solid and dashed lines respectively), and closely agreed with observation percentiles captured within the prediction confidence intervals, suggesting good model fit. Shaded areas are 95% confidence intervals for the prediction percentiles.

Lidocaine and Myristic Acid Remaining Post-Implantation

The amount of lidocaine remaining 3 and 7 days post-implantation is shown in Table 22. More than 80% of the lidocaine and myristic acid was released from the co-extrudates over the first 3 days. This correlates with the observed concentrations in blood and peritoneal fluid. After 7 days less than 5% of lidocaine remained in the co-extrudates while the myristic acid levels were too low to quantify by the LCMS method.

TABLE 22

Lidocaine and MA remaining in extrudates after implantation for 3 or 7 days.

| Sheep Number | Duration of implantation | Lidocaine % Remaining | Myristic acid % Remaining |
|---|---|---|---|
| Sheep 38 | 3 days | 10.47 ± 0.49 | 10.04 ± 1.82 |
| Sheep 73 | 3 Days | 18.31 ± 3.16 | 16.91 ± 6.77 |
| Sheep 42 | 3 Days | 18.58 ± 0.83 | 11.21 ± 0.98 |
| Sheep 44 | 7 Days | 4.22 ± 0.51 | <4.00* |
| Sheep 10 | 7 Days | 2.57 ± 0.56 | <4.00* |
| Sheep 30 | 7 Days | 1.36 ± 0.10 | <4.00* |
| Sheep 40 | 7Days | 0.80 ± 0.33 | <4.00* |
| Sheep 54 | 7 Days | 0.90 ± 0.10 | <4.00* |
| Sheep 57 (Blank) | 7 Days | — | — |

*Concentration in samples was below the Limit of Quantification Values are expressed as a % remaining compared to the lidocaine loading levels before implantation (mean ± SD; n = 3)

Histopathology

Figure 27:
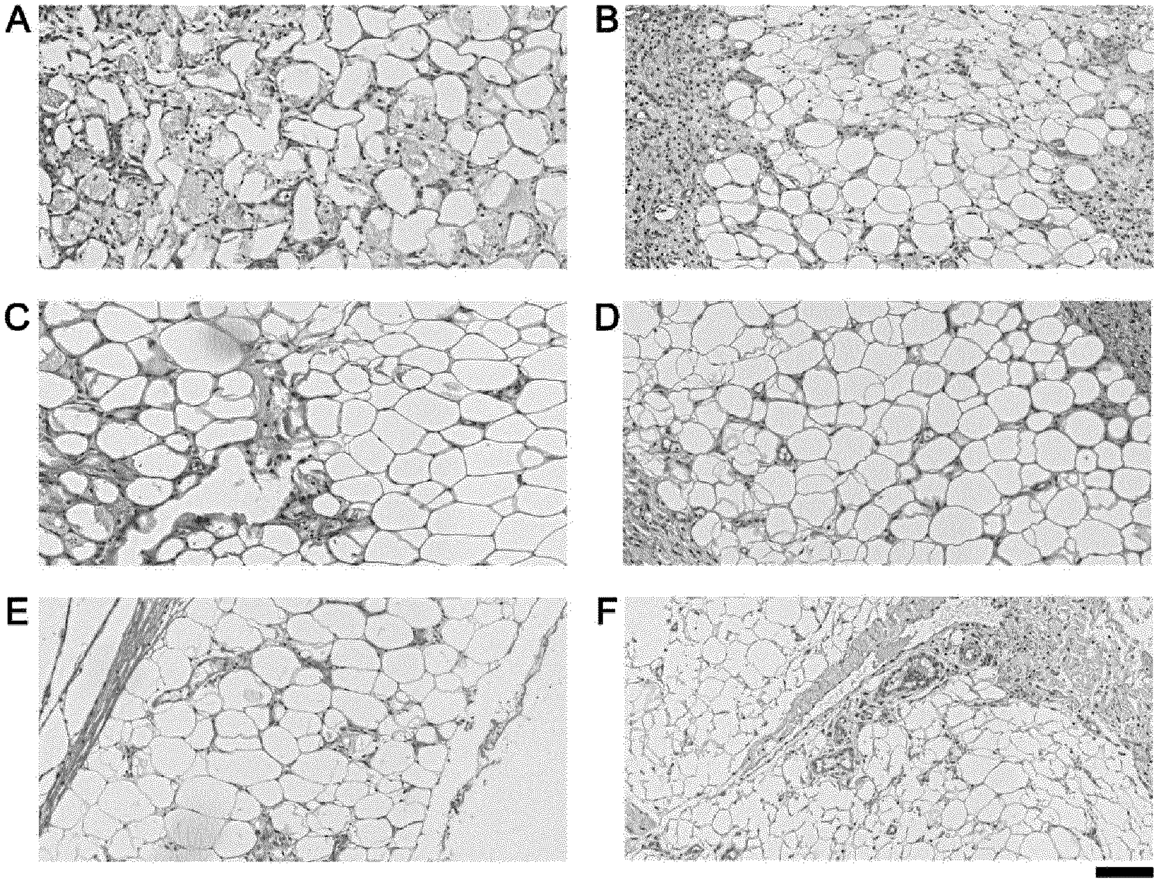
FIG. 27 presents representative images showing histopathological changes post-implantation in sheep. In sheep implanted with blank extrudates for 7 days (Sheep 55), chronic inflammation infiltrating the fat was observed along with extensive granulation and fat necrosis at the A. implant and B. drain sites. Similarly, on implantation of the lidocaine-loaded implant for 7 days (Sheep 44), also showed significant chronic inflammation associated with granulation tissue and fat necrosis at the C. implant and D. drain sites. On implantation of the lidocaine-loaded implant for 3 days (Sheep 73), extensive acute inflammation and necrosis was observed at the E. implant and F. drain sites without any granulation tissue; scale bar=100 μm.

Histopathological analysis showed chronic active inflammation with granulation at both implant and drain sites in sheep on implantation of lidocaine-loaded or blank implants for 7 days (FIG. 27 and Table 23). Inflammation at the drain and implant site was comparable in all animals. Subsequently, the duration of implantation was reduced to 3 days, resulting in absence of granulation and fibrosis. Acute inflammation was still evident at both implant and drain site. EVA is generally regarded as biocompatible and used in a number of medical devices and drug delivery systems. While all implanted materials will result in a foreign body response it is the speed and extent of this response that determines ultimately usability.

TABLE 23

Summary of inflammation, granulation and fibrosis observed in response to the EVA co-extrudates after 3 or 7 days of implantation.

| | | Inflammation | | Granulation and Fibrosis | |
|---|---|---|---|---|---|
| Sheep Number | Duration of implantation | Implant site | Drain site | Implant site | Drain site |
| Sheep 38 | 3 days | 3 | 3 | 0 | 0 |
| Sheep 73 | 3 Days | 2 | 3 | 0 | 0 |
| Sheep 42 | 3 Days | 3 | 3 | 0 | 0 |
| Sheep 44 | 7 Days | 3 | 3 | 2 | 4 |
| Sheep 10 | 7 Days | 3 | 1 | 2 | 2 |
| Sheep 30 | 7 Days | 3 | 3 | 2 | 1 |
| Sheep 40-1 | 7 Days | 3 | 3 | 4 | 4 |
| Sheep 40-2 | 7 Days | 1 | 1 | 1 | 1 |
| Sheep 55 (Blank) | 7 Days | 3 | 1 | 2 | 2 |
| Sheep 46 (Blank) | 7 Days | 1 | 1 | 3 | 2 |
| Sheep 57 (Blank) | 7 Days | 3 | 3 | 4 | 2 |

Tensile Strength of the Implant

Figure 28:
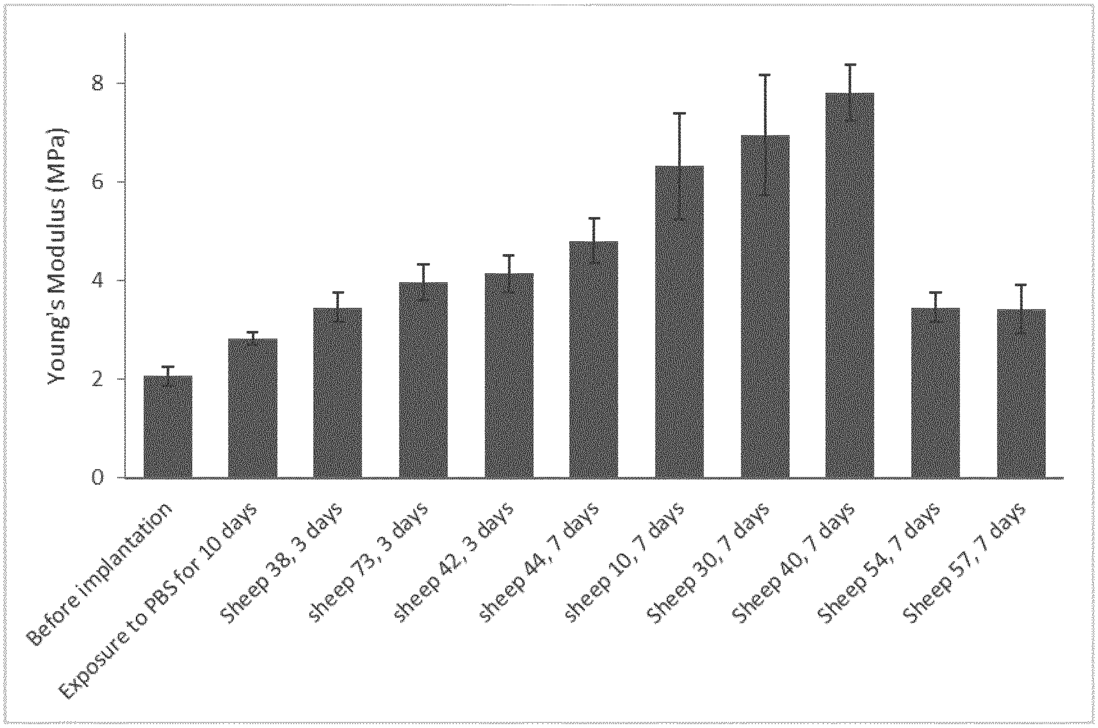
FIG. 28 shows Young's modulus of implant before in-vivo implantation and following 3 or 7 days in situ in a sheep model, or exposure to phosphate buffered saline for 10 days. Mean values reported with error bars representing standard deviation, n=5.
Figure 29:
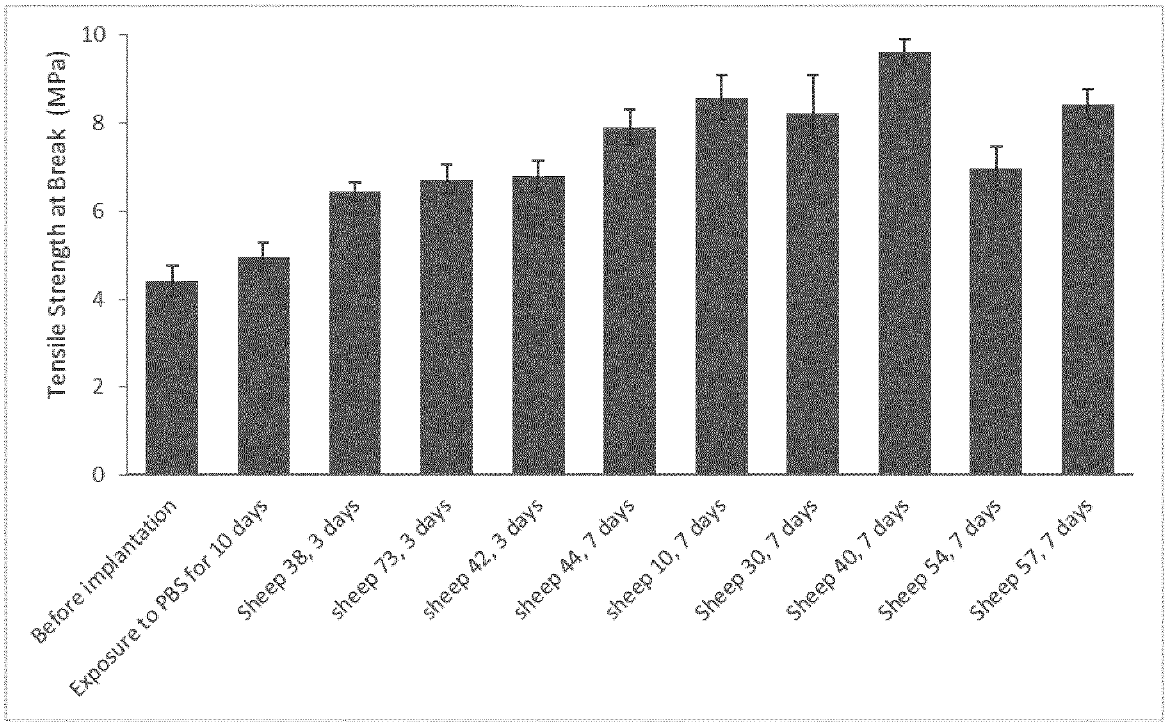
FIG. 29 shows tensile strength at break of implant before in-vivo implantation and following 3 or 7 days in situ in a sheep model, or exposure to phosphate buffered saline for 10 days. Mean values reported with error bars representing standard deviation, n=5.

For the implants, both Young's modulus and tensile strength at break increased following in-vivo implantation (FIGS. 28 and 29). These parameters are important, and the results observed indicate that the implant is sufficiently strong and resilient to be readily removed when required.

Surface Morphology

Figure 30:
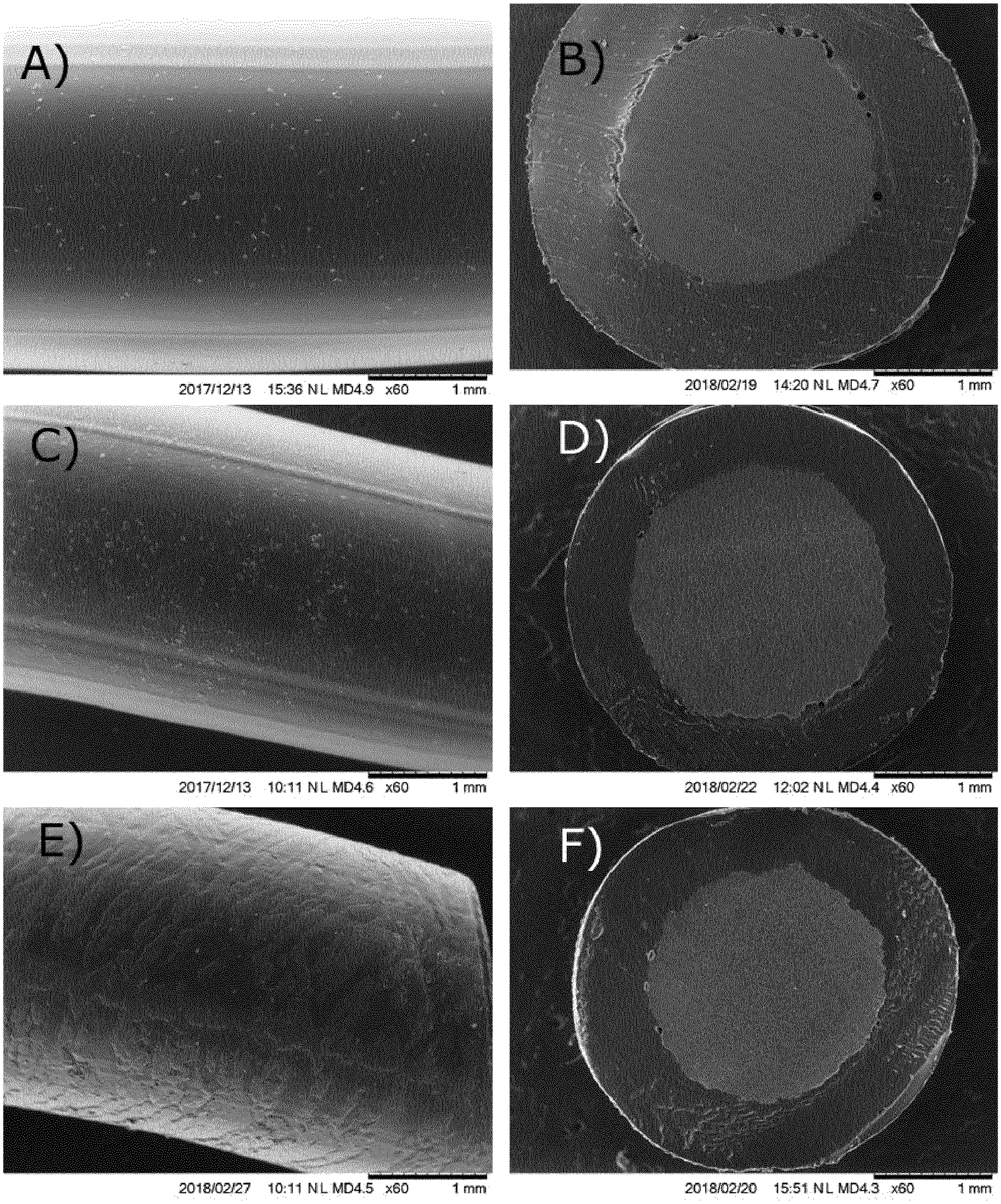
FIG. 30 shows SEM images of Implant following manufacture A) surface and B) cross-section, following 3 days implantation C) surface and D) cross-section, and following 7 days implantation E) surface and F) cross-section. Scale bar=1 mm.

Scanning electron micrographs of the implants before and after implantation are shown in FIG. 30. In the cross sectional images the core loaded with barium sulfate is clearly distinguishable from the drug loaded shell. Some pores are evident between the core and shell layers which can be attributed to the manufacture process. The surface of the implants, while smooth before implantation, had some surface roughness after 3 days implantation which is much more evident after 7 days implantation. This roughness may be biological debris and correlates with granulation and fibrosis that became evident after 7 days implantation.

Discussion

In summary, co-extrusion of a bilayer device yielded a viable drug delivery implant. The 20% LIDO/MA/EVA 33% extrudate was shown to profoundly overcome the recrystallisation issues observed with non-eutectic formulations. Moreover, the tensile properties were improved, a desirable drug release profile was found, and the plasma levels in the sheep model were within the acceptable limits with biocompatibility established for 3 day administration.

These examples clearly demonstrate that active agents can be formulated in eutectic compositions at high concentrations and prepared as biocompatible implants using the methods described herein, and that such implants can be used to provide therapeutically effective amounts of active agent. These examples clearly demonstrate the research, diagnostic, and therapeutic value of the implants described herein.

Example 5: Assessment of Lidocaine Eutectics and Drug Loading in EVA Polymers This study assessed the preparation of eutectic compositions comprising lidocaine, and of lidocaine- and lidocaine eutectic-loaded EVA films.

Figure 31:
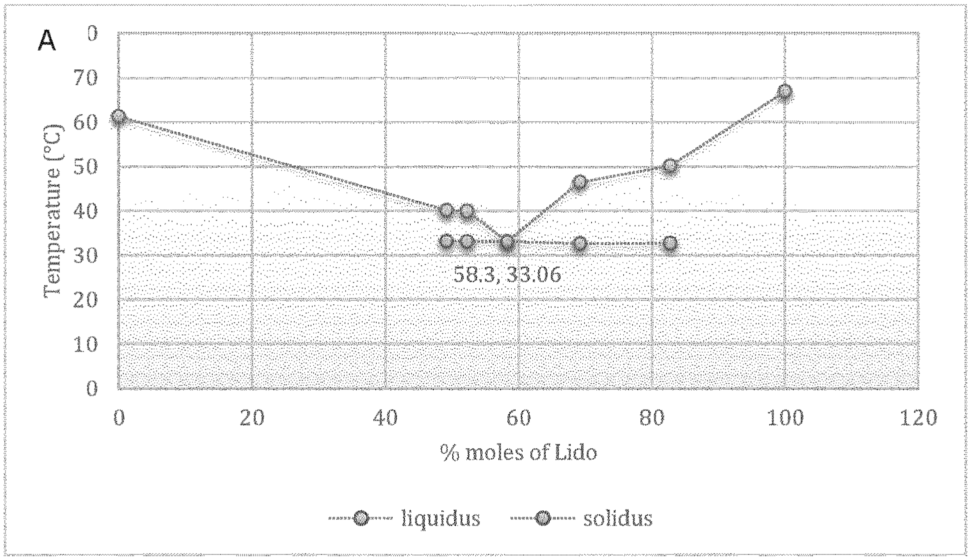
FIG. 31 is a graphical representation of thermal behaviour of lidocaine and palmitic acid binary mixtures observed during the second heating cycle, as described in Example 5 herein.

Lidocaine and palmitic acid was shown to form a eutectic. At the eutectic point (58.3% molar percentage of Lido), a single sharp melting endotherm was observed at 33° C., as shown in FIG. 31.

2DCOS FTIR studies showed that palmitic acid's C═O also interacts with lidocaine's N—H group and stabilises it in EVA matrices, thus reducing crystallization. Eutectic formation and stabilisation of Lidocaine in EVA matrices was also observed using a combination of fatty acids; for example palmitic and oleic acid (OA).

Figure 32:
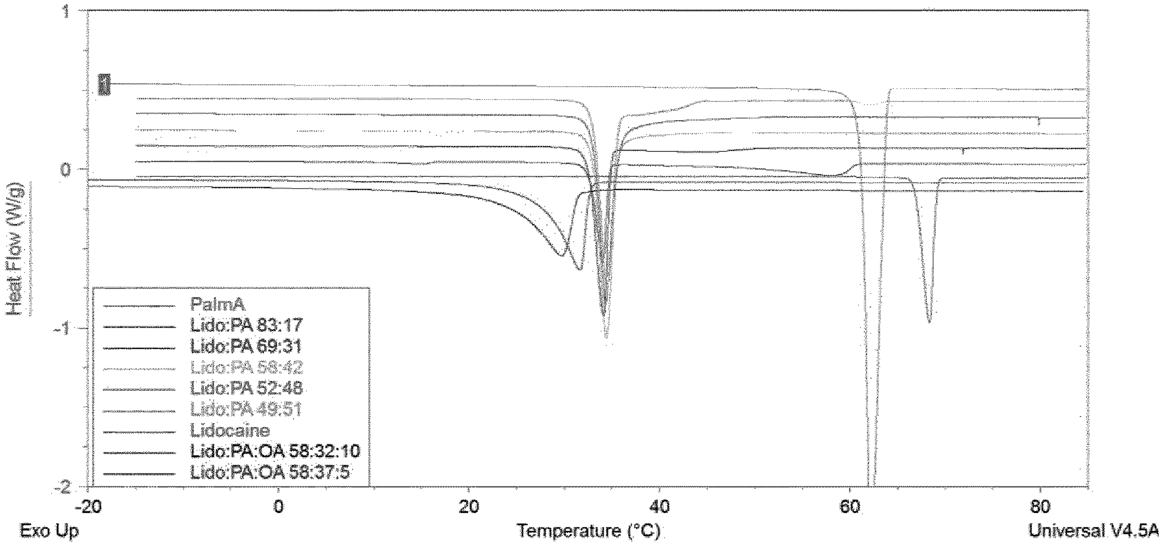
FIG. 32 presents DSC thermograms showing thermal behaviour of lidocaine and fatty acid mixtures, as described in Example 5 herein.

EVA films containing lidocaine, either alone or as a eutectic with palmitic or palmitic and oleic acid were prepared by solvent casting method using dichloromethane as the solvent. The various compositions are shown in Table 24 below, while their thermal behaviour as assessed by DSC is shown in the thermograms of FIG. 32.

TABLE 24

EVA film compositions.

| | Composition (% w/w) | | | |
|---|---|---|---|---|
| Ingredient | Film 1 | Film 2 | Film 3 | Film 4 |
| EVA | 100% | 80% | 60% | 60% |
| Lidocaine | — | 20% | 22% | 22% |
| Palmitic Acid | — | — | 18% | 13% |
| Oleic Acid | — | — | — | 5% |
| Observation at 1 week | Clear | Crystals | Opaque but no crystals | Clear |

Figure 33:
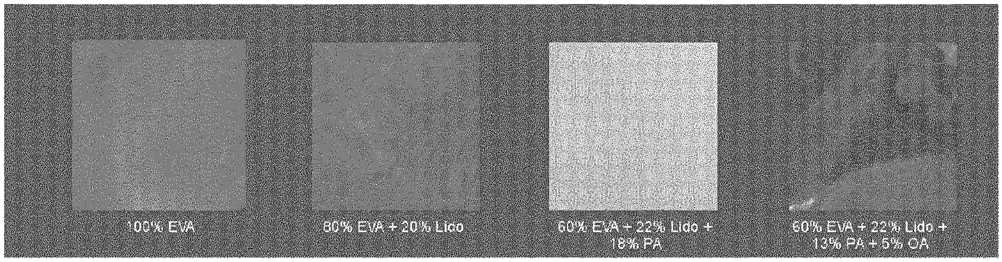
FIG. 33 presents a visual observation of Lidocaine films in EVA after 1 week. From left to right: Film 1, Film 2, Film 3 and Film 4, as described in Example 5 herein.

Visual characterization of the various films formed was carried out, as shown in FIG. 33. Film 4, comprising a eutectic composition of Lidocaine, palmitic acid, and oleic acid, showed marked transparency.

Example 6: Assessment of Bupivacaine-Containing Eutectics

This study assessed the preparation of eutectic compositions comprising bupivacaine and various fatty acids and combinations thereof.

Bupivacaine (BVC) only formed eutectics with fatty acid when present as a base and no such interaction was observed using bupivacaine hydrochloride, possibly because electrostatic interaction between the ammonium and chloride ions in the hydrochloride salt being stronger make the N—H group unavailable for hydrogen bonding with C═O of fatty acids.

Figure 34:
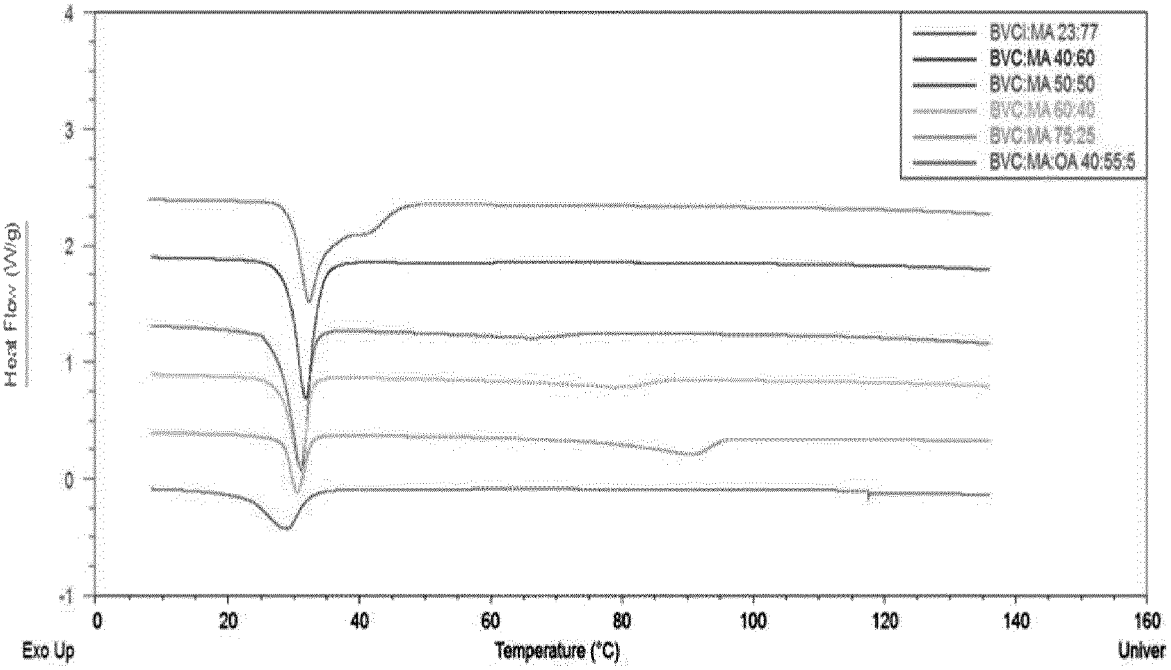
FIG. 34 presents DSC thermograms of BVC+MA physical mixtures, as described in Example 6 herein.

Distinct solidus and liquidus peaks could be observed at all molar ratios in the BVC base and MA mixtures, except at the eutectic point. The solidus and liquidus peaks became less distinct as the molar composition approached the eutectic composition (BVC:MA 40:60 moles) at which point, a single sharp peak was observed (eutectic temperature=29° C.). See FIG. 34.

The bupivacaine melted at 101.99° C. and thermal behaviour of the BVC:myristic acid mixtures differed considerably during the first and second heating cycles. For the eutectic mixture, a single sharp melting endotherm was observed during the first heating cycle (29° C.) in premixed BVC and myristic acid mixtures. No crystallization was observed during the cooling cycle. During the second heating cycle, cold crystallization followed by endothermic events was observed between 15-30° C.

Incorporation of 5% oleic acid (OA) or lauric acid (LA) in fatty acid component depressed the melting point to 22.4° C. and 22.9° C., respectively. See FIG. 34.

These results establish that bupivacaine is able to be formulated as a eutectic composition with fatty acids, and that by altering the fatty acid present in the composition, or the combination of fatty acids present, the melting point of the eutectic could be manipulated as desired.

Example 7: Preparation and Assessment of Bupivacaine Eutectics in EVA Polymers This study assessed the preparation of EVA films comprising eutectic compositions comprising bupivacaine (BVC) and fatty acids.

EVA films containing either BVC alone or in combination with fatty acids were prepared by solvent casting using dichloromethane as the solvent. The film composition and physical stability are summarized below in Table 25.

TABLE 25

EVA film compositions.

| | Composition (% w/w) | | | | |
|---|---|---|---|---|---|
| Ingredient | Film B1 | Film B2 | Film B3 | Film B4 | Film B5 |
| EVA | 100% | 92.5% | 83.6% | 83.6% | 83.4% |
| Bupivacaine | — | 7.5% | 7.5% | 7.5% | 7.5% |
| Myristic Acid | — | — | 8.9% | 8.3% | 8.3% |
| Oleic Acid | — | — | — | 0.9% | — |
| Lauric Acid | — | — | — | — | 0.7% |
| Observation at 2 weeks | Clear | Crystals | Clear | Clear (yellowish colour) | Clear* (yellowish colour) |
| Observation at 4 months | Clear | Crystals/ opaque film | Clear | Clear (yellowish colour) | Clear* (yellowish colour) |

*some crystals were observed at the edges, possibly due to non-uniformity of the dispersion Bupivacaine at 7.5% is EVA was unstable with crystallisation occurring. In contrast, Bupivacaine at this concentration (7.5%) when present as a eutectic was stable in EVA with no crystallisation observed.

These results establish that eutectic compositions of bupivacaine with one or more fatty acids can be incorporated into an EVA polymer composition, and is stable (with no crystallisation occurring) at concentrations at which the drug crystallizes out when present as a non-eutectic composition.

Example 8: Assessment of Ropivacaine-Containing Eutectics

This study assessed the preparation of eutectic compositions comprising ropivacaine and fatty acid.

Figure 35:
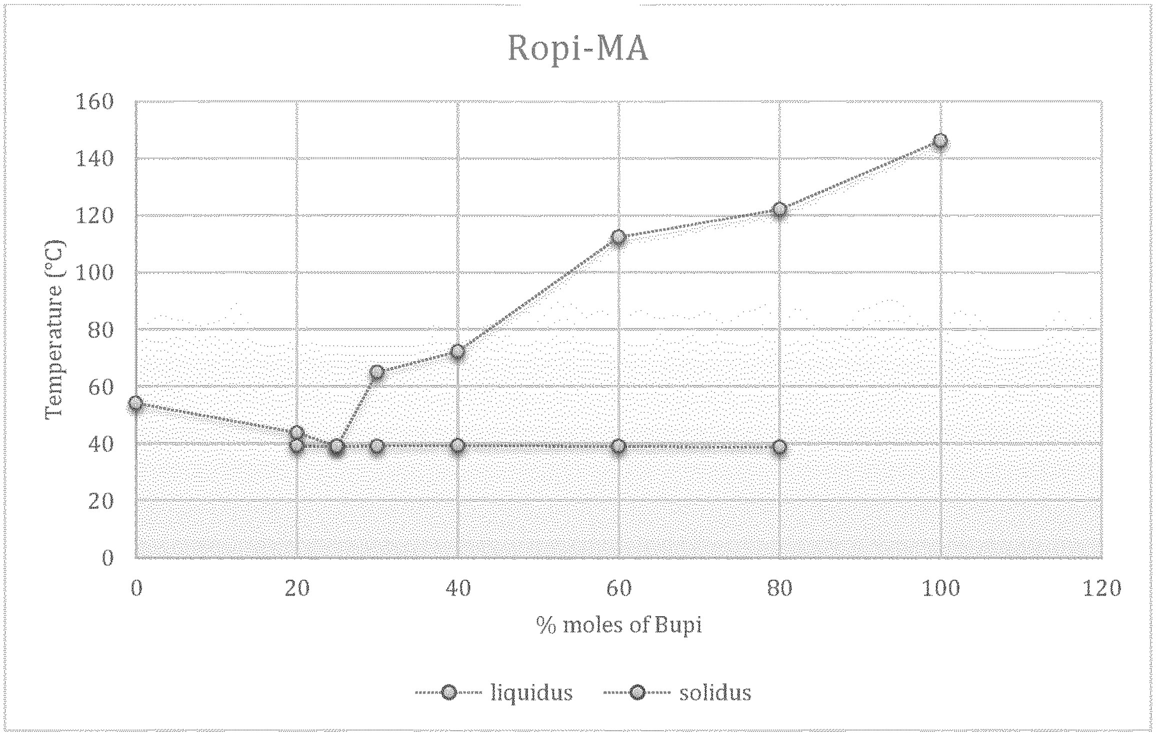
FIG. 35 presents a phase diagram of thermal behaviour of ropivacaine and myristic acid binary mixtures, as described in Example 8 herein.

A eutectic composition comprising ropivacaine and myristic acid in a 25:75 mol ratio was prepared. This composition had a eutectic point at 40° C. A eutectic composition comprising ropivacaine and palmitic acid was also prepared, the thermal behaviour of which is shown in the phase diagram depicted in FIG. 35.

Incorporation of the ropivacaine-containing compositions showed that the ropivacaine:myristic acid eutectic had better physical stability in EVA than ropivacaine alone (data not shown).

Example 9: Assessment of NSAID-Containing Eutectics

This study assessed the preparation of eutectic compositions comprising the NSAID ibuprofen (IBU) and fatty acids.

Figure 36:
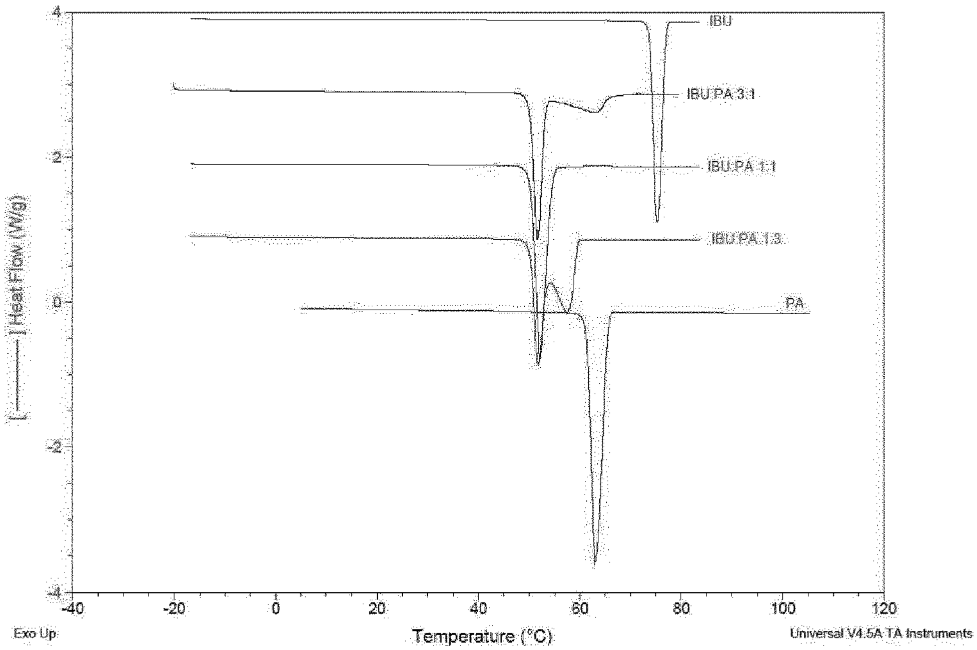
FIG. 36 shows the DSC thermograms displaying the second heating cycle of ibuprofen and palmitic acid binary mixtures.

Binary mixtures having a 1:1 molar ratio of IBU and palmitic acid showed a single sharp melting endotherm at 50.4° C., which is lower than that of IBU (73.73° C.) or palmitic acid (61.53° C.) alone. Distinct solidus and liquidus peaks were evident in binary mixtures containing excessive IBU or palmitic acid in the first heating cycle as shown in FIG. 36.

Figure 37:
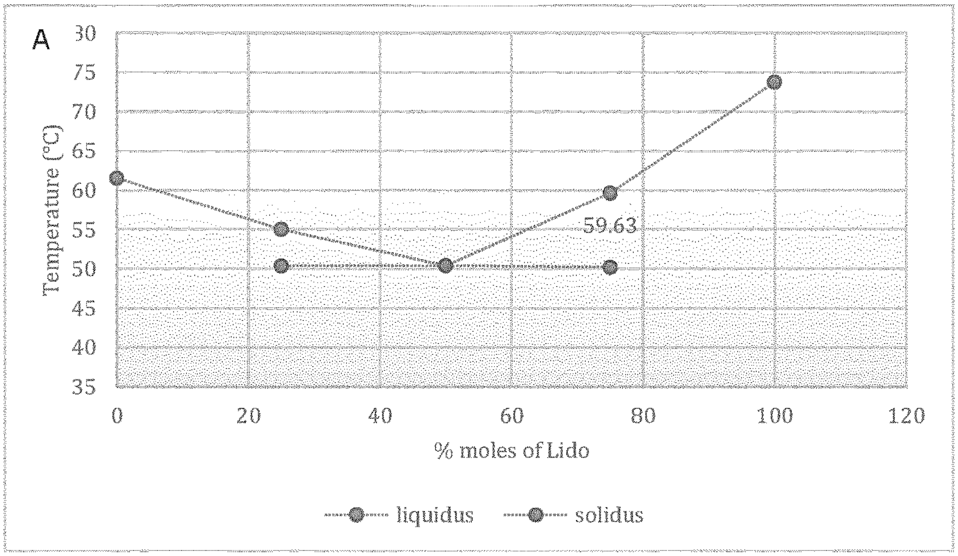
FIG. 37 is a graphical representation of thermal behaviour of IBU-PA binary mixtures as described in Example 9 herein.

As previously observed for lidocaine, the liquidus line predicted using the Van't Hoff equation was at higher temperatures than that observed experimentally and the temperature variation widened as the molar fraction approached the eutectic point (see FIG. 37).

Example 10: Preparation of Lidocaine Eutectics in Polycaprolactone

This study assessed the preparation of eutectic compositions comprising lidocaine (LIDO) and fatty acids in the polymer polycaprolactone (PCL).

PCL films containing lidocaine, either alone or as a eutectic with myristic acid were prepared by solvent casting method using dichloromethane as the solvent. The various compositions are shown in Table 26 below.

TABLE 26

PCL film compositions.

| | Composition (% w/w) | | | | |
|---|---|---|---|---|---|
| Ingredient | Film PCL | Film PCL2-1 | Film PCL2-2 | Film PCL2-3 | Film PCL2-4 |
| PCL | 100% | 80% | 60% | 70% | 40% |
| Lidocaine | — | 20% | 20% | 30% | 30% |
| Myristic acid | — | — | 20% | — | 30% |
| Observation at 8 weeks | Translucent | Opaque and stiff | Translucent and waxy | Opaque and stiff | Translucent and waxy |

Figure 38:
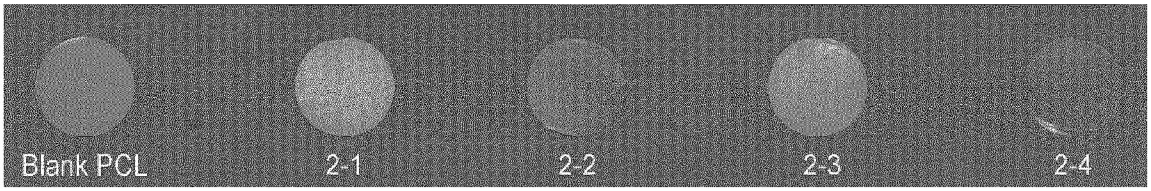
FIG. 38 shows blank PCL film and Film PCL2-1 (20% lidocaine in PCL), Film PCL2-2 (20% Lidocaine/MA (1:1M) in PCL), Film PCL2-3 (30% lidocaine in PCL) and Film PCL2-4 (30% Lidocaine/MA (1:1M) in PCL).

Significant difference in texture and mechanical properties of the films were apparent with and without Myristic acid. The PCL films with only lidocaine were comparatively stiff and opaque. Crystallization/precipitation was evident in the PCL-lidocaine films at both concentrations (i.e. PCL2-1 and PCL2-3) and they were difficult to remove from the supporting substrate. The PCL films with lidocaine and Myristic acid eutectic (i.e. PCL2-2 and PCL2-4) were transparent and waxier with their texture being more similar to the blank PCL film. The weight of Film PCL2-1 and Film PCL2-2 having 20% lidocaine or lidocaine:Myristic acid was 0.015±0.001 g, while that of Film PCL2-3 and Film PCL2-4 films having 30% lidocaine or lidocaine:Myristic acid was 0.013±0.001 g (mean±SD). FIG. 38 shows the visual appearance of the various films.

FTIR studies showed a decrease in intensity of hydrogen-bonded N—H bands of lidocaine with flattening of peak and band shift in the presence of myristic acid, suggesting that amide group is involved in hydrogen bonding with myristic acid to stabilise the drug.

The C═O peak of PCL is at 1724 cm-1. In the PCL films containing lidocaine only, intensity of the C═O peak of PCL was reduced suggesting its involvement in hydrogen bonding with the N—H group of lidocaine. In the presence of MA, however, the C═O peak of PCL remained intact.

Figure 39A:
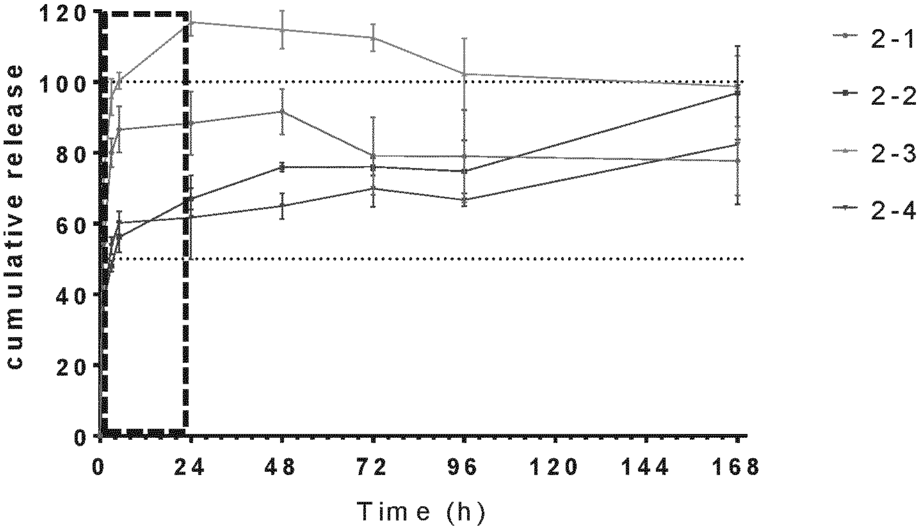
FIG. 39 is two graphs showing A) drug release over 168 h and B) drug release over 24 h from Film PCL2-1 (20% lidocaine in PCL), Film PCL2-2 (20% Lidocaine/MA (1:1M) in PCL), Film PCL2-3 (30% lidocaine in PCL) and Film PCL2-4 (30% Lidocaine/MA (1:1M) in PCL); n=3; mean t SEM.
Figure 39B:
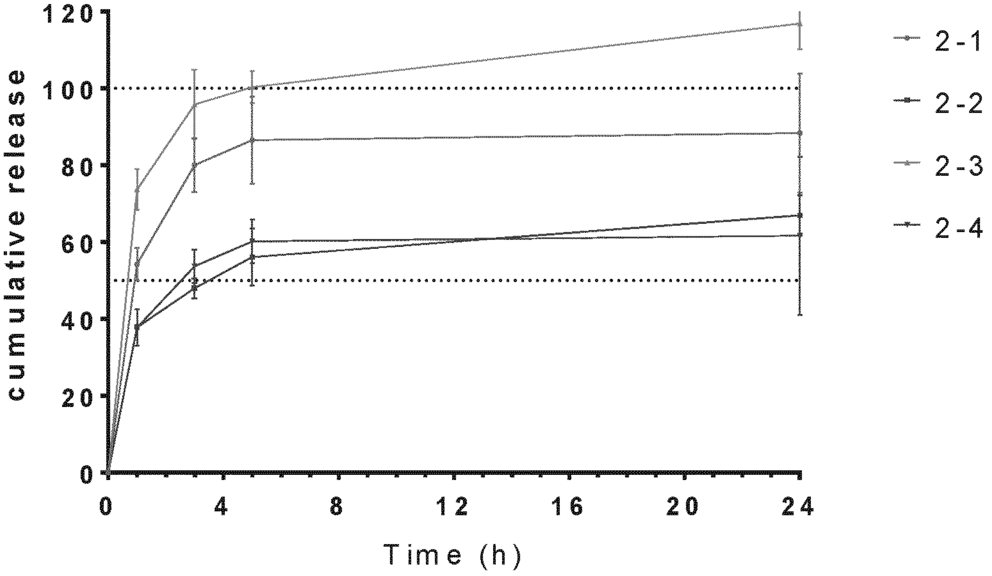
Figure 40A:
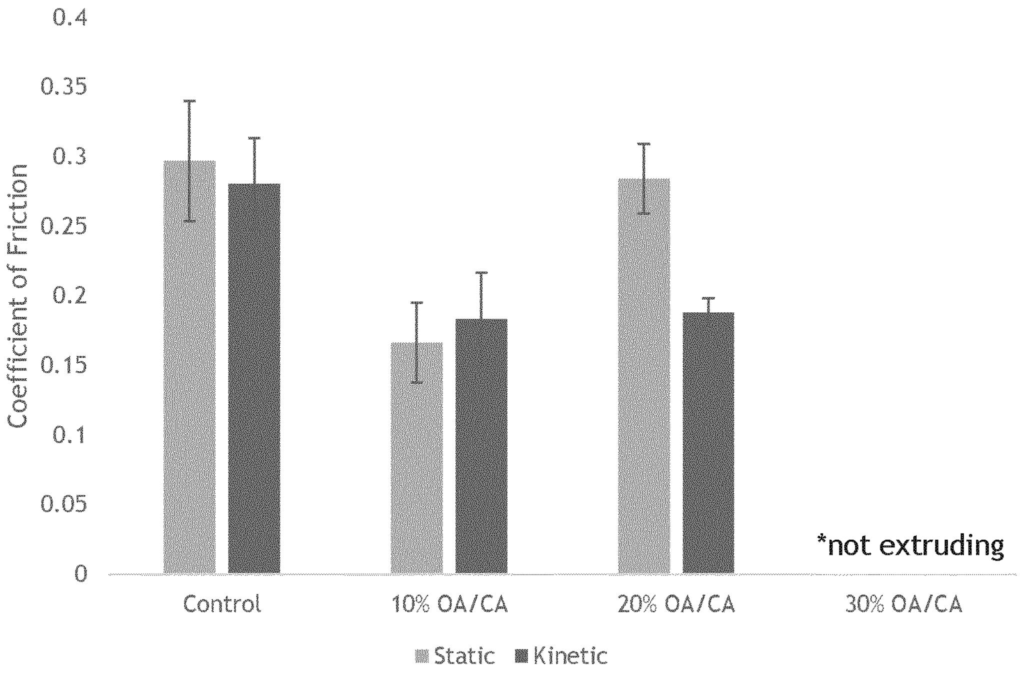
FIG. 40 is four graphs showing the results of testing lubricity in extrudates comprising polymer and 10% eutectic mixture, 20% eutectic mixture, or 30% eutectic mixture, as described on page 42 herein. A) extrudates comprising eutectic mixture of oleic acid/capric acid (eutectic ratio 80 OA:20 CA). B) extrudates comprising eutectic mixture of capric acid/lauric acid (eutectic ratio 65 CA:35 LA). C) extrudates comprising eutectic mixture of oleic acid/lauric acid (eutectic ratio 80 OA:20 LA0. D) extrudates comprising eutectic mixture of capric acid/myristic acid (eutectic ratio 75 CA:25 MA).
Figure 40B:
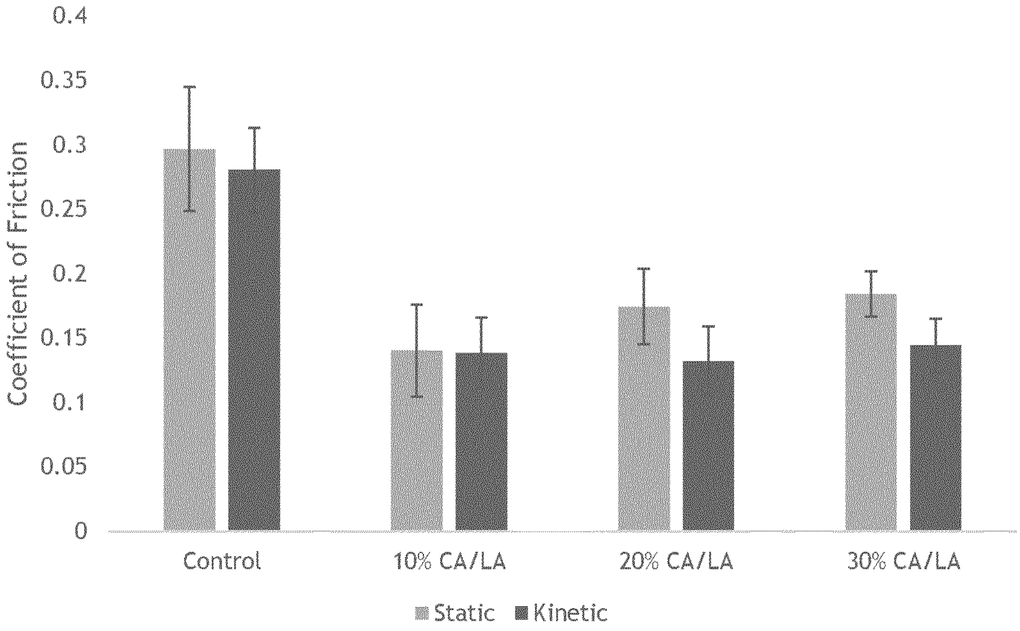
Figure 40C:
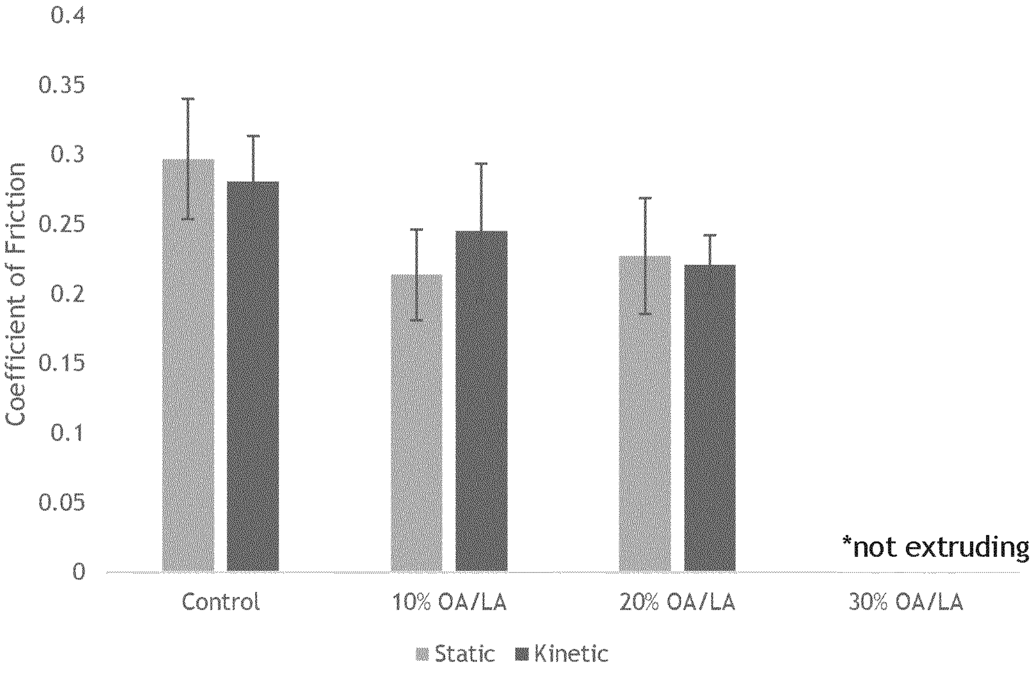
Figure 40D:
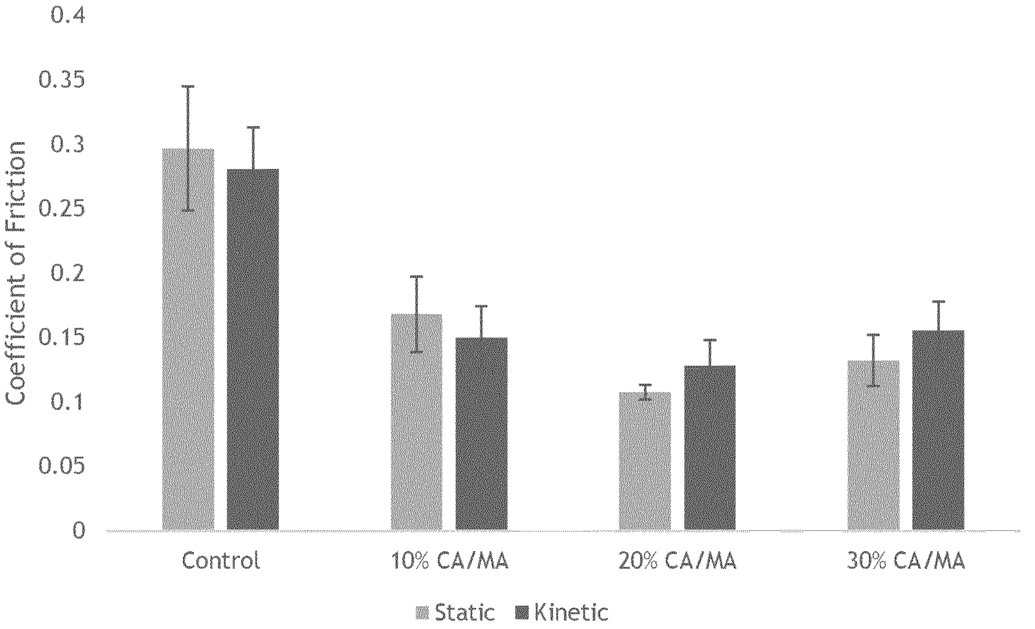

Drug release from PCL films in PBS was also evaluated over 7 days. Release studies showed a significant reduction in burst release of lidocaine during the first 6 hours from PCL2-2 and PCL2-4 films containing the lidocaine:myristic acid eutectic, as shown in FIG. 39. Therefore, the Lidocaine: MA PCL films are expected to be useful in extending the duration of drug release and provide a more sustained effect.

These results show the enhancements in drug stability, and the increased drug loading capacity, of polymer compositions comprising eutectic compositions with various analgesics or anaesthetics and fatty acids.

As used in this specification, the words "comprise", "comprises", "comprising", and similar words, are not to be interpreted in an exclusive or exhaustive sense. In other words, they are intended to mean "including, but not limited to". When interpreting each statement in this specification that includes the term "comprise", "comprises", or"comprising", features other than that or those prefaced by the term may also be present.

The entire disclosures of all applications, patents and publications cited above and below, if any, are herein incorporated by reference.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention may also be said broadly to consist in the parts, elements and features referred to or indicated in the specification of the application, individually or collectively, in any or all combinations of two or more of said parts, elements or features.

Aspects of the invention have been described by way of example only, and it should be appreciated that variations, modifications and additions may be made without departing from the scope of the invention, for example when present the invention as defined in the indicative claims. Furthermore, where known equivalents exist to specific features, such equivalents are incorporated as if specifically referred in this specification.

The invention claimed is:

1. An insertable or implantable device comprising:

a) at least one biocompatible polymer, wherein the at least one biocompatible polymer is selected from the group comprising, polyethylene-vinyl-acetate (EVA), polyvinyl acetate, silicone, polycaprolactone, polylactic-co-glycolic acid (PLGA), polylactic acid (PLA), and polyglycolic acid; and b) eutectic composition consisting essentially of:
lidocaine and ibuprofen; or
lidocaine and myristic acid; or
lidocaine and palmitic acid; or
lidocaine, palmitic acid, and oleic acid; or
bupivacaine and myristic acid; or
bupivacaine, myristic acid, and oleic acid; or
bupivacaine, myristic acid, and lauric acid; or
ropivacaine and myristic acid; or
ropivacaine and palmitic acid; or
ibuprofen and palmitic acid; or
ropivacaine and ibuprofen.

2. The device of claim 1, wherein the device has a cross-sectional diameter of about 5 mm.

3. The device of claim 1, wherein the device a) comprises EVA optionally in a 3:2 w/w ratio with the eutectic composition; or b) is formulated with polycaprolactone.

4. The insertable or implantable device of claim 1, wherein the eutectic composition consists essentially of lidocaine and ibuprofen.

* * * * *